US012054556B2

(12) United States Patent
Li et al.

(10) Patent No.: US 12,054,556 B2
(45) Date of Patent: *Aug. 6, 2024

(54) ANTI-PD-L1 ANTIBODY AND USE THEREOF

(71) Applicant: ORICELL THERAPEUTICS CO., LTD., Shanghai (CN)

(72) Inventors: Bohua Li, Shanghai (CN); Huajing Wang, Shanghai (CN); Xiaowen He, Shanghai (CN)

(73) Assignee: Oricell Therapeutics Co., Ltd., Pudong (CN)

( * ) Notice: Subject to any disclaimer, the term of this patent is extended or adjusted under 35 U.S.C. 154(b) by 780 days.

This patent is subject to a terminal disclaimer.

(21) Appl. No.: 17/225,448

(22) Filed: Apr. 8, 2021

(65) Prior Publication Data
US 2021/0261677 A1    Aug. 26, 2021

Related U.S. Application Data

(63) Continuation of application No. 17/046,265, filed as application No. PCT/CN2018/102584 on Aug. 27, 2018.

(30) Foreign Application Priority Data

Apr. 9, 2018    (CN) .......................... 201810309302.5

(51) Int. Cl.
*C07K 16/28* (2006.01)
*A61P 35/00* (2006.01)

(52) U.S. Cl.
CPC .......... *C07K 16/2878* (2013.01); *A61P 35/00* (2018.01); *C07K 2317/31* (2013.01); *C07K 2317/565* (2013.01); *C07K 2317/622* (2013.01)

(58) Field of Classification Search
None
See application file for complete search history.

(56) References Cited

U.S. PATENT DOCUMENTS

| 9,789,183 B1 | 10/2017 | Wang et al. |
| 10,059,769 B2 | 8/2018 | Fang et al. |
| 2017/0319690 A1 | 11/2017 | Wang et al. |
| 2018/0002423 A1 | 1/2018 | Wang et al. |

FOREIGN PATENT DOCUMENTS

| CN | 105669862 A | 6/2016 |
| CN | 107428832 A | 12/2017 |
| CN | 107488229 A | 12/2017 |
| WO | WO 2017/215590 A1 | 12/2017 |

OTHER PUBLICATIONS

International Search Report issued on Jan. 14, 2019 in PCT/CN2018/102584 filed on Aug. 27, 2018, 5 pages.

*Primary Examiner* — Aurora M Fontainhas
*Assistant Examiner* — Jennifer A Benavides
(74) *Attorney, Agent, or Firm* — Oblon, McClelland, Maier & Neustadt, L.L.P.

(57) ABSTRACT

Provided are an antibody that binds to the PD-L1 protein or CD137 protein, an antigen-binding fragment or a variant thereof, as well as a bispecific antibody that can bind to both the PD-L1 protein and the CD137 protein. The bispecific antibody has a strong ability to specifically recognize the PD-L1 protein and the CD137 protein, and can enhance T-cell activity. Also provided is the use of the antibody or the antigen-binding fragment or the variant thereof and the bispecific antibody in the prevention and treatment of tumors.

13 Claims, 15 Drawing Sheets
Specification includes a Sequence Listing.

Heavy chain variable region (CDR is underlined)

Germline IGHV 1-69
QVQLVQSGAEVKKPGSSVKVSCKASGGTFS<u>SYAIS</u>WVRQAPGQGLEWMG<u>RIIPILGIANYA</u>
<u>QKFQG</u>RVTITADKSTSTAYMELSSLRSEDTAVYYCAR----<u>GYSYGNFDY</u>WGQGTLVTVSS YN-002VH
QVQLVQSGAEVRKPGSSVKVSCKASGGTFS<u>SYAIS</u>WVRQAPGQGLEWMG<u>RIIPILGIANYA</u>
<u>QKFQG</u>RVTITADKSTSTAYMELSSLRSEDTAVYYCARTMD<u>GYSYGNFDY</u>WGQGTLVTVSS YN-003VH
QVQLVQSGAEVKKPGSSVKVSCKASGGTFS<u>SYAIS</u>WVRQAPGQGLEWMG<u>RIIPILGIANYA</u>
<u>QKFQG</u>RVTITADKSTSTAYMELSSLRSEDTAVYYCARTMD<u>GYSYGNFDY</u>WGQGTLVTVSS Light chain variable region (CDR is underlined)

Germline IGLV2-14
QSALTQPASVSGSPGQSITISC<u>TGTSSDVGGYNYVS</u>WYQQHPGKAPKLMIY<u>EVSNRPS</u>GV
SNRFSGSKSGNTASLTISGLQAEDEADYYC<u>SSYTSS----V</u>FGGGTKLTVLG YN-002VL
QSALTQPASVSGSPGQSITISC<u>TGTSSDVGGYNYVS</u>WYQQHPGKAPKLLIY<u>GNSNRPS</u>GV
PDRFSGSKSGTSASLAITGLQAEDEADYYC<u>QSYDSSLSGSV</u>FGGGTKLTVLG YN-003VL
QSALTQPASVSGSPGQSITISC<u>TGTSSDVGGYNYVS</u>WYQQHPGKAPKLMIY<u>GNSNRPS</u>GV
SNRFSGSKSGNTASLTISGLQAEDEADYYC<u>QSYDSSLSGSV</u>FGGGTKLTVLG

Fig. 1

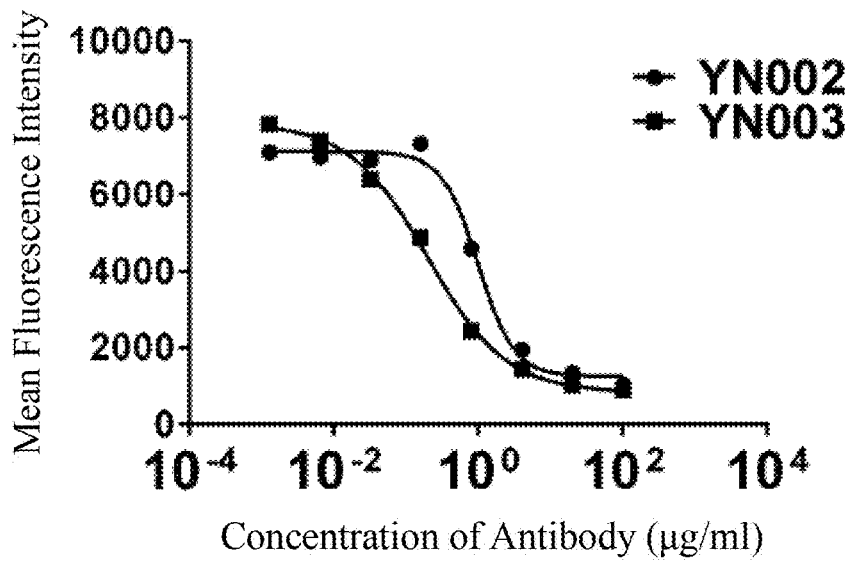

Fig. 2

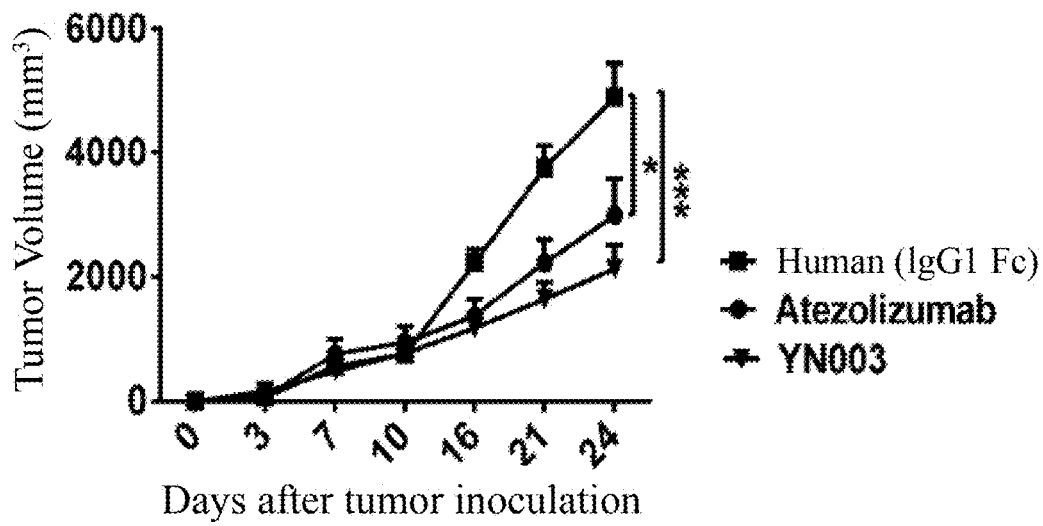

Fig. 5

Heavy chain variable region (CDR is underlined)

| | |
|---|---|
| Germline IGHV 3-23 | QVQLVESGGGLVQPGGSLRLSCAASGFTFSSYAMSWVRQAPGKGLEWVSAISGSGGSTYYAD SVKGRFTISRDNSKNTLYLQMNSLRAEDTAVYYCAKTNWG----DAFDIWGQGTMVTVSS |
| YN-005VH | QVQLVQSGGGLVQPGGSLRLSCAASGFTFSSYAMSWVRQAPGKGLEWVSAISGSGGSTYYAD SVKGRFTISRDNSKNTLYLQMNSLRAEDTAVYYCAKTNWSPSDAFDIWGQGTMVTVSS |
| YN-006VH | QVQLVESGGGLVQPGGSLRLSCAASGFTFSSYAMSWVRQAPGKGLEWVSAISGSGGSTYYAD SVKGRFTISRDNSKNTLYLQMNSLRAEDTAVYYCAKTNWSPSDAFDIWGQGTMVTVSS |

Light chain variable region (CDR is underlined)

| | |
|---|---|
| Germline IGLV1-44 | QSVLTQPPSASGTPGQRVTISCSGSSSNIGSNTVNWYQQLPGTAPKLLIYSNNQRPSGVPDR FSGSKSGTSASLAISGLQSEDEADYYCAAWDDSLNGYVFGTGTKLTVLG |
| YN-005VL | QSVLTQPPSASGTPGQRVTISCSGSTSDIGSYSNWYQQLPGTAPKLLIYSNNQRPSGVPDR FSGSKSGTSASLAISGLQSEDEADYYCAAWDDSLNGYVFGTGTKLTVLG |
| YN-006VL | QSVLTQPPSASGTPGQRVTISCSGSTSDIGSYSNWYQQLPGTAPKLLIYSNNQRPSGVPDR FSGSKSGTSASLAISGLQSEDEADYYCAAWDDSLNGYVFGTGTKLTVLG |

Heavy chain variable region (CDR is underlined)

Light chain variable region (CDR is underlined)

Fig. 9

Heavy chain variable region (CDR is underlined)

ANTI-PD-L1 ANTIBODY AND USE THEREOF

CROSS REFERENCE TO RELATED APPLICATIONS

The present application is a continuation of U.S. patent application Ser. No. 17/046,265, filed on Oct. 8, 2020, which is a 35 U.S.C. § 371 national stage patent application of international patent application PCT/CN2018/102584, filed on Aug. 27, 2018, the text of which is incorporated by reference, and claims the benefit of the filing date of Chinese Application No. 201810309302.5, filed on Apr. 9, 2018, the text of which is also incorporated by reference.

TECHNICAL FIELD

The present application relates to the biomedical field, especially to an anti-PD-L1 antibody, further relates to a method of treating cancers by using such antibody in combination with an anti-CD137 antibody, and further relates to a bispecific antibody formed by such antibody and an anti-CD137 antibody.

BACKGROUND

Programmed death-1 (PD-1, also known as CD279) and its ligands PD-L1 (also known as B7-H1, CD274) and PD-L2 (also known as B7-DC, CD273) cooperate to provide a negative co-stimulatory signal to regulate the activation of T cells. In the absence of the co-stimulatory signal, T cells are hard to feel antigenic stimulation, cannot provide an effective immune response, and can also result in exhaustion or tolerance to heterogeneous antigens. PD-1 can be expressed in T cells, B cells, natural killer T cells, activated mononuclear cells and dendritic cells (DCs). PD-1 can be expressed by activated, but not stimulated human CD4$^+$ and CD8$^+$ T cells, B cells and bone marrow cells. PD-L1 and PD-L2 are different from each other in their expression modes. PD-L1 can be expressed in not only hematopoietic cells, but also in a variety of non-hematopoietic cells, wherein the expression of PD-L2 is primarily limited in dendritic cells and macrophages. B7.1 (CD80) is also a PD-L1 receptor that is expressed in activated B cells, T cells, macrophages and dendritic cell. As the ligands of PD-1 and B7.1, PD-L1 is also selectively expressed in a variety of tumor cells. Inhibition of PD-L1 signal transduction includes blocking the interaction between PD-L1 and either or both of PD-1 and B7.1, thereby preventing PD-L1 from sending a negative co-stimulatory signal to T cells and other antigen-presenting cells. It may enhance the immune to infection (e.g., acute or chronic) response and the tumor immune.

CD137 (also known as 4-1BB, TNFRSF9, etc.) is a transmembrane protein of tumor necrosis factor superfamily (TNFRS). Studies indicate that CD137-activated monoclonal antibody increases the expression of co-stimulatory molecules in many models, significantly enhances the response of cytolytic T lymphocytes, and plays an antitumor role. The antitumor effect of CD137-targeted therapies is demonstrated by studies involving the antitumor therapeutic effect of activated anti-mouse CD137 monoclonal antibody in mice.

Currently, PD-L1 antibodies have been approved for use in treating some cancers, and the existing CD137 antibodies exhibit a potential of treating a variety of tumors. It has been reported that the antitumor therapeutic effect of PD-1 antibody in combination with CD137 antibody is studied by use of tumor-bearing mouse model. The results show that the two antibodies used in combination exhibit a significantly enhanced tumor-inhibiting activity as compared with them used alone, but from the viewpoint of compliance and pain, the combination therapy brings inconvenience to patients and increases treatment costs. Development of bispecific antibody (BsAb) of the two monoclonal antibodies can solve the aforesaid problem due to the presence of two specific antigen-binding sites in the bispecific antibody. Thus, there is an urgent need of developing a novel anti-PD-L1 antibody having better pharmaceutical efficacy and lower immunogenicity and a PD-L1/CD137 bispecific antibody to give a better antitumor effect.

SUMMARY OF THE INVENTION

The present application provides a PD-L1 antibody, an antigen binding fragment or a variant thereof which have one or more of the following properties: 1) capable of binding the PD-L1 protein with high affinity and specificity; 2) capable of inhibiting the binding of the PD-1 protein to the PD-L1 protein; and 3) capable of relieving or treating tumors. The present application further provides a bispecific antibody having one or more of the following properties: 1) capable of binding to the PD-L1 protein with high affinity and specificity; 2) capable of binding to the CD137 protein with high affinity and specificity; 3) capable of enhancing the functions of T cells; and 4) capable of relieving or treating tumor. The present application further provides a preparation method and use of the PD-L1 antibody, the antigen binding fragment or the variant thereof, bispecific antibody.

In one aspect, the present application provides an antibody, an antigen binding fragment or a variant thereof which binds to the PD-L1 protein with a $K_D$ of $3 \times 10^{-9}$ M or less.

In some embodiments, the antibody includes an antibody light chain or a fragment thereof which includes a LCDR1, and the LCDR1 includes an amino acid sequence shown in SEQ ID NO: 53: TGTX$_1$SX$_2$VGGYX$_3$X$_4$VS; wherein X$_1$ is S, R or V; X$_2$ is D, E or S; X$_3$ is N or R; X$_4$ is Y or E, and wherein the LCDR1 is determined according to the index of the antibody Kabat number.

In some embodiments, the LCDR1 includes an amino acid sequence selected from the group consisting of SEQ ID NO: 54-58. In some embodiments, the antibody light chain or the fragment thereof includes a LCDR2 including an amino acid sequence shown in SEQ ID NO: 59: X$_1$NSX$_2$RPS, wherein X$_1$ is G or E; X$_2$ is N or I, and wherein the LCDR2 is determined according to the index of the antibody Kabat number. In some embodiments, the LCDR2 includes an amino acid sequence selected from the group consisting of SEQ ID NO: 60-61. In some embodiments, the antibody light chain or the fragment thereof includes a LCDR3 including an amino acid sequence shown in SEQ ID NO: 62: QSYDSSLSGX$_1$V, wherein X$_1$ is S or T, and wherein the LCDR3 is determined according to the index of the antibody Kabat number.

In some embodiments, the antibody light chain or a fragment thereof further includes framework regions L-FR1, L-FR2, L-FR3, and L-FR4. In some embodiments, the framework regions are selected from the group consisting of human consensus framework sequences and human germline sequences. In some embodiments, a C-terminus of the L-FR1 is directly or indirectly linked to an N-terminus of the LCDR1, and the L-FR1 includes an amino acid sequence selected from the group consisting of SEQ ID NO: 71. In some embodiments, the L-FR2 is located between the LCDR1 and the LCDR2, and the L-FR2 includes an amino acid sequence selected from the group consisting of SEQ ID NO: 72. In some embodiments, the L-FR3 is located between the LCDR2 and the LCDR3, and the L-FR3 includes an amino acid sequence selected from the group consisting of SEQ ID NO: 73-75. In some embodiments, the N-terminus of the L-FR4 is directly or indirectly linked to the C-terminus of the LCDR3, and the L-FR4 includes an amino acid sequence selected from the group consisting of SEQ ID NO: 76.

In some embodiments, the antibody light chain or the fragment thereof includes a light chain variable region VL, and the light chain variable region VL includes an amino acid sequence selected from the group consisting of SEQ ID NO: 4, SEQ ID NO: 11, SEQ ID NO: 33, SEQ ID NO: 37, SEQ ID NO: 39 and SEQ ID NO: 41.

In some embodiments, the antibody light chain or the fragment thereof further includes a human constant region, and the human constant region includes a human Ig, constant region.

In some embodiments, the antibody light chain or the fragment thereof includes an amino acid sequence selected from the group consisting of SEQ ID NO: 8, SEQ ID NO: 15, SEQ ID NO: 34, SEQ ID NO: 38, SEQ ID NO: 40 and SEQ ID NO: 42.

In some embodiments, the antibody includes an antibody heavy chain or a fragment thereof which includes a HCDR1, and the HCDR1 includes an amino acid sequence selected from the group consisting of those shown in SEQ ID NO: 45: $X_1$YAIS, wherein $X_1$ is S or T, and wherein the HCDR1 is determined according to the index of the antibody Kabat number. In some embodiments, the antibody heavy chain or a fragment thereof includes a HCDR2, the HCDR2 includes an amino acid sequence shown in SEQ ID NO: 48, and wherein the HCDR2 is determined according to the index of the antibody Kabat number. In some embodiments, the antibody heavy chain or a fragment thereof includes a HCDR3, and the HCDR3 includes an amino acid sequence selected from the group consisting of those shown in SEQ ID NO: 49: TMX$_1$X$_2$YX$_3$X$_4$GNX$_5$DY, wherein X$_1$ is D, E or G, X$_2$ is G or E, X$_3$ is S or G, X$_4$ is Y or F, X$_5$ is F or Y, and wherein the HCDR3 is determined according to the index of the antibody Kabat number. In some embodiments, the HCDR3 includes an amino acid sequence shown in the group of SEQ ID NO: 50-52.

In some embodiments, the antibody heavy chain or the fragment thereof further includes framework regions H-FR1, H-FR2, H-FR3, and H-FR4. In some embodiments, the framework regions are selected from the group consisting of human consensus framework sequences and human germline sequences. In some embodiments, a C-terminus of H-FR1 is directly or indirectly linked to an N-terminus of HCDR1, and the H-FR1 includes an amino acid sequence selected from the group consisting of SEQ ID NO: 65-67. In some embodiments, the H-FR2 is located between the HCDR1 and the HCDR2, and the H-FR2 includes an amino acid sequence selected from the group consisting of SEQ ID NO: 68. In some embodiments, the H-FR3 is located between the HCDR2 and the HCDR3, and the H-FR3 includes an amino acid sequence selected from the group consisting of SEQ ID NO: 69. In some embodiments, the N-terminus of H-FR4 is directly or indirectly linked to the C-terminus of HCDR3, and the H-FR4 includes an amino acid sequence selected from the group consisting of SEQ ID NO: 70.

In some embodiments, the antibody heavy chain or the fragment thereof includes a heavy chain variable region VH, and the heavy chain variable region VH includes an amino acid sequence selected from the group consisting of SEQ ID NO: 2, SEQ ID NO: 9, SEQ ID NO: 31 and SEQ ID NO: 35.

In some embodiments, the antibody heavy chain or the fragment thereof further includes a human constant region, and the human constant region includes a human IgG1 constant region.

In some embodiments, the antibody heavy chain or the fragment thereof includes an amino acid sequence selected from the group consisting of SEQ ID NO: 6, SEQ ID NO: 13, SEQ ID NO: 32 and SEQ ID NO: 36.

In some embodiments, the PD-L1 protein is selected from the group consisting of human PD-L1 protein, monkey PD-L1 protein and murine PD-L1 protein.

In another aspect, the present application provides an antibody, an antigen binding fragment or a variant thereof which binds to a CD137 protein with a $K_D$ of $5 \times 10^{-9}$ M or less.

In some embodiments, the antibody, the antigen binding fragment or the variant thereof binds to a CD137 protein with a $K_D$ of $3 \times 10^{-9}$ M or less.

In some embodiments, the antibody, the antigen binding fragment or the variant thereof may relieve or treat tumors. In some embodiments, the antibody, the antigen binding fragment or the variant thereof may relieve or treat colon cancer.

In some embodiments, the antibody includes an antibody light chain or a fragment thereof. In some embodiments, the light chain or the fragment thereof includes LCDR1-3, and the amino acid sequences of LCDR1-3 are sequentially shown in SEQ ID NO: 80-82. In some embodiments, the antibody light chain or the fragment thereof further includes framework regions L-FR1, L-FR2, L-FR3 and L-FR4. In some embodiments, the framework regions are selected from the group consisting of human consensus framework sequences and human germline sequences. In some embodiments, a C-terminus of the L-FR1 is directly or indirectly linked to an N-terminus of the LCDR1, and the L-FR1 includes an amino acid sequence shown in SEQ ID NO: 89. In some embodiments, the L-FR2 is located between the LCDR1 and the LCDR2, and the L-FR2 includes an amino acid sequence shown in SEQ ID NO: 90. In some embodiments, the L-FR3 is located between the LCDR2 and the LCDR3, and the L-FR3 includes an amino acid sequence shown in SEQ ID NO: 91. In some embodiments, the N-terminus of the L-FR4 is directly or indirectly linked to the C-terminus of the LCDR3, and the L-FR4 includes an amino acid sequence shown in SEQ ID NO: 92.

In some embodiments, the antibody light chain or the fragment thereof includes a light chain variable region VL, and the light chain variable region VL includes an amino acid sequence shown in SEQ ID NO: 20.

In some embodiments, the antibody light chain or the fragment thereof further includes a human constant region and the human constant region includes a human Igλ constant region.

In some embodiments, the antibody light chain or the fragment thereof includes an amino acid sequence shown in SEQ ID NO: 23.

In some embodiments, the antibody includes an antibody heavy chain or a fragment thereof, wherein the heavy chain or the fragment thereof includes HCDR1-3, and the amino acid sequences of the HCDR1-3 are sequentially shown in SEQ ID NO: 77-79. In some embodiments, the antibody heavy chain or the fragment thereof further includes framework regions H-FR1, H-FR2, H-FR3 and H-FR4. In some embodiments, the framework regions are selected from the group consisting of human consensus framework sequences and human germline sequences. In some embodiments, a C-terminus of H-FR1 is directly or indirectly linked to an N-terminus of HCDR1, and the H-FR1 includes an amino acid sequence shown in SEQ ID NO: 84-85. In some embodiments, the H-FR2 is located between the HCDR1 and the HCDR2, and the H-FR2 includes an amino acid sequence shown in SEQ ID NO: 86. In some embodiments, the H-FR3 is located between the HCDR2 and the HCDR3, and the H-FR3 includes an amino acid sequence shown in SEQ ID NO: 87. In some embodiments, the N-terminus of H-FR4 is directly or indirectly linked to the C-terminus of HCDR3, and the H-FR4 includes an amino acid sequence shown in SEQ ID NO: 88.

In some embodiments, the antibody heavy chain or the fragment thereof includes a heavy chain variable region VH, and the heavy chain variable region VH includes an amino acid sequence selected from the group consisting of SEQ ID NO: 18 and SEQ ID NO: 25.

In some embodiments, the antibody heavy chain or the fragment thereof further includes a human constant region, and the human constant region includes a human IgG constant region.

In some embodiments, the antibody heavy chain or the fragment thereof includes an amino acid sequence selected from the group consisting of SEQ ID NO: 21 and SEQ ID NO: 27.

In some embodiments, the CD137 protein includes a human CD137 protein.

In another aspect, the present application provides a bispecific antibody which binds to a PD-L1 protein with a $K_D$ of $2\times10^{-9}$ M or less and binds to a CD137 protein with a $K_D$ of $8\times10^{-9}$ M or less.

In some embodiments, the bispecific antibody includes a first targeting moiety that specifically binds to the PD-L1 protein, wherein the first targeting moiety includes the antibody, the antigen binding fragment or the variant thereof.

In some embodiments, the bispecific antibody includes a second targeting moiety that specifically binds to the CD137 protein, wherein the second targeting moiety includes an antibody, an antigen binding fragment or a variant thereof which binds to the CD137 protein. In some embodiments, the antibody that binds to the CD137 protein includes a scFv, and the scFv includes an amino acid sequence shown in SEQ ID NO: 83. In some embodiments, the bispecific antibody includes a first polypeptide chain and a second polypeptide chain, wherein the first polypeptide chain includes the heavy chain variable region of the antibody that binds to the PD-L1 protein, the heavy chain variable region of the antibody that binds to the CD137 protein, and the light chain variable region of the antibody that binds to the CD137 protein; and the second polypeptide chain includes the light chain variable region of the antibody that binds to the PD-L1 protein.

In some embodiments, in the first polypeptide chain, the heavy chain variable region of the antibody that binds to the PD-L1 protein is located at an N-terminus of the heavy chain variable region of the antibody that binds to the CD137 protein, and the heavy chain variable region of the antibody that binds to the CD137 protein is located at the N-terminus of the light chain variable region of the antibody that binds to the CD137 protein; alternatively, the heavy chain variable region of the antibody that binds to the PD-L1 protein is located at the N-terminus of the light chain variable region of the antibody that binds to the CD137 protein, and the light chain variable region of the antibody that binds to the CD137 protein is located at the N-terminus of the heavy chain variable region of the antibody that binds to the CD137 protein.

In some embodiments, the light chain variable region of the antibody that binds to the CD137 protein and the heavy chain variable region of the antibody that binds to the CD137 protein in the first polypeptide chain constitute scFv.

In some embodiments, the first polypeptide chain further includes a human IgG constant region, and the human IgG constant region is located at a C-terminus of the heavy chain variable region of the antibody that binds to the PD-L1 protein and located at an N-terminus of the light chain variable region of the antibody that binds to the CD137 protein; alternatively, the human IgG constant region is located at the C-terminus of the heavy chain variable region of the antibody that binds to the PD-L1 protein and located at the N-terminus of the heavy chain variable region of the antibody that binds to the CD137 protein.

In some embodiments, the first polypeptide chain includes an amino acid sequence selected from the group consisting of SEQ ID NO: 30, SEQ ID NO: 43 and SEQ ID NO: 44. In some embodiments, the second polypeptide chain includes an amino acid sequence selected from the group consisting of SEQ ID NO: 15 and SEQ ID NO: 34.

In another aspect, the present application provides one or more nucleic acid molecules which encode the antibody, the antigen binding fragment or the variant thereof, or the bispecific antibody.

In another aspect, the present application provides a vector which includes the nucleic acid molecule.

In another aspect, the present application provides a cell which includes the nucleic acid molecule or the vector.

In another aspect, the present application provides a method of preparing the antibody, the antigen binding fragment or the variant thereof, or the bispecific antibody, including culturing the cells under conditions that allow the expression of the antibody, the antigen binding fragment or the variant thereof, or the bispecific antibody.

In another aspect, the present application provides a pharmaceutical composition which includes the antibody, the antigen binding fragment or the variant thereof, or the bispecific antibody, the nucleic acid molecule, the vector and/or the cell, and optionally a pharmaceutical acceptable adjuvant.

In another aspect, the present application provides use of the antibody, the antigen binding fragment or the variant thereof, or the bispecific antibody, the nucleic acid molecule, the vector, the cell and/or the pharmaceutical composition in manufacture of a drug for relieving or treating tumors.

In another aspect, the present application provides a method of inhibiting the binding of a PD-L1 protein to a PD-1 protein, including administering the antibody, the antigen binding fragment or the variant thereof, or the bispecific antibody, the nucleic acid molecule, the vector, the cell and/or the pharmaceutical composition.

In the present application, the CDR position of the antibody is determined in accordance with the antibody Kabat definition method.

Persons skilled in the art can easily recognize other aspects and advantages of the present disclosure from the detailed description below. The following detailed description only shows and describes exemplary embodiments of the present disclosure. For example, persons skilled in the art will recognize that the content of the present disclosure enables persons skilled in the art to make variations to the disclosed embodiments without departing from the spirit and scope of the invention to which the present application relates. Correspondingly, the accompanying drawings and the description in the specification of the present application are only exemplary, rather than restrictive.

BRIEF DESCRIPTION OF THE DRAWINGS

The specific features of the inventions involved in the present application are shown in the appended claims. By reference to the detailed exemplary embodiments and the accompanying drawings hereinafter, the features and the advantages of the inventions involved in the present application can be better understood. A brief description of the accompanying drawings is as follows:

FIG. 1 shows the amino acid sequence alignment between the PD-L1 antibody heavy chain variable regions and light chain variable regions of the present application and the related germline sequences. The underlined are the CDRs determined in accordance with the Kabat definition method.

FIG. 2 shows the results of the PD-L1 antibody of the present application inhibiting the binding of the human PD-L1 to the human PD-1.

FIG. 5 shows the effect of various antibodies of the present application on the MC38 tumor growth in C57BL/6 mouse (*, P<0.05; ***, P<0.001; Unpaired t-test).

FIG. 6 shows the amino acid sequence alignment between the CD137 antibody heavy chain variable regions and light chain variable regions of the present application and related germline sequences, wherein the underlined are the CDRs determined in accordance with the Kabat definition method.

FIG. 8 shows the amino acid sequence alignment between the PD-L1 antibody heavy chain variable regions and light chain variable regions in the present application and related germline sequences, wherein the underlined are the CDRs determined in accordance with the Kabat definition method, and the shaded parts are the CDRs determined in accordance with the IMGT definition method. The amino acid residues in various CDR regions of YN-003 (including some amino acid residues in the CDR regions and several amino acid residues in the FR regions adjacent to the CDR regions) which are randomly targeted when performing affinity maturation are indicated in italics.

FIG. 9 shows the alignment of the amino acid sequences of the heavy chain variable regions of the PD-L1 antibody of the present application with the related germline sequences. The underlined are the CDRs determined according to the Kabat definition method, and the shaded parts are the CDRs determined according to the IMGT definition method.

DETAILED DESCRIPTION OF THE EMBODIMENTS

Figure 3:
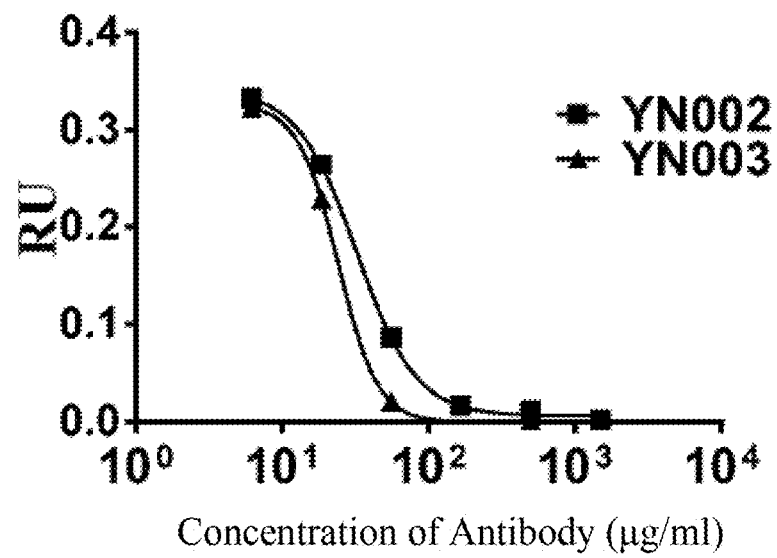
FIG. 3 shows the results of the PD-L1 antibody of the present application inhibiting the binding of *Macaca fascicularis* PD-L1 to the *Macaca fascicularis* PD-1.

Hereinafter the embodiments of the invention involved in the present application are illustrated by specific examples. Those of ordinary skills in the art can easily understand other advantages and effects of the invention disclosed in the present application from the disclosure of the description.

In the present application, the term "antibody" generally refers to a polypeptide molecule capable of specifically recognizing and/or neutralizing a specific antigen. For example, the antibody can include an immunoglobulin composed of at least two heavy (H) chains and two light (L) chains linked via a disulfide bond, and include any molecule including its antigen binding portion. The term "antibody" includes monoclonal antibodies, antibodies fragment or antibodies derivative, including but not limited to, human antibodies, humanized antibodies, chimeric antibodies, single-strand antibodies (e.g., scFv), and antigen-binding fragments of antibodies (e.g., Fab, Fab' and (Fab)₂ fragments). The term "antibody" further includes all the recombinants of an antibody, such as, antibodies expressed in prokaryotic cells, unglycosylated antibodies and any antigen-binding fragment of the antibody as described herein and their derivatives. Each heavy chain can be composed of a heavy chain variable region (VH) and a heavy chain constant region. Each light chain can be composed of light chain variable regions (VLs) and light chain constant regions. VH and VL regions can be further divided to highly variable regions called complementary determinant regions (CDR) which are dispersed in more conserved regions called framework regions (FR). Each VH and VL can be composed of three CDRs and four FRs which can be arranged from the amino terminal to the carboxy terminal in an order of FR1, CDR1, FR2, CDR2, FR3, CDR3 and FR4. The variable regions in the heavy chains and the light chains include binding domains that interact with an antigen. The constant region of the antibody can mediate the binding of the immunoglobulin to a host tissue or factor which includes various cells of immune systems (e.g., effector cells) and the first component of a classical complement system (Clq).

In the present application, the term "PD-L1 protein" generally refers to a ligand of programmed death-1 (PD-1) protein. PD-1 is a receptor of an Ig superfamily which interacts with the specific ligand (PD-L) to negatively regulate the signal transduction of T cells antigen receptor, and is recommended to play a role in maintenance of self tolerance. In the absence of the co-stimulatory signal, T cells are hard to feel the antigen stimulation, cannot produce an effective immune response, and can further cause the exhaustion or tolerance of heterologous antigen. PD-L1 may be expressed in either hematopoietic cells, or in a variety of non-hematopoietic cells. B7.1 (CD80) is also a PD-L1 receptor, which is expressed in activated B cells, T cells, macrophages and dendritic cells. As the ligand of PD-1 and B7.1, PD-L1 is further selectively expressed in a variety of tumor cells. Inhibition of the PD-L1 signal transduction includes blocking the interactions of PD-L1 with either or both of PD-1 and B7.1, thereby preventing PD-L1 from sending a negative co-stimulatory signal to T cells and other antigen-presenting cells. It may enhance the immune for infection (e.g., acute and chronic) response and tumor immune.

In the present application, the term "CD137 protein", also known as 4-1BB or TNFRS9, generally refers to a transmembrane protein of the tumor necrosis factor receptor superfamily (TNFRS), which is an activation-induced co-stimulatory molecule and an important regulator of immune responses. Studies have shown that CD137-activated monoclonal antibodies increase the expression of costimulatory molecules in many models, and significantly enhance the cytolytic T lymphocyte response and exert anti-tumor effects. The anti-tumor effect of CD137-targeted antibody may be demonstrated by the anti-tumor efficacy study in mice by use of activated anti-mouse CD137 monoclonal antibody. CD137 has become a powerful activator of immune cells and an important candidate antigen for the treatment of various diseases. (See Vinay, Dass S., and Byoung S. Kwon. "4-1BB (CD137), an inducible costimulatory receptor, as a specific target for cancer therapy." BMB reports 47.3 (2014): 122.)

In the present application, the term "NFκB" refers to nuclear factor kappa-light-chain-enhancer of activated B cells (NFκB). This is a protein complex that controls DNA transcription. NFκB exists in almost all types of animal cells and participates in the cell's responses to many stimuli, including stress, cytokines, free radicals, UV radiation, oxidation of LDL, and microbial or viral antigens. In the immune response to infection, NFκB plays an important regulatory role (κ light chain is an important part of immunoglobulin). The abnormal regulation of NFκB is associated with cancers, inflammations and autoimmune diseases, septic shocks, viral infections and abnormal immune development. NF-dB is also closely associated with synaptic plasticity and memory processes. The main target cells of NFκB are chemokines, immune receptors, adhesion molecules, stress response genes, apoptosis regulators, transcription factors, growth factors, enzymes and cell cycle regulators. In addition, NFκB has an important influence on the transcription of several viral promoters/enhancers (e.g., HIV-1 and CMV) (see Tergaonkar, Vinay. "NFκB pathway: A good signaling paradigm and therapeutic target." The international journal of biochemistry & cell biology 38.10 (2006): 1647-1653).

In the present application, the term "$K_D$" can be used interchangeably with "KD", and generally refers to the dissociation equilibrium constant of a specific antibody-antigen interaction with the unit of M (mol/L). KD may be calculated from the concentrations of substance AB and substances A and B obtained by dissociation of AB: KD=c(A)*c(B)/c(AB). It can be seen from this formula that the larger the KD value, the more the dissociation, and the weaker the affinity between the substances A and B; on the contrary, the smaller the KD value, the less the dissociation, and the stronger the affinity between the substances A and B.

In the present application, the term "monoclonal antibody" generally refers to a group of antibodies that are substantially homologous, that is, each antibody included in the group is the same except for possible naturally occurring mutations in trace amounts. Monoclonal antibodies are highly specific and are directed against a single antigenic site. In addition, in contrast to polyclonal antibody preparations that include different antibodies directed against different determinants (epitopes), each monoclonal antibody directed against a single determinant on the antigen is not interpreted as requiring any special method to produce antibodies. For example, the monoclonal antibodies may be prepared by hybridoma technology or produced in bacteria, eukaryotic animals or plant cells by recombinant DNA methods. Alternatively, the monoclonal antibodies may be also obtained from a phage antibody library, by using a technology as described in, e.g., Clackson et al., Nature, 352:624-628 (1991) and Marks et al., Mol. Biol., 222:581-597 (1991).

In the present application, the term "single chain antibody (scFv)" usually refers to a molecule formed by linking the variable region of the heavy chain of the antibody to the variable region of the light chain via a short peptide linker (linker).

In the present application, the term "chimeric antibody" generally refers to an antibody in which a portion of the amino acid sequence of each heavy or light chain is homologous to the corresponding amino acid sequence in an antibody from a specific species, or belongs to a specific class, and the rest of the chain is homologous to the corresponding sequence in another species. For example, the variable regions of both the light chain and the heavy chain are derived from the variable region of an antibody from one animal species (e.g., mouse, rat, etc.), while the constant part is homologous to an antibody sequence from another species (e.g., human). For example, for obtaining the chimeric antibodies, non-human B cells or hybridoma cells can be used to generate variable regions, and the constant regions combined therewith are derived from humans. The variable region has an easy-to-prepare advantage, and its specificity is not affected by the source of the constant region combined therewith. At the same time, since the constant region of the chimeric antibody may be derived from humans, the possibility of the chimeric antibody inducing an immune response when injected is lower than that of an antibody of which the constant region is derived from a non-human origin.

In the present application, the term "humanized antibody" generally refers to an engineered antibody obtained by reducing the immunogenicity of the antibodies, immunoglobulin binding proteins and polypeptides derived from non-human species (e.g., mice or rats) to humans, while still retaining the antigen-binding properties of the original antibody. For example, it is feasible to use technical means including CDR grafting (Jones et al., Nature 321:522 (1986)) and a variant thereof, including "reshaping" (Verhoeyen, et al., 1988 Science 239:1534-1536; Riechmann, et al., 1988 Nature 332:323-337; Tempest, et al., Bio/Technol 1991 9:266-271), "hyperchimerization" (Queen, et al., 1989 Proc Natl Acad Sci USA 86:10029-10033; Co, et al., 1991 Proc Natl Acad Sci USA 88:2869-2873; Co, et al., 1992 J Immunol 148:1149-1154) and "veneering", (Mark, et al., "Derivation of therapeutically active humanized and veneered anti-CD18 antibodies." In: Metcalf B W, Dalton B J, eds. Cellular adhesion: molecular definition to therapeutic potential. New York: Plenum Press, 1994: 291-312) or the like to humanize the non-human binding domain. If other regions, such as the hinge region and the constant region domains, are also derived from non-human sources, these regions can also be humanized.

In the present application, the term "fully human antibody" generally means that all pa rts of the antibody (including the constant regions, CH and CL regions of the antibody) are encoded by genes derived from human. The fully human antibody can significantly reduce the immune side effects caused by heterogeneous antibodies on the human body.

In the present application, the term "bispecific antibody (BsAbs)" generally refers to an antibody or antibody construct with dual specificity in its binding arm. Naturally occurring antibodies are monospecific and have the same specificity in their antigen binding arms. Bispecific antibodies are obtained from two different sources and constructed by recombinant DNA or cell fusion technology, so that they retain the two specificities of the original antibody. Bispecific antibodies carry two different antigen binding sites. The Fc part of a bispecific antibody is different from the Fc part of any parental monospecific antibody. Since the bispecific antibodies have dual specificity for both drugs and tumor cells, they may theoretically cause that the drug accumulation in tumors is higher than that in non-tumor sites in the body. Most of the bispecific new antibodies may redirect cytotoxic effector cells (e.g., Tc cells, NK cells, neutrophils) to the targeted cells (e.g., tumor cells). Bispecific antibodies can simultaneously block two different mediators/pathways that play a unique or overlapping role in pathogenesis, and may also increase the binding specificity by interacting with two, instead of one, different cell surface antigens. (Fanger, Michael W., and Paul M. Guyre. "Bispecific antibodies for targeted cellular cytotoxicity." Trends in biotechnology, 1991: 375-380), (Fan, Gaowei, et al. "Bispecific antibodies and their applications." Journal of hematology & oncology, 2015: 130)

In the present application, the term "sequence homology" generally means that the amino acid sequences of homologous proteins have a significant similarity.

In the present application, the term "epitope" usually refers to an antigenic determinant, that is, a part of a molecule that is recognized by the immune system (e.g., recognized by an antibody). For example, epitopes are discrete three-dimensional sites on an antigen recognized by the immune system. An epitope is usually composed of chemically active surface groups of molecules (e.g., amino acids or sugar side chains), and usually has specific three-dimensional structural characteristics and specific charge characteristics. Epitopes can be divided into conformational epitopes and non-conformational epitopes (linear epitopes) according to their structures. The difference between conformational epitopes and non-conformational epitopes is that the former will lose binding in the presence of denaturing solvents, while the latter does not. Epitopes that are only on the surface of antigenic substances and easily bind to the antigen recognition receptors or antibodies can be called functional epitopes; and epitopes that are located within the molecule and are not immunogenic can be called hidden epitopes. Epitopes may be composed of continuous residues, or formed by discontinuous residues that are close to each other due to the folding of the antigenic polymer. Epitopes formed by consecutive amino acids in proteins are usually maintained when exposed to denaturing solvents, but epitopes formed by discontinuous amino acids are usually lost after the exposure.

In the present application, the term "antigen-binding fragment" generally refers to a part of an intact antibody, e.g., the antigen-binding region and/or the variable region of the intact antibody. In some embodiments, the antigen-binding fragment may include Fab, Fab', F(ab)$_2$, F(ab')$_2$, and Fv fragments. In some embodiments, the antibodies of the present application may include double strand antibodies, linear antibodies, single-stand antibody molecules, and multispecific antibodies formed from antibody fragments. The two identical antigen-binding fragments obtained by digesting an antibody having an intact structure with papain (e.g., by removing the Fc region and the hinge region) are called "Fab" fragments. The Fab fragment is composed of an intact light chain, a variable region of the heavy chain (VH) and a first constant domain (CH1) of the heavy chain. Each Fab fragment is monovalent with respect to the antigen binding, that is, it has a single antigen binding site. F(ab)$_2$ antibody fragments were initially produced as pairs of Fab fragments linked via a cysteine. The single and large F(ab')$_2$ fragment obtained by digesting an antibody having an intact structure with pepsin is roughly equal to two Fab fragments linked via disulfide and having different antigen binding activities, and is still capable of cross-linking the antigen. Fab' fragments differ from Fab fragments in that they have several additional residues at the carboxy terminus of the CH1 domain, including one or more cysteines from the hinge region of an antibody. The Fv fragment is composed of the VL and VH domains of one arm of the antibody.

In the present application, the term "variant" generally refers to an amino acid sequence that has substantially the same function (e.g., a capacity of specifically binding to the PD-L1) and at least 85% (e.g., at least 85%, at least 90%, at least 91%, at least 92%, at least 93%, at least 94%, at least 95%, at least 96%, at least 97%, at least 98%, at least 99%, or at least 100%) sequence identity. In some embodiments, the variant of an amino acid sequence is an amino acid sequence that has substantially the same function (e.g., capable of specifically binding to PD-L1), and includes one or more (e.g., 1-2, 1-3, 1-4, 1-5, 1-6, 1-7, 1-8, 1-9, 1-10 or more) amino acid substitutions, deletion, or additions.

In the present application, the term "identity" generally refers to the percent of the number of the same amino acid residues in the number of all the amino acid residues when comparing the candidate sequence with the specific peptide or polypeptide sequence.

In the present application, the term "IgG" generally refers to an immunoglobulin G. IgG is one of the human immunoglobulins, and others include IgA, Ig M, IgD and IgE. IgG is the main antibody component of serum, accounting for about 75% of serum Ig. According to the antigenity difference in the y chain of the IgG molecule, the human IgG has four subtypes: IgG1, IgG2, IgG3, and IgG4. IgG plays an important role in immunity. In the present application, the term "IgG1" generally refers to the subtype with the highest proportion of IgG, which has a higher affinity for Fc receptors.

In the present application, the term "nucleic acid molecule" generally refers to an isolated form of nucleotides, deoxyribonucleotides or ribonucleotides or their analogs of any length isolated from their natural environment or artificially synthesized.

In the present application, the term "vector" generally refers to a nucleic acid molecule capable of self-replication in a suitable host, which transfers the inserted nucleic acid molecule into the host cells and/or between the host cells. The vector may include a vector mainly used for inserting DNA or RNA into cells, a vector mainly used for replicating DNA or RNA, and a vector mainly used for expression of the transcription and/or translation of DNA or RNA. The vector also includes a vector having multiple functions described above. The vector can be a polynucleotide that can be transcribed and translated into a polypeptide when introduced into a suitable host cell. Generally, by culturing a suitable host cell containing the vector, the vector may produce the desired expression product.

In the present application, the term "host cell" generally refers to plasmid or vector which can include or has included the nucleic acid molecule of the present application, or individual cell, cell line or cell culture which can express the antibody or the antigen-binding fragment thereof of the present application. The host cell may include the progeny of a single host cell. Due to natural, accidental and deliberate mutations, the progeny cells cannot be exactly the same as the original parental cells in morphology or genome, as long as they can express the antibody or the antigen-binding fragment thereof of the present application. The host cell may be obtained by transfecting cells in vitro by use of the vector of the present application. The host cell may be prokaryotic cells (e.g., $E.\ Coli$), and can also be eukaryotic cells (e.g., yeast cells, such as, COS cells, Chinese hamster ovary (CHO) cells, HeLa cells, HEK293 cells, COS-1 cells, NS0 cells or myeloma cells). In some embodiments, the host cell is a mammalian cell. For example, the mammalian cell may be CHO-KI cell. In the present application, the term "recombinant host cell" usually refers to a cell to which a recombinant expression vector is introduced. The recombinant host cell not only includes a specific cell, but also includes the progeny of such cells.

In the present application, the term "cancer" generally refers to or describes a physiological status of mammal which is typically characterized in disorders of cell proliferation or survival. Examples of cancers include, but are not limited to, cancer, lymphoma, maternal cell tumor, sarcoma and leukemia and lymphoid malignant tumor. For example, it may be lymphoma.

In the present application, the term "between" generally means that the C-terminus of a certain amino acid fragment is directly or indirectly linked to the N-terminus of the first amino acid fragment, and the N-terminus thereof is directly or indirectly linked to the C-terminus of the second amino acid fragment. In the light chain, for example, the N-terminus of the L-FR2 is directly or indirectly linked to the C-terminus of the LCDR1, and the C-terminus of the L-FR2 is directly or indirectly linked to the N-terminus of the LCDR2. For another example, the N-terminus of the L-FR3 is directly or indirectly linked to the C-terminus of the LCDR2, and the C-terminus of the L-FR3 is directly or indirectly linked to the N-terminus of the LCDR3. In the heavy chain, for example, the N-terminus of the H-FR2 is directly or indirectly linked to the C-terminus of the HCDR1, and the C-terminus of the H-FR2 is directly or indirectly linked to the N-terminus of the HCDR2. For another example, the N-terminus of the H-FR3 is directly or indirectly linked to the C-terminus of the HCDR2, and the C-terminus of the H-FR3 is directly or indirectly linked to the N-terminus of the HCDR3.

In the present application, the term "about" generally refers to a variation in a range of the given value±0.5%-±10%, such as, a variation in a range of the given value±0.5%, ±1%, ±1.5%, ±2%, ±2.5%, ±3%, ±3.5%, ±4%, ±4.5%, ±5%, ±5.5%, ±6%, ±6.5%, ±7%, ±7.5%, ±8%, ±8.5%, ±9%, ±9.5%, or ±10%.

In the present application, the term "includes" generally refers to the meaning of include, sum up, have or contain. In some instances, it is also expressed as a meaning of "be" or "consist of".

Antibody or Antibody Binding Fragment Thereof

In one aspect, the present application provides an antibody or an antigen binding fragment or a variant thereof which binds to a PD-L1 protein with a $K_D$ value of $3\times10^{-9}$ M or less (e.g., the $K_D$ value is not higher than about $3\times10^{-9}$ M, not higher than about $2\times10^{-9}$ M, not higher than about $1\times10^{-9}$ M, not higher than about $9\times10^{-10}$ M, not higher than about $8\times10^{-10}$ M, not higher than about $7\times10^{-10}$ M, not higher than about $6\times10^{-10}$ M, not higher than about $5\times10^{-10}$ M, not higher than about $4\times10^{-10}$ M, not higher than about $3\times10^{-10}$ M, not higher than about $2\times10^{-10}$ M, not higher than $1\times10^{-10}$ M, not higher than about $9\times10^{-11}$ M, not higher than about $8\times10^{-11}$ M, not higher than about $7\times10^{-11}$ M, not higher than about $6\times10^{-11}$ M, not higher than about $1\times10^{-11}$ M or less). For example, the antibody, the antigen binding fragment or the variant thereof may bind to a PD-L1 protein with a $K_D$ value lower than $8\times10^{-11}$ M The antibody or the antigen binding fragment or the variant thereof of the present application may inhibit the binding of PD-L1 to PD-1.

The antibody or the antigen binding fragment or the variant thereof of the present application may relieve or treat tumor-associated diseases. The tumor includes colon cancer.

In the present application, the antibody may be selected from the group consisting of monoclonal antibody, single-strand antibody, chimeric antibody, humanized antibody and fully human antibody.

In the present application, the antigen-binding fragment may be selected from the group consisting of Fab, Fab', F(ab)$_2$ and Fv fragment.

In the present application, the variant may be an amino acid sequence which has substantially the same functions (e.g., can specifically bind to PD-L1) thereto, and has at least 85% or more (e.g., at least about 85%, about 90%, about 91%, about 92%, about 93%, about 94%, about 95%, about 96%, about 97%, about 98%, about 99% or more) of sequence identity. In some embodiments, the variant of the amino acid sequence has basically the same function (e.g., capable of specifically binding to PD-L1), and includes an amino acid sequence obtained by the addition, deletion or substitute of one or more (e.g., 1-2, 1-3, 1-4, 1-5, 1-6, 1-7, 1-8, 1-9, 1-10 or more) amino acids. For another example, the variant of the present application may be selected from the following group: a protein or polypeptide which undergoes substitution, deletion or addition of one or more amino acids in the antibody or the fragment for antigen-binding thereof; and a protein or polypeptide which has more than 85% (e.g., at least about 85%, about 90%, about 91%, about 92%, about 93%, about 94%, about 95%, about 96%, about 97%, about 98%, about 99% or more) sequence identity to the antibody or the fragment for antigen-binding thereof.

In some embodiments, the antibody of the present application may include an antibody light chain or a fragment thereof which includes a LCDR1, and the LCDR1 includes an amino acid sequence shown in SEQ ID NO: 53: TGTX$_1$SX$_2$VGGYX$_3$X$_4$VS; wherein X$_1$ is S, R or V; X$_2$ is D, E or S; X$_3$ is N or R; X$_4$ is Y or E, and wherein the LCDR1 is determined according to the index of the antibody Kabat number. For example, the antibody light chain or the fragment thereof may include LCDR1, and the LCDR1 includes the following amino acid sequence or a variant thereof: SEQ ID NO: 54-58.

In some embodiments, the antibody light chain or the fragment thereof may include LCDR2 including an amino acid sequence shown in SEQ ID NO: 59: X$_1$NSX$_2$RPS, wherein X$_1$ is G or E; X$_2$ is N or I, and wherein the LCDR2 is determined according to the index of the antibody Kabat number. For example, the antibody light chain or the fragment thereof can include LCDR2 including the following amino acid sequence or a variant thereof: SEQ ID NO: 60-61.

In some embodiments, the antibody light chain or the fragment thereof may include LCDR3 including an amino acid sequence shown in SEQ ID NO: 62: QSYDSSLSGX$_1$V, wherein X$_1$ is S or T, and wherein the LCDR3 is determined according to the index of the antibody Kabat number. For example, the antibody light chain or the fragment thereof may include LCDR3 including an amino acid sequence or a variant thereof selected from the group consisting of SEQ ID NO: 63 and SEQ ID NO: 64.

In some embodiments, the antibody light chain or the fragment thereof may further include framework regions L-FRT, L-FR2, L-FR3, and L-FR4. For example, the C-terminus of the L-FR1 can be directly or indirectly linked to the N-terminus of the LCDR1, and the L-FR1 includes an amino acid sequence shown in SEQ ID NO: 71. The L-FR2 is located between the LCDR1 and the LCDR2, and the L-FR2 includes an amino acid sequence shown in SEQ ID NO: 72. The L-FR3 is located between the LCDR2 and the LCDR3, and the L-FR3 includes an amino acid sequence shown in SEQ ID NO: 73-75. The N-terminus of the L-FR4 is directly or indirectly linked to the C-terminus of the LCDR3, and the L-FR4 includes an amino acid sequence shown in SEQ ID NO: 76. In some embodiments, the framework regions are selected from the group consisting of human consensus framework sequences and human germline sequences.

In some embodiments, the light chain or the fragment thereof of the antibody of the present application includes a light chain variable region VL, and the light chain variable region VL includes an amino acid sequence or a variant thereof selected from the group consisting of SEQ ID NO: 4, SEQ ID NO: 11, SEQ ID NO: 33, SEQ ID NO: 37, SEQ ID NO: 39 and SEQ ID NO: 41.

In the antibody or the antigen binding fragment or the variant thereof of the present application, the antibody light chain or a fragment thereof can further include a human constant region, and the human constant region includes a human Igλ constant region.

In the present application, the antibody light chain or the fragment thereof may include an amino acid sequence selected from the group consisting of SEQ ID NO: 8, SEQ ID NO: 15, SEQ ID NO: 34, SEQ ID NO: 38, SEQ ID NO: 40 and SEQ ID NO: 42.

In the present application, the antibody of the present application can include an antibody heavy chain or a fragment thereof, wherein the antibody heavy chain or the fragment thereof may include HCDR1, and the HCDR1 can include an amino acid sequence selected from the group consisting of those shown in SEQ ID NO: 45: X$_1$YAIS, wherein X$_1$ is S or T, and wherein the HCDR1 is determined according to the index of the antibody Kabat number. For example, the antibody heavy chain or the fragment thereof may include HCDR1, and the HCDR1 includes an amino acid sequence or a variant thereof selected from the group consisting of SEQ ID NO: 46 and SEQ ID NO: 47.

In the present application, the antibody heavy chain or the fragment thereof may include HCDR2, and the HCDR2 includes the following amino acid sequence or a variant thereof: SEQ ID NO: 48, and wherein the HCDR2 is determined according to the index of the antibody Kabat number.

In the present application, the antibody heavy chain or the fragment thereof may include HCDR3, and the HCDR3 includes an amino acid sequence selected from the group consisting of those shown in SEQ ID NO: 49: TMX$_1$X$_2$YX$_3$X$_4$GNX$_5$DY, wherein X$_1$ is D, E or G, X$_2$ is G or E, X$_3$ is S or G, X$_4$ is Y or F, X$_5$ is F or Y, and wherein the HCDR3 is determined according to the index of the antibody Kabat number. For example, the antibody heavy chain or the fragment thereof may include HCDR3, and the HCDR3 includes the following amino acid sequence or a variant thereof: SEQ ID NO: 50-52.

In some embodiments, the antibody heavy chain or the fragment thereof further includes framework regions H-FR1, H-FR2, H-FR3, and H-FR4. For example, the C-terminus of H-FR1 is directly or indirectly linked to the N-terminus of HCDR1, and the H-FR1 may include an amino acid sequence selected from the group consisting of SEQ ID NO: 65, SEQ ID NO: 66 and SEQ ID NO: 67. The H-FR2 is located between the HCDR1 and the HCDR2, and the H-FR2 can include an amino acid sequence shown in SEQ ID NO: 68. The H-FR3 is located between the HCDR2 and the HCDR3, and the H-FR3 may include an amino acid sequence shown in SEQ ID NO: 69. The N-terminus of H-FR4 is directly or indirectly linked to the C-terminus of HCDR3, and the H-FR4 may include an amino acid sequence shown in SEQ ID NO: 70. In some embodiments, the framework regions are selected from the group consisting of human consensus framework sequences and human germline sequences.

The antibody heavy chain or the fragment thereof of the present application can include a heavy chain variable region VH, and the heavy chain variable region VH can include an amino acid sequence or a variant thereof selected from the group consisting of SEQ ID NO: 2, SEQ ID NO: 9, SEQ ID NO: 31, and SEQ ID NO: 35. In the antibody, the antigen binding fragment or the variant thereof of the present application, the antibody heavy chain or a fragment thereof may further include a human constant region. For example, the human constant region may include a human IgG constant region. For example, the human IgG constant region may include a human IgG1 constant region.

In some embodiments, the antibody heavy chain or a fragment thereof may include an amino acid sequence or a variant thereof selected from the group consisting of SEQ ID NO: 6, SEQ ID NO: 13, SEQ ID NO: 32, and SEQ ID NO: 36.

In some embodiments, the antibody of the present application includes an antibody light chain or a fragment thereof which includes LCDR1, and the LCDR1 includes an amino acid sequence shown in SEQ ID NO: 53: TGTX$_1$SX$_2$VGGYX$_3$X$_4$VS; wherein X$_1$ is S, R or V; X$_2$ is D, E or S; X$_3$ is N or R; X$_4$ is Y or E, and wherein the LCDR1 is determined according to the index of the antibody Kabat number. For example, the antibody light chain or the fragment thereof may include LCDR1, and the LCDR1 includes an amino acid sequence or a variant thereof selected from the group consisting of SEQ ID NO: 54-58. The antibody light chain or the fragment thereof includes LCDR2 including an amino acid sequence shown in SEQ ID NO: 59: $X_1NSX_2RPS$, wherein $X_1$ is G or E; $X_2$ is N or I, and wherein the LCDR2 is determined according to the index of the antibody Kabat number. For example, the antibody light chain or the fragment thereof can include LCDR2 including an amino acid sequence or a variant thereof selected from the group consisting of SEQ ID NO: 60-61. The antibody light chain or the fragment thereof includes LCDR3 including an amino acid sequence shown in SEQ ID NO: 62: $QSYDSSLSGX_1V$, wherein $X_1$ is S or T, and wherein the LCDR3 is determined according to the index of the antibody Kabat number. For example, the antibody light chain or the fragment thereof may include LCDR3 including an amino acid sequence or a variant thereof selected from the group consisting of SEQ ID NO: 63-64. Moreover, the antibody of the present application includes an antibody heavy chain or a fragment thereof which includes a HCDR1, and the HCDR1 includes an amino acid sequence selected from the group consisting of those shown in SEQ ID NO: 45: $X_1YAIS$, wherein $X_1$ is S or T, and wherein the HCDR1 is determined according to the index of the antibody Kabat number. For example, the antibody heavy chain or the fragment thereof may include HCDR1, and the HCDR1 includes an amino acid sequence or a variant thereof selected from the group consisting of SEQ ID NO: 46 and SEQ ID NO: 47. For example, the antibody heavy chain or the fragment thereof may include HCDR2, and the HCDR2 includes the following amino acid sequence or a variant thereof: SEQ ID NO: 48, and wherein the HCDR2 is determined according to the index of the antibody Kabat number. For another example, the antibody heavy chain or the fragment thereof includes HCDR3, and the HCDR3 includes an amino acid sequence selected from that shown in SEQ ID NO: 49: $TMX_1X_2YX_3X_4GNX_5DY$, wherein $X_1$ is D, E or G, $X_2$ is G or E, $X_3$ is S or G, $X_4$ is Y or F, $X_5$ is F or Y, and wherein the HCDR3 is determined according to the index of the antibody Kabat number. The antibody heavy chain or the fragment thereof may include HCDR3, and the HCDR3 includes the following amino acid sequence or a variant thereof: SEQ ID NO: 50-52.

The amino acid sequence of the LCDR1 of the antibody, the antigen binding fragment or the variant thereof of the present application may include SEQ ID NO: 54 or a variant thereof, the amino acid sequence of the LCDR2 may include SEQ ID NO: 60 or a variant thereof, the amino acid sequence of the LCDR3 may include SEQ ID NO: 63 or a variant thereof, and the amino acid sequence of the HCDR1 may include SEQ ID NO: 46; the amino acid sequence of the HCDR2 may include SEQ ID NO: 48 or a variant thereof, the amino acid sequence of the HCDR3 may include SEQ ID NO: 50 or a variant thereof. For example, the antibody, the antigen binding fragment or the variant thereof may include the antibody YN-002 or an antibody with the same LCDR1-3 and HCDR1-3 therewith. In some cases, the amino acid sequence of the L-FR1 of the antibody, the antigen binding fragment or the variant thereof may include SEQ ID NO: 71 or a variant thereof, the amino acid sequence of the L-FR2 may include SEQ ID NO: 72 or a variant thereof, the amino acid sequence of the L-FR3 may include SEQ ID NO: 73 or a variant thereof, the amino acid sequence of the L-FR4 may include SEQ ID NO: 76 or a variant thereof, and the amino acid sequence of the H-FR1 may include SEQ ID NO: 65 or a variant thereof, the amino acid sequence of the H-FR2 may include SEQ ID NO: 68 or a variant thereof, the amino acid sequence of the H-FR3 may include SEQ ID NO: 69 or a variant thereof, and the amino acid sequence of the H-FR4 may include SEQ ID NO: 70 or a variant thereof. For example, the antibody, the antigen binding fragment or the variant thereof may include an antibody having the same LCDR1-3, HCDR1-3, L-FR1-4 and H-FR1-4 as the antibody YN-002. In some embodiments, the light chain of the antibody, the antigen binding fragment or the variant thereof of the present application may include a light chain variable region, the amino acid sequence of the light chain variable region may include SEQ ID NO: 4 or a variant thereof, and wherein the heavy chain may include a heavy chain variable region, and the amino acid sequence of the heavy chain variable region may include SEQ ID NO: 2 or a variant thereof. For example, the antibody, the antigen binding fragment or the variant thereof may include the antibody YN-002 or an antibody having the same light chain variable region and heavy chain variable region therewith. In some embodiments, the antibody, the antigen binding fragment or the variant thereof of the present application may include a light chain and a heavy chain, the amino acid sequence of the light chain is shown in SEQ ID NO: 8 and the amino acid sequence of the heavy chain is shown in SEQ ID NO: 6. For example, the antibody, the antigen binding fragment or the variant thereof may include the antibody YN-002 or have the same light chain and heavy chain therewith.

In some embodiments, the antibody, the antigen binding fragment or the variant thereof of the present application competes with a reference antibody to bind to PD-L1 protein (e.g., human PD-L1 protein). The reference antibody may include LCDR1-3 and HCDR1-3, and the amino acid sequence of the LCDR1 may include SEQ ID NO: 54 or a variant thereof, the amino acid sequence of the LCDR2 may include SEQ ID NO: 60 or a variant thereof, the amino acid sequence of the LCDR3 may include SEQ ID NO: 63 or a variant thereof, and the amino acid sequence of the HCDR1 may include SEQ ID NO: 46 or a variant thereof, the amino acid sequence of the HCDR2 may include SEQ ID NO: 48 or a variant thereof, the amino acid sequence of the HCDR3 may include SEQ ID NO: 50 or a variant thereof. In some embodiments, the reference antibody can include the antibody YN-002 or an antibody with the same LCDR1-3 and HCDR1-3 therewith. In some embodiments, the reference antibody includes L-FR1-4 and H-FR1-4, and the amino acid sequence of the L-FR1 may include SEQ ID NO: 71 or a variant thereof, the amino acid sequence of the L-FR2 may include SEQ ID NO: 72 or a variant thereof, the amino acid sequence of the L-FR3 may include SEQ ID NO: 73 or a variant thereof, the amino acid sequence of the L-FR4 may include SEQ ID NO: 76 or a variant thereof, and the amino acid sequence of the H-FR1 may include SEQ ID NO: 65 or a variant thereof; the amino acid sequence of the H-FR2 may include SEQ ID NO: 68 or a variant thereof; the amino acid sequence of the H-FR3 may include SEQ ID NO: 69 or a variant thereof; the amino acid sequence of the H-FR4 may include SEQ ID NO: 70 or a variant thereof. For example, the antibody or the antigen-binding fragment thereof may include the antibody YN-002 or an antibody with the same LCDR1-3, HCDR1-3, L-FR1-4 and H-FR1-4 therewith. In some embodiments, the reference antibody can include a light chain variable region and a heavy chain variable region, the amino acid sequence of the light chain variable region may include SEQ ID NO: 4 or a variant thereof; and the amino acid sequence of the heavy chain variable region may include SEQ ID NO: 2 or a variant thereof. For example, the reference antibody may include the antibody YN-002 or an antibody having the same light chain variable region and heavy chain variable region therewith. In some embodiments, the reference antibody may include a light chain and a heavy chain, the amino acid sequence of the light chain may be shown in SEQ ID NO: 8, and the heavy chain amino acid sequence may be shown in SEQ ID NO: 6. For example, the reference antibody may include the antibody YN-002 or have the same light chain and heavy chain therewith.

In some embodiments, the amino acid sequence of the LCDR1 of the antibody, the antigen binding fragment or the variant thereof of the present application may include SEQ ID NO: 54 or a variant thereof; the amino acid sequence of the LCDR2 may include SEQ ID NO: 60 or a variant thereof; the amino acid sequence of the LCDR3 may include SEQ ID NO: 63 or a variant thereof; and the amino acid sequence of the HCDR1 may include SEQ ID NO: 46 or a variant thereof; the amino acid sequence of the HCDR2 can include SEQ ID NO: 48 or a variant thereof; the amino acid sequence of the HCDR3 may include SEQ ID NO: 50 or a variant thereof. For example, the antibody, the antigen binding fragment or the variant thereof can include the antibody YN-003 or an antibody with the same LCDR1-3 and HCDR1-3 therewith. In some cases, the amino acid sequence of the L-FRT of the antibody, the antigen binding fragment or the variant thereof may include SEQ ID NO: 71 or a variant thereof; the amino acid sequence of the L-FR2 may include SEQ ID NO: 72 or a variant thereof; the amino acid sequence of the L-FR3 may include SEQ ID NO: 74 or a variant thereof; the amino acid sequence of the L-FR4 may include SEQ ID NO: 76 or a variant thereof; and the amino acid sequence of the H-FR1 may include SEQ ID NO: 66 or a variant thereof; the amino acid sequence of the H-FR2 may include SEQ ID NO: 68 or a variant thereof; the amino acid sequence of the H-FR3 may include SEQ ID NO: 69 or a variant thereof; and the amino acid sequence of the H-FR4 may include SEQ ID NO: 70 or a variant thereof. For example, the antibody, the antigen binding fragment or the variant thereof may include the antibody YN-003 or an antibody with the same LCDR1-3, HCDR1-3, L-FRT-4 and H-FRT-4 therewith. In some embodiments, the light chain of the antibody, the antigen binding fragment or the variant thereof of the present application may include a light chain variable region, the amino acid sequence of the light chain variable region may include SEQ ID NO: 11 or a variant thereof; and wherein the heavy chain may include a heavy chain variable region, and the amino acid sequence of the heavy chain variable region can include SEQ ID NO: 9 or a variant thereof. For example, the antibody, the antigen binding fragment or the variant thereof may include the antibody YN-003 or an antibody having the same light chain variable region and heavy chain variable region therewith. In some embodiments, the antibody, the antigen binding fragment or the variant thereof of the present application may include a light chain and a heavy chain, the amino acid sequence of the light chain is shown in SEQ ID NO: 15 and the amino acid sequence of the heavy chain is shown in SEQ ID NO: 13. For example, the antibody, the antigen binding fragment or the variant thereof may include the antibody YN-003 or have the same light chain and heavy chain therewith.

In some embodiments, the antibody, the antigen binding fragment or the variant thereof of the present application competes with a reference antibody to bind to PD-L1 protein (e.g., human PD-L1 protein). The reference antibody can include LCDR1-3 and HCDR1-3, and the amino acid sequence of the LCDR1 may include SEQ ID NO: 54 or a variant thereof; the amino acid sequence of the LCDR2 may include SEQ ID NO: 60 or a variant thereof; the amino acid sequence of the LCDR3 may include SEQ ID NO: 63 or a variant thereof; and the amino acid sequence of the HCDR1 may include SEQ ID NO: 46 or a variant thereof; the amino acid sequence of the HCDR2 may include SEQ ID NO: 48 or a variant thereof; the amino acid sequence of the HCDR3 may include SEQ ID NO: 50 or a variant thereof. In some embodiments, the reference antibody can include the antibody YN-003 or an antibody with the same LCDR1-3 and HCDR1-3 therewith. In some embodiments, the reference antibody includes L-FR1-4 and H-FRT-4, and the amino acid sequence of the L-FRT may include SEQ ID NO: 71 or a variant thereof; the amino acid sequence of the L-FR2 may include SEQ ID NO: 72 or a variant thereof; the amino acid sequence of the L-FR3 may include SEQ ID NO: 74 or a variant thereof; the amino acid sequence of the L-FR4 may include SEQ ID NO: 76 or a variant thereof; and the amino acid sequence of the H-FR1 may include SEQ ID NO: 66 or a variant thereof; the amino acid sequence of the H-FR2 may include SEQ ID NO: 68 or a variant thereof; the amino acid sequence of the H-FR3 may include SEQ ID NO: 69 or a variant thereof, the amino acid sequence of the H-FR4 may include SEQ ID NO: 70 or a variant thereof. For example, the antibody or the antigen-binding fragment thereof may include the antibody YN-003 or an antibody with the same LCDR1-3, HCDR1-3, L-FR1-4 and H-FR1-4 therewith. In some embodiments, the reference antibody may include a light chain variable region and a heavy chain variable region, the amino acid sequence of the light chain variable region may include SEQ ID NO: 11 or a variant thereof, and the amino acid sequence of the heavy chain variable region may include SEQ ID NO: 9 or a variant thereof. For example, the reference antibody may include the antibody YN-003 or an antibody having the same light chain variable region and heavy chain variable region therewith. In some embodiments, the reference antibody may include a light chain and a heavy chain, the amino acid sequence of the light chain may be shown in SEQ ID NO: 15 and the heavy chain amino acid sequence may be shown in SEQ ID NO: 13. For example, the reference antibody may include the antibody YN-003 or have the same light chain and heavy chain therewith.

In some embodiments, the amino acid sequence of the LCDR1 of the antibody, the antigen binding fragment or the variant thereof of the present application may include SEQ ID NO: 55 or a variant thereof, the amino acid sequence of the LCDR2 may include SEQ ID NO: 60 or a variant thereof, the amino acid sequence of the LCDR3 may include SEQ ID NO: 64 or a variant thereof, and the amino acid sequence of the HCDR1 may include SEQ ID NO: 47 or a variant thereof, the amino acid sequence of the HCDR2 may include SEQ ID NO: 48 or a variant thereof, the amino acid sequence of the HCDR3 may include SEQ ID NO: 51 or a variant thereof. For example, the antibody, the antigen binding fragment or the variant thereof may include the antibody YN-035 or an antibody with the same LCDR1-3 and HCDR1-3 therewith. In some cases, the amino acid sequence of the L-FR1 of the antibody, the antigen binding fragment or the variant thereof may include SEQ ID NO: 71 or a variant thereof, the amino acid sequence of the L-FR2 may include SEQ ID NO: 72 or a variant thereof, the amino acid sequence of the L-FR3 may include SEQ ID NO: 74 or a variant thereof, the amino acid sequence of the L-FR4 may include SEQ ID NO: 76 or a variant thereof, and the amino acid sequence of the H-FR1 may include SEQ ID NO: 67 or a variant thereof, the amino acid sequence of the H-FR2 may include SEQ ID NO: 68 or a variant thereof, the amino acid sequence of the H-FR3 may include SEQ ID NO: 69 or a variant thereof, and the amino acid sequence of the H-FR4 may include SEQ ID NO: 70 or a variant thereof. For example, the antibody, the antigen binding fragment or the variant thereof may include the antibody YN-035 or an antibody with the same LCDR1-3, HCDR1-3, L-FR1-4 and H-FR1-4 therewith. In some embodiments, the light chain of the antibody, the antigen binding fragment or the variant thereof of the present application may include a light chain variable region, the amino acid sequence of the light chain variable region may include SEQ ID NO: 33 or a variant thereof; and wherein the heavy chain may include a heavy chain variable region, and the amino acid sequence of the heavy chain variable region may include SEQ ID NO: 31 or a variant thereof. For example, the antibody, the antigen binding fragment or the variant thereof may include the antibody YN-035 or an antibody having the same light chain variable region and heavy chain variable region therewith. In some embodiments, the antibody, the antigen binding fragment or the variant thereof of the present application may include a light chain and a heavy chain, the amino acid sequence of the light chain is shown in SEQ ID NO: 34 and the amino acid sequence of the heavy chain is shown in SEQ ID NO: 32. For example, the antibody, the antigen binding fragment or the variant thereof may include the antibody YN-035 or have the same light chain and heavy chain therewith.

In some embodiments, the antibody, the antigen binding fragment or the variant thereof of the present application competes with a reference antibody to bind to PD-L1 protein (e.g., human PD-L1 protein). The reference antibody may include LCDR1-3 and HCDR1-3, and the amino acid sequence of the LCDR1 may include SEQ ID NO: 55 or a variant thereof; the amino acid sequence of the LCDR2 may include SEQ ID NO: 60 or a variant thereof; the amino acid sequence of the LCDR3 may include SEQ ID NO: 64 or a variant thereof; and the amino acid sequence of the HCDR1 may include SEQ ID NO: 47 or a variant thereof; the amino acid sequence of the HCDR2 may include SEQ ID NO: 48 or a variant thereof; the amino acid sequence of the HCDR3 may include SEQ ID NO: 51 or a variant thereof. In some embodiments, the reference antibody may include the antibody YN-035 or an antibody with the same LCDR1-3 and HCDR1-3 therewith. In some embodiments, the reference antibody includes L-FR1-4 and H-FR1-4, and the amino acid sequence of the L-FR1 may include SEQ ID NO: 71 or a variant thereof; the amino acid sequence of the L-FR2 may include SEQ ID NO: 72 or a variant thereof; the amino acid sequence of the L-FR3 may include SEQ ID NO: 74 or a variant thereof; the amino acid sequence of the L-FR4 may include SEQ ID NO: 76 or a variant thereof; and the amino acid sequence of the H-FR1 may include SEQ ID NO: 67 or a variant thereof; the amino acid sequence of the H-FR2 may include SEQ ID NO: 68 or a variant thereof; the amino acid sequence of the H-FR3 may include SEQ ID NO: 69 or a variant thereof; the amino acid sequence of the H-FR4 may include SEQ ID NO: 70 or a variant thereof. For example, the antibody or the antigen-binding fragment thereof may include the antibody YN-035 or an antibody with the same LCDR1-3, HCDR1-3, L-FR1-4 and H-FR1-4 therewith. In some embodiments, the reference antibody may include a light chain variable region and a heavy chain variable region, the amino acid sequence of the light chain variable region may include SEQ ID NO: 33 or a variant thereof, and the amino acid sequence of the heavy chain variable region may include SEQ ID NO: 31 or a variant thereof. For example, the reference antibody may include the antibody YN-035 or an antibody having the same light chain variable region and heavy chain variable region therewith. In some embodiments, the reference antibody can include a light chain and a heavy chain, the amino acid sequence of the light chain may be shown in SEQ ID NO: 34 and the heavy chain amino acid sequence may be shown in SEQ ID NO: 32. For example, the reference antibody may include the antibody YN-035 or have the same light chain and heavy chain therewith.

In some embodiments, the amino acid sequence of the LCDR1 of the antibody, the antigen binding fragment or the variant thereof of the present application may include SEQ ID NO: 55 or a variant thereof, the amino acid sequence of the LCDR2 may include SEQ ID NO: 60 or a variant thereof, the amino acid sequence of the LCDR3 may include SEQ ID NO: 64 or a variant thereof, and the amino acid sequence of the HCDR1 may include SEQ ID NO: 47 or a variant thereof, the amino acid sequence of the HCDR2 may include SEQ ID NO: 48 or a variant thereof, the amino acid sequence of the HCDR3 may include SEQ ID NO: 52 or a variant thereof. For example, the antibody, the antigen binding fragment or the variant thereof may include the antibody YN-036 or an antibody with the same LCDR1-3 and HCDR1-3 therewith. In some cases, the amino acid sequence of the L-FR1 of the antibody, the antigen binding fragment or the variant thereof may include SEQ ID NO: 71 or a variant thereof, the amino acid sequence of the L-FR2 may include SEQ ID NO: 72 or a variant thereof, the amino acid sequence of the L-FR3 may include SEQ ID NO: 74 or a variant thereof, the amino acid sequence of the L-FR4 may include SEQ ID NO: 76 or a variant thereof, and the amino acid sequence of the H-FR1 may include SEQ ID NO: 67 or a variant thereof, the amino acid sequence of the H-FR2 may include SEQ ID NO: 68 or a variant thereof, the amino acid sequence of the H-FR3 may include SEQ ID NO: 69 or a variant thereof, and the amino acid sequence of the H-FR4 may include SEQ ID NO: 70 or a variant thereof. For example, the antibody, the antigen binding fragment or the variant thereof may include the antibody YN-036 or an antibody with the same LCDR1-3, HCDR1-3, L-FR1-4 and H-FR1-4 therewith. In some embodiments, the light chain of the antibody, the antigen binding fragment or the variant thereof of the present application may include a light chain variable region, the amino acid sequence of the light chain variable region may include SEQ ID NO: 33 or a variant thereof; and wherein the heavy chain may include a heavy chain variable region, and the amino acid sequence of the heavy chain variable region may include SEQ ID NO: 35 or a variant thereof. For example, the antibody, the antigen binding fragment or the variant thereof may include the antibody YN-036 or an antibody having the same light chain variable region and heavy chain variable region therewith. In some embodiments, the antibody, the antigen binding fragment or the variant thereof of the present application may include a light chain and a heavy chain, the amino acid sequence of the light chain is shown in SEQ ID NO: 34 and the amino acid sequence of the heavy chain is shown in SEQ ID NO: 36. For example, the antibody, the antigen binding fragment or the variant thereof may include the antibody YN-036 or have the same light chain and heavy chain therewith.

In some embodiments, the antibody, the antigen binding fragment or the variant thereof of the present application competes with a reference antibody to bind to PD-L1 protein (e.g., human PD-L1 protein). The reference antibody may include LCDR1-3 and HCDR1-3, and the amino acid sequence of the LCDR1 may include SEQ ID NO: 55 or a variant thereof; the amino acid sequence of the LCDR2 may include SEQ ID NO: 60 or a variant thereof; the amino acid sequence of the LCDR3 may include SEQ ID NO: 64 or a variant thereof; and the amino acid sequence of the HCDR1 may include SEQ ID NO: 47 or a variant thereof; the amino acid sequence of the HCDR2 may include SEQ ID NO: 48 or a variant thereof; and the amino acid sequence of the HCDR3 may include SEQ ID NO: 52 or a variant thereof. In some embodiments, the reference antibody may include the antibody YN-036 or an antibody with the same LCDR1-3 and HCDR1-3 therewith. In some embodiments, the reference antibody includes L-FR1-4 and H-FRT-4, and the amino acid sequence of the L-FRT may include SEQ ID NO: 71 or a variant thereof; the amino acid sequence of the L-FR2 may include SEQ ID NO: 72 or a variant thereof; the amino acid sequence of the L-FR3 may include SEQ ID NO: 74 or a variant thereof; the amino acid sequence of the L-FR4 may include SEQ ID NO: 76 or a variant thereof; and the amino acid sequence of the H-FR1 may include SEQ ID NO: 67 or a variant thereof; the amino acid sequence of the H-FR2 may include SEQ ID NO: 68 or a variant thereof; the amino acid sequence of the H-FR3 may include SEQ ID NO: 69 or a variant thereof; the amino acid sequence of the H-FR4 may include SEQ ID NO: 70 or a variant thereof. For example, the antibody or the antigen-binding fragment thereof may include the antibody YN-036 or an antibody with the same LCDR1-3, HCDR1-3, L-FR1-4 and H-FR1-4 therewith. In some embodiments, the reference antibody may include a light chain variable region and a heavy chain variable region, the amino acid sequence of the light chain variable region may include SEQ ID NO: 33 or a variant thereof, and the amino acid sequence of the heavy chain variable region may include SEQ ID NO: 35 or a variant thereof. For example, the reference antibody may include the antibody YN-036 or an antibody having the same light chain variable region and heavy chain variable region therewith. In some embodiments, the reference antibody may include a light chain and a heavy chain, the amino acid sequence of the light chain may be shown in SEQ ID NO: 34 and the heavy chain amino acid sequence may be shown in SEQ ID NO: 36. For example, the reference antibody may include the antibody YN-036 or have the same light chain and heavy chain therewith.

In some embodiments, the amino acid sequence of the LCDR1 of the antibody, the antigen binding fragment or the variant thereof of the present application may include SEQ ID NO: 56 or a variant thereof, the amino acid sequence of the LCDR2 may include SEQ ID NO: 61 or a variant thereof, the amino acid sequence of the LCDR3 may include SEQ ID NO: 64 or a variant thereof, and the amino acid sequence of the HCDR1 may include SEQ ID NO: 47 or a variant thereof, the amino acid sequence of the HCDR2 may include SEQ ID NO: 48 or a variant thereof, and the amino acid sequence of the HCDR3 may include SEQ ID NO: 52 or a variant thereof. For example, the antibody, the antigen binding fragment or the variant thereof may include the antibody YN-037 or an antibody with the same LCDR1-3 and HCDR1-3 therewith. In some cases, the amino acid sequence of the L-FR1 of the antibody, the antigen binding fragment or the variant thereof may include SEQ ID NO: 71 or a variant thereof, the amino acid sequence of the L-FR2 may include SEQ ID NO: 72 or a variant thereof, the amino acid sequence of the L-FR3 may include SEQ ID NO: 75 or a variant thereof, the amino acid sequence of the L-FR4 may include SEQ ID NO: 76 or a variant thereof, and the amino acid sequence of the H-FR1 may include SEQ ID NO: 67 or a variant thereof, the amino acid sequence of the H-FR2 may include SEQ ID NO: 68 or a variant thereof, the amino acid sequence of the H-FR3 may include SEQ ID NO: 69 or a variant thereof, and the amino acid sequence of the H-FR4 may include SEQ ID NO: 70 or a variant thereof. For example, the antibody, the antigen binding fragment or the variant thereof may include the antibody YN-037 or an antibody with the same LCDR1-3, HCDR1-3, L-FR1-4 and H-FR1-4 therewith. In some embodiments, the light chain of the antibody, the antigen binding fragment or the variant thereof of the present application may include a light chain variable region, the amino acid sequence of the light chain variable region may include SEQ ID NO: 37 or a variant thereof; and wherein the heavy chain may include a heavy chain variable region, and the amino acid sequence of the heavy chain variable region may include SEQ ID NO: 35 or a variant thereof. For example, the antibody, the antigen binding fragment or the variant thereof may include the antibody YN-037 or an antibody having the same light chain variable region and heavy chain variable region therewith. In some embodiments, the antibody, the antigen binding fragment or the variant thereof of the present application may include a light chain and a heavy chain, the amino acid sequence of the light chain is shown in SEQ ID NO: 38 and the amino acid sequence of the heavy chain is shown in SEQ ID NO: 36. For example, the antibody, the antigen binding fragment or the variant thereof may include the antibody YN-037 or have the same light chain and heavy chain therewith.

In some embodiments, the antibody, the antigen binding fragment or the variant thereof of the present application competes with a reference antibody to bind to PD-L1 protein (e.g., human PD-L1 protein). The reference antibody may include LCDR1-3 and HCDR1-3, and the amino acid sequence of the LCDR1 may include SEQ ID NO: 56 or a variant thereof; the amino acid sequence of the LCDR2 may include SEQ ID NO: 61 or a variant thereof; the amino acid sequence of the LCDR3 may include SEQ ID NO: 64 or a variant thereof; and the amino acid sequence of the HCDR1 may include SEQ ID NO: 47 or a variant thereof; the amino acid sequence of the HCDR2 may include SEQ ID NO: 48 or a variant thereof; and the amino acid sequence of the HCDR3 may include SEQ ID NO: 52 or a variant thereof. In some embodiments, the reference antibody can include the antibody YN-037 or an antibody with the same LCDR1-3 and HCDR1-3 therewith. In some embodiments, the reference antibody includes L-FR1-4 and H-FRT-4, and the amino acid sequence of the L-FRT may include SEQ ID NO: 71 or a variant thereof; the amino acid sequence of the L-FR2 may include SEQ ID NO: 72 or a variant thereof; the amino acid sequence of the L-FR3 may include SEQ ID NO: 75 or a variant thereof; the amino acid sequence of the L-FR4 may include SEQ ID NO: 76 or a variant thereof; and the amino acid sequence of the H-FR1 may include SEQ ID NO: 67 or a variant thereof; the amino acid sequence of the H-FR2 may include SEQ ID NO: 68 or a variant thereof; the amino acid sequence of the H-FR3 may include SEQ ID NO: 69 or a variant thereof; and the amino acid sequence of the H-FR4 may include SEQ ID NO: 70 or a variant thereof. For example, the antibody or the antigen-binding fragment thereof may include the antibody YN-037 or an antibody with the same LCDR1-3, HCDR1-3, L-FR1-4 and H-FRT-4 therewith. In some embodiments, the reference antibody may include a light chain variable region and a heavy chain variable region, the amino acid sequence of the light chain variable region may include SEQ ID NO: 37 or a variant thereof; and the amino acid sequence of the heavy chain variable region may include SEQ ID NO: 35 or a variant thereof. For example, the reference antibody may include the antibody YN-037 or an antibody having the same light chain variable region and heavy chain variable region therewith. In some embodiments, the reference antibody may include a light chain and a heavy chain, the amino acid sequence of the light chain may be shown in SEQ ID NO: 38 and the heavy chain amino acid sequence may be shown in SEQ ID NO: 36. For example, the reference antibody may include the antibody YN-037 or have the same light chain and heavy chain therewith.

In some embodiments, the amino acid sequence of the LCDR1 of the antibody, the antigen binding fragment or the variant thereof of the present application may include SEQ ID NO: 57 or a variant thereof; the amino acid sequence of the LCDR2 may include SEQ ID NO: 61 or a variant thereof; the amino acid sequence of the LCDR3 may include SEQ ID NO: 64 or a variant thereof; and the amino acid sequence of the HCDR1 may include SEQ ID NO: 47 or a variant thereof; the amino acid sequence of the HCDR2 may include SEQ ID NO: 48 or a variant thereof; and the amino acid sequence of the HCDR3 may include SEQ ID NO: 52 or a variant thereof. For example, the antibody, the antigen binding fragment or the variant thereof can include the antibody YN-038 or an antibody with the same LCDR1-3 and HCDR1-3 therewith. In some cases, the amino acid sequence of the L-FRT of the antibody, the antigen binding fragment or the variant thereof may include SEQ ID NO: 71 or a variant thereof; the amino acid sequence of the L-FR2 may include SEQ ID NO: 72 or a variant thereof; the amino acid sequence of the L-FR3 may include SEQ ID NO: 75 or a variant thereof; the amino acid sequence of the L-FR4 may include SEQ ID NO: 76 or a variant thereof; and the amino acid sequence of the H-FR1 may include SEQ ID NO: 67 or a variant thereof; the amino acid sequence of the H-FR2 may include SEQ ID NO: 68 or a variant thereof; the amino acid sequence of the H-FR3 may include SEQ ID NO: 69 or a variant thereof; and the amino acid sequence of the H-FR4 may include SEQ ID NO: 70 or a variant thereof. For example, the antibody, the antigen binding fragment or the variant thereof can include the antibody YN-038 or an antibody with the same LCDR1-3, HCDR1-3, L-FRT-4 and H-FRT-4 therewith. In some embodiments, the light chain of the antibody, the antigen binding fragment or the variant thereof of the present application may include a light chain variable region, the amino acid sequence of the light chain variable region may include SEQ ID NO: 39 or a variant thereof, and wherein the heavy chain may include a heavy chain variable region, and the amino acid sequence of the heavy chain variable region may include SEQ ID NO: 35 or a variant thereof. For example, the antibody, the antigen binding fragment or the variant thereof may include the antibody YN-038 or an antibody having the same light chain variable region and heavy chain variable region therewith. In some embodiments, the antibody, the antigen binding fragment or the variant thereof of the present application may include a light chain and a heavy chain, the amino acid sequence of the light chain is shown in SEQ ID NO: 40 and the amino acid sequence of the heavy chain is shown in SEQ ID NO: 36. For example, the antibody, the antigen binding fragment or the variant thereof may include the antibody YN-038 or have the same light chain and heavy chain therewith.

In some embodiments, the antibody, the antigen binding fragment or the variant thereof of the present application competes with a reference antibody to bind to PD-L1 protein (e.g., human PD-L1 protein). The reference antibody may include LCDR1-3 and HCDR1-3, and the amino acid sequence of the LCDR1 may include SEQ ID NO: 57 or a variant thereof, the amino acid sequence of the LCDR2 may include SEQ ID NO: 61 or a variant thereof, the amino acid sequence of the LCDR3 may include SEQ ID NO: 64 or a variant thereof, and the amino acid sequence of the HCDR1 may include SEQ ID NO: 47 or a variant thereof, the amino acid sequence of the HCDR2 may include SEQ ID NO: 48 or a variant thereof, and the amino acid sequence of the HCDR3 may include SEQ ID NO: 52 or a variant thereof. In some embodiments, the reference antibody can include the antibody YN-038 or an antibody with the same LCDR1-3 and HCDR1-3 therewith. In some embodiments, the reference antibody includes L-FR1-4 and H-FR1-4, and the amino acid sequence of the L-FR1 may include SEQ ID NO: 71 or a variant thereof, the amino acid sequence of the L-FR2 may include SEQ ID NO: 72 or a variant thereof, the amino acid sequence of the L-FR3 may include SEQ ID NO: 75 or a variant thereof, the amino acid sequence of the L-FR4 may include SEQ ID NO: 76 or a variant thereof, and the amino acid sequence of the H-FR1 may include SEQ ID NO: 67 or a variant thereof; the amino acid sequence of the H-FR2 may include SEQ ID NO: 68 or a variant thereof, the amino acid sequence of the H-FR3 may include SEQ ID NO: 69 or a variant thereof, and the amino acid sequence of the H-FR4 may include SEQ ID NO: 70 or a variant thereof. For example, the antibody or the antigen-binding fragment thereof can include the antibody YN-038 or an antibody with the same LCDR1-3, HCDR1-3, L-FR1-4 and H-FR1-4 therewith. In some embodiments, the reference antibody may include a light chain variable region and a heavy chain variable region, the amino acid sequence of the light chain variable region may include SEQ ID NO: 39 or a variant thereof; and the amino acid sequence of the heavy chain variable region may include SEQ ID NO: 35 or a variant thereof. For example, the reference antibody can include the antibody YN-038 or an antibody having the same light chain variable region and heavy chain variable region therewith. In some embodiments, the reference antibody may include a light chain and a heavy chain, the amino acid sequence of the light chain may be shown in SEQ ID NO: 40 and the heavy chain amino acid sequence may be shown in SEQ ID NO: 36. For example, the reference antibody can include the antibody YN-038 or have the same light chain and heavy chain therewith.

In some embodiments, the amino acid sequence of the LCDR1 of the antibody, the antigen binding fragment or the variant thereof of the present application may include SEQ ID NO: 58 or a variant thereof; the amino acid sequence of the LCDR2 may include SEQ ID NO: 61 or a variant thereof; the amino acid sequence of the LCDR3 may include SEQ ID NO: 64 or a variant thereof; and the amino acid sequence of the HCDR1 may include SEQ ID NO: 47 or a variant thereof; the amino acid sequence of the HCDR2 may include SEQ ID NO: 48 or a variant thereof; and the amino acid sequence of the HCDR3 may include SEQ ID NO: 52 or a variant thereof. For example, the antibody, the antigen binding fragment or the variant thereof may include the antibody YN-039 or an antibody with the same LCDR1-3 and HCDR1-3 therewith. In some cases, the amino acid sequence of the L-FRT of the antibody, the antigen binding fragment or the variant thereof may include SEQ ID NO: 71 or a variant thereof; the amino acid sequence of the L-FR2 may include SEQ ID NO: 72 or a variant thereof; the amino acid sequence of the L-FR3 may include SEQ ID NO: 75 or a variant thereof; the amino acid sequence of the L-FR4 may include SEQ ID NO: 76 or a variant thereof; and the amino acid sequence of the H-FR1 may include SEQ ID NO: 67 or a variant thereof; the amino acid sequence of the H-FR2 may include SEQ ID NO: 68 or a variant thereof; the amino acid sequence of the H-FR3 may include SEQ ID NO: 69 or a variant thereof; and the amino acid sequence of the H-FR4 may include SEQ ID NO: 70 or a variant thereof. For example, the antibody, the antigen binding fragment or the variant thereof may include the antibody YN-039 or an antibody with the same LCDR1-3, HCDR1-3, L-FRT-4 and H-FRT-4 therewith. In some embodiments, the light chain of the antibody, the antigen binding fragment or the variant thereof of the present application may include a light chain variable region, the amino acid sequence of the light chain variable region may include SEQ ID NO: 41 or a variant thereof; and wherein the heavy chain may include a heavy chain variable region, and the amino acid sequence of the heavy chain variable region may include SEQ ID NO: 35 or a variant thereof. For example, the antibody, the antigen binding fragment or the variant thereof may include the antibody YN-039 or an antibody having the same light chain variable region and heavy chain variable region therewith. In some embodiments, the antibody, the antigen binding fragment or the variant thereof of the present application may include a light chain and a heavy chain, the amino acid sequence of the light chain is shown in SEQ ID NO: 42 and the amino acid sequence of the heavy chain is shown in SEQ ID NO: 36. For example, the antibody, the antigen binding fragment or the variant thereof may include the antibody YN-039 or have the same light chain and heavy chain therewith.

In some embodiments, the antibody, the antigen binding fragment or the variant thereof of the present application competes with a reference antibody to bind to PD-L1 protein (e.g., human PD-L1 protein). The reference antibody may include LCDR1-3 and HCDR1-3, and the amino acid sequence of the LCDR1 may include SEQ ID NO: 58 or a variant thereof; the amino acid sequence of the LCDR2 may include SEQ ID NO: 61 or a variant thereof; the amino acid sequence of the LCDR3 may include SEQ ID NO: 64 or a variant thereof; and the amino acid sequence of the HCDR1 may include SEQ ID NO: 47 or a variant thereof; the amino acid sequence of the HCDR2 may include SEQ ID NO: 48 or a variant thereof; and the amino acid sequence of the HCDR3 may include SEQ ID NO: 52 or a variant thereof. In some embodiments, the reference antibody may include the antibody YN-039 or an antibody with the same LCDR1-3 and HCDR1-3 therewith. In some embodiments, the reference antibody includes L-FR1-4 and H-FRT-4, and the amino acid sequence of the L-FRT may include SEQ ID NO: 71 or a variant thereof; the amino acid sequence of the L-FR2 may include SEQ ID NO: 72 or a variant thereof; the amino acid sequence of the L-FR3 may include SEQ ID NO: 75 or a variant thereof; the amino acid sequence of the L-FR4 may include SEQ ID NO: 76 or a variant thereof; and the amino acid sequence of the H-FR1 may include SEQ ID NO: 67 or a variant thereof; the amino acid sequence of the H-FR2 may include SEQ ID NO: 68 or a variant thereof; the amino acid sequence of the H-FR3 may include SEQ ID NO: 69 or a variant thereof; and the amino acid sequence of the H-FR4 may include SEQ ID NO: 70 or a variant thereof. For example, the antibody or an antigen-binding fragment thereof may include the antibody YN-039 or an antibody with the same LCDR1-3, HCDR1-3, L-FR1-4 and H-FR1-4 therewith. In some embodiments, the reference antibody may include a light chain variable region and a heavy chain variable region, the amino acid sequence of the light chain variable region may include SEQ ID NO: 41 or a variant thereof; and the amino acid sequence of the heavy chain variable region may include SEQ ID NO: 35 or a variant thereof. For example, the reference antibody may include the antibody YN-039 or an antibody having the same light chain variable region and heavy chain variable region therewith. In some embodiments, the reference antibody may include a light chain and a heavy chain, the amino acid sequence of the light chain may be shown in SEQ ID NO: 42 and the heavy chain amino acid sequence may be shown in SEQ ID NO: 36. For example, the reference antibody may include the antibody YN-039 or have the same light chain and heavy chain therewith.

In the present application, the PD-L1 protein is selected from the group consisting of human PD-L1 protein, monkey PD-L1 protein and murine PD-L1 protein.

In another aspect, the present application further provides an antibody, an antigen binding fragment or a variant thereof which binds to a CD137 protein with a $K_D$ of lower than $5\times10^{-9}$ M (e.g., a $K_D$ of not higher than about $5\times10^{-9}$ M, not higher than about $4\times10^{-9}$ M, not higher than about $3\times10^{-9}$ M, not higher than about $2\times10^{-9}$ M, not higher than about $1\times10^{-9}$ M or not higher than about $1\times10^{-10}$M or less). For example, it binds to a CD137 protein with a $K_D$ of lower than $3\times10^{-9}$ M.

The antibody, the antigen binding fragment or the variant thereof of the present application may relieve or treat tumors. For example, the tumor may include colon cancer.

In the present application, the antibody may be selected from the group consisting of monoclonal antibody, single-strand antibody, chimeric antibody, humanized antibody and fully human antibody.

In the present application, the antigen-binding fragment may be selected from the group consisting of Fab, Fab', F(ab)$_2$ and Fv fragment.

In the present application, the variant may be an amino acid sequence which has substantially the same function (e.g., a capacity of specifically binding to the CD137), and has at least 85% or more (e.g., at least about 85%, about 90%, about 91%, about 92%, about 93%, about 94%, about 95%, about 96%, about 97%, about 98%, about 99% or more) sequence identity thereto. In some embodiments, the variant of the amino acid sequence is an amino acid sequence which has substantially the same function (e.g., a capacity of specifically binding to CD137), and on the basis further includes the addition, deletion or substitution of one or more (e.g., 1-2, 1-3, 1-4, 1-5, 1-6, 1-7, 1-8, 1-9, 1-10 or more) amino acids.

In some embodiments, the antibody may include an antibody light chain or a fragment thereof. For example, the antibody light chain or the fragment thereof may include LCDR1, and the LCDR1 may include the following amino acid sequence or a variant thereof: SEQ ID NO: 80. For example, the antibody light chain or the fragment thereof can include LCDR2 including the following amino acid sequence or a variant thereof: SEQ ID NO: 81. For another example, the antibody light chain or the fragment thereof includes LCDR3 or a variant thereof, and the LCDR3 can include an amino acid sequence shown in SEQ ID NO: 82.

In some embodiments, as to the antibody, the antigen binding fragment or the variant thereof, the antibody light chain or the fragment thereof further includes framework regions L-FR1, L-FR2, L-FR3 and L-FR4. For example, the C-terminus of the L-FR1 is directly or indirectly linked to the N-terminus of the LCDR1, and the L-FR1 can include an amino acid sequence shown in SEQ ID NO: 89. The L-FR2 is located between the LCDR1 and the LCDR2, and the L-FR2 may include an amino acid sequence shown in SEQ ID NO: 90. The L-FR3 is located between the LCDR2 and the LCDR3, and the L-FR3 may include an amino acid sequence shown in SEQ ID NO: 91. The N-terminus of the L-FR4 is directly or indirectly linked to the C-terminus of the LCDR3, and the L-FR4 may include an amino acid sequence shown in SEQ ID NO: 92.

In some embodiments, as to the antibody, the antigen binding fragment or the variant thereof, the antibody light chain or a fragment thereof includes a light chain variable region VL, and the light chain variable region VL may include the following amino acid sequence or a variant thereof: SEQ ID NO: 20.

In the present application, the antibody light chain or a fragment thereof may further include a human constant region, and the human constant region includes a human Igλ constant region.

In the present application, the light chain or the fragment thereof of the antibody may include an amino acid sequence shown in SEQ ID NO: 23.

In some embodiments, the antibody may include an antibody heavy chain or a fragment thereof. The antibody heavy chain or the fragment thereof includes HCDR1, and the HCDR1 may include the following amino acid sequence or a variant thereof: SEQ ID NO: 77. The antibody heavy chain or the fragment thereof includes HCDR2, and the HCDR2 may include the following amino acid sequence or a variant thereof: SEQ ID NO: 78. The antibody heavy chain or the fragment thereof includes HCDR3, and the HCDR3 may include the following amino acid sequence or a variant thereof: SEQ ID NO: 79.

In some embodiments, the antibody heavy chain or the fragment thereof may further include framework regions H-FR1, H-FR2, H-FR3 and H-FR4. The C-terminus of H-FR1 is directly or indirectly linked to the N-terminus of HCDR1, and the H-FR1 may include an amino acid sequence shown in SEQ ID NO: 84-85. The H-FR2 is located between the HCDR1 and the HCDR2, and the H-FR2 may include an amino acid sequence shown in SEQ ID NO: 86. The H-FR3 is located between the HCDR2 and the HCDR3, and the H-FR3 may include an amino acid sequence shown in SEQ ID NO: 87. The N-terminus of H-FR4 is directly or indirectly linked to the C-terminus of HCDR3, and the H-FR4 may include an amino acid sequence shown in SEQ ID NO: 88.

The antibody heavy chain or the fragment thereof of the present application includes a heavy chain variable region VH, and the heavy chain variable region VH may include an amino acid sequence or a variant thereof selected from the group consisting of SEQ ID NO: 18 or SEQ ID NO: 25.

In the antibody, the antigen binding fragment or the variant thereof of the present application, the antibody heavy chain or the fragment thereof may further include a human constant region. For example, the human constant region may include a human IgG constant region. For example, the human IgG constant region may include a human IgG1 constant region.

In the present application, the antibody heavy chain or the fragment thereof may include an amino acid sequence or a variant thereof selected from the group consisting of SEQ ID NO: 21 or SEQ ID NO: 27.

In some embodiments, the amino acid sequence of the LCDR1 of the antibody, the antigen binding fragment or the variant thereof of the present application may include SEQ ID NO: 80 or a variant thereof; the amino acid sequence of the LCDR2 may include SEQ ID NO: 81 or a variant thereof; the amino acid sequence of the LCDR3 may include SEQ ID NO: 82 or a variant thereof; and the amino acid sequence of the HCDR1 may include SEQ ID NO: 77 or a variant thereof; the amino acid sequence of the HCDR2 may include SEQ ID NO: 78 or a variant thereof, and the amino acid sequence of the HCDR3 may include SEQ ID NO: 79 or a variant thereof. For example, the antibody, the antigen binding fragment or the variant thereof may include the antibody YN-005 or an antibody with the same LCDR1-3 and HCDR1-3 therewith. In some embodiments, the amino acid sequence of the light chain variable region of the antibody, the antigen binding fragment or the variant thereof of the present application may include SEQ ID NO: 20 or a variant thereof, and the amino acid sequence of the heavy chain variable region may include SEQ ID NO: 18 or a variant thereof. For example, the antibody, the antigen binding fragment or the variant thereof can include the antibody YN-005 or an antibody having the same light chain variable region and heavy chain variable region therewith. In some embodiments, the antibody, the antigen binding fragment or the variant thereof of the present application may include a light chain and a heavy chain, the amino acid sequence of the light chain may be shown in SEQ ID NO: 23 and the heavy chain amino acid sequence may be shown in SEQ ID NO: 21. For example, the antibody, the antigen binding fragment or the variant thereof may include the antibody YN-005 or have the same light chain and heavy chain therewith.

In some embodiments, the antibody, the antigen binding fragment or the variant thereof of the present application competes with a reference antibody to bind to CD137 protein (e.g., human CD137 protein). The reference antibody may include LCDR1-3 and HCDR1-3, and the amino acid sequence of the LCDR1 may include SEQ ID NO: 80 or a variant thereof, the amino acid sequence of the LCDR2 may include SEQ ID NO: 81 or a variant thereof, the amino acid sequence of the LCDR3 may include SEQ ID NO: 82 or a variant thereof, and the amino acid sequence of the HCDR1 may include SEQ ID NO: 77 or a variant thereof, the amino acid sequence of the HCDR2 may include SEQ ID NO: 78 or a variant thereof, and the amino acid sequence of the HCDR3 may include SEQ ID NO: 79 or a variant thereof. In some embodiments, the reference antibody may include the antibody YN-005 or an antibody with the same LCDR1-3 and HCDR1-3 therewith. In some embodiments, the reference antibody may include a light chain variable region and a heavy chain variable region, the amino acid sequence of the light chain variable region may include SEQ ID NO: 20 or a variant thereof, and the amino acid sequence of the heavy chain variable region may include SEQ ID NO: 18 or a variant thereof. For example, the reference antibody may include the antibody YN-005 or an antibody having the same light chain variable region and heavy chain variable region therewith. In some embodiments, the reference antibody may include a light chain and a heavy chain, the amino acid sequence of the light chain may be shown in SEQ ID NO: 23 and the amino acid sequence of the heavy chain may be shown in SEQ ID NO: 21. For example, the reference antibody may include the antibody YN-005 or have the same light chain and heavy chain therewith.

In some embodiments, the amino acid sequence of the LCDR1 of the antibody, the antigen binding fragment or the variant thereof of the present application may include SEQ ID NO: 80 or a variant thereof, the amino acid sequence of the LCDR2 may include SEQ ID NO: 81 or a variant thereof, the amino acid sequence of the LCDR3 may include SEQ ID NO: 82 or a variant thereof, and the amino acid sequence of the HCDR1 may include SEQ ID NO: 77 or a variant thereof, the amino acid sequence of the HCDR2 may include SEQ ID NO: 78 or a variant thereof, and the amino acid sequence of the HCDR3 may include SEQ ID NO: 79 or a variant thereof. For example, the antibody, the antigen binding fragment or the variant thereof may include the antibody YN-006 or an antibody with the same LCDR1-3 and HCDR1-3 therewith. In some embodiments, the amino acid sequence of the light chain variable region of the antibody, the antigen binding fragment or the variant thereof of the present application may include SEQ ID NO: 20 or a variant thereof, and the amino acid sequence of the heavy chain variable region may include SEQ ID NO: 25 or a variant thereof. For example, the antibody, the antigen binding fragment or the variant thereof may include the antibody YN-006 or an antibody having the same light chain variable region and heavy chain variable region therewith. In some embodiments, the antibody, the antigen binding fragment or the variant thereof of the present application may include a light chain and a heavy chain, the amino acid sequence of the light chain may be shown in SEQ ID NO: 23 and the heavy chain amino acid sequence may be shown in SEQ ID NO: 27. For example, the antibody, the antigen binding fragment or the variant thereof can include the antibody YN-006 or have the same light chain and heavy chain therewith.

In some embodiments, the antibody, the antigen binding fragment or the variant thereof of the present application competes with a reference antibody to bind to CD137 protein (e.g., human CD137 protein). The reference antibody may include LCDR1-3 and HCDR1-3, and the amino acid sequence of the LCDR1 may include SEQ ID NO: 80 or a variant thereof, the amino acid sequence of the LCDR2 may include SEQ ID NO: 81 or a variant thereof, the amino acid sequence of the LCDR3 may include SEQ ID NO: 82 or a variant thereof, and the amino acid sequence of the HCDR1 may include SEQ ID NO: 77 or a variant thereof, the amino acid sequence of the HCDR2 may include SEQ ID NO: 78 or a variant thereof, and the amino acid sequence of the HCDR3 may include SEQ ID NO: 79 or a variant thereof. In some embodiments, the reference antibody may include the antibody YN-006 or an antibody with the same LCDR1-3 and HCDR1-3 therewith. In some embodiments, the reference antibody may include a light chain variable region and a heavy chain variable region, the amino acid sequence of the light chain variable region may include SEQ ID NO: 20 or a variant thereof; and the amino acid sequence of the heavy chain variable region may include SEQ ID NO: 25 or a variant thereof. For example, the reference antibody may include the antibody YN-006 or an antibody having the same light chain variable region and heavy chain variable region therewith. In some embodiments, the reference antibody may include a light chain and a heavy chain, the amino acid sequence of the light chain may be shown in SEQ ID NO: 23 and the amino acid sequence of the heavy chain may be shown in SEQ ID NO: 27. For example, the reference antibody may include the antibody YN-006 or have the same light chain and heavy chain therewith.

In the present application, the CD137 protein may include a human CD137 protein.

In another aspect, the present application further provides a bispecific antibody which binds to a PD-L1 protein at a $K_D$ of lower than $2\times10^{-9}$ M (e.g., a $K_D$ of not higher than about $2\times10^{-9}$ M, not higher than about $1\times10^{-9}$ M, not higher than about $1\times10^{-10}$ M or not higher than about $8\times10^{-11}$ M or less), and binds to a CD137 protein with a $K_D$ of lower than $8\times10^{-9}$ M (e.g., a $K_D$ of not higher than about $8\times10^{-9}$ M, not higher than about $7\times10^{-9}$ M, not higher than about $6\times10^{-9}$ M, not higher than about $5\times10^{-9}$ M, not higher than about $4\times10^{-9}$ M, not higher than about $3\times10^{-9}$ M, not higher than about $2\times10^{-9}$ M, not higher than about $1\times10^{-9}$ M or not higher than about $1\times10^{-10}$ M or less).

In the present application, the PD-L1 protein is selected from the group consisting of human PD-L1 protein, monkey PD-L1 protein and murine PD-L1 protein; and the CD137 protein includes a human CD137 protein.

In the present application, the bispecific antibody includes a first targeting moiety that specifically binds to the PD-L1 protein, wherein the first targeting moiety may include the antibody, the antigen binding fragment or the variant thereof which binds to the PD-L1.

For example, the antigen-binding fragment in the first targeting moiety may be selected from the group consisting of Fab, Fab', F(ab)$_2$ and Fv fragment. For another example, the variant in the first targeting moiety may be selected from the group consisting of a protein or polypeptide which undergoes the substitution, deletion or addition of one or more amino acids in the antibody or an antigen-binding fragment thereof; and a protein or polypeptide having 85% or more (e.g., at least about 85%, about 90%, about 91%, about 92%, about 93%, about 94%, about 95%, about 96%, about 97%, about 98%, about 99% or more) sequence identity with the antibody or the antigen-binding fragment thereof. The antibody, the antigen binding fragment or the variant thereof may be the antibody, the antigen binding fragment or the variant thereof which binds to the PD-L1 protein.

In some embodiments, the antibody which binds to the PD-L1 protein in the bispecific antibody may include a light chain or a fragment thereof. For example, the light chain or the fragment thereof includes LCDR1-3, and the amino acid sequence of the LCDR1 is SEQ ID NO: 54-58; the amino acid sequence of the LCDR2 is SEQ ID NO: 60-61; and the amino acid sequence of the LCDR3 is selected from the group consisting of SEQ ID NO: 63-64. In some embodiments, the light chain or the fragment thereof may include a light chain variable region, and the amino acid sequence of the light chain variable region may be selected from the group consisting of SEQ ID NO: 4, SEQ ID NO: 11, SEQ ID NO: 33, SEQ ID NO: 37, SEQ ID NO: 39 and SEQ ID NO: 41. In some embodiments, the light chain or the fragment thereof of the antibody may include a human constant region, and the human constant region includes a human Igλ constant region.

In some embodiments, the light chain or the fragment thereof may include an amino acid sequence selected from the group consisting of SEQ ID NO: 8, SEQ ID NO: 15, SEQ ID NO: 34, SEQ ID NO: 38, SEQ ID NO: 40 and SEQ ID NO: 42.

In some embodiments, the antibody binding to the PD-L1 protein may include a heavy chain or a fragment thereof. For example, the heavy chain or the fragment thereof includes HCDR1-3, and the amino acid sequence of the HCDR1 is selected from the group consisting of SEQ ID NO: 46-47; the amino acid sequence of the HCDR2 is SEQ ID NO: 48; and the amino acid sequence of the HCDR3 is SEQ ID NO: 50-52.

In some embodiments, the heavy chain or the fragment thereof may include a heavy chain variable region, and the amino acid sequence of the heavy chain variable region may be selected from the group consisting of SEQ ID NO: 2, SEQ ID NO: 9, SEQ ID NO: 31 and SEQ ID NO: 35.

In some embodiments, the heavy chain or the fragment thereof may further include a human constant region, and the human constant region may include a human IgG constant region. For example, the human IgG constant region is human IgG1 constant region.

In some embodiments, the heavy chain or the fragment thereof may include an amino acid sequence selected from the group consisting of SEQ ID NO: 6, SEQ ID NO:13, SEQ ID NO: 32 and SEQ ID NO: 36.

In some embodiments, the bispecific antibody includes a second targeting moiety that specifically binds to the CD137 protein, wherein the second targeting moiety can include an antibody, the antigen binding fragment or the variant thereof which binds to the CD137 protein. In some embodiments, the antigen-binding fragment is selected from the group consisting of Fab, Fab', F(ab)₂ and Fv fragment. In some embodiments, the variant is selected from the group consisting of a protein or polypeptide which undergoes the substitution, deletion or addition of one or more amino acids in the antibody or the antigen-binding fragment thereof; and a protein or polypeptide having 85% or more (e.g., at least about 85%, about 90%, about 91%, about 92%, about 93%, about 94%, about 95%, about 96%, about 97%, about 98%, about 99% or more) sequence identity with the antibody or the antigen-binding fragment thereof.

In some embodiments, the antibody that binds to the CD137 protein may include a light chain or a fragment thereof. For example, the light chain or the fragment thereof includes LCDR1-3, and the amino acid sequences of the LCDR1-3 can be sequentially SEQ ID NO: 80, SEQ ID NO: 81 and SEQ ID NO: 82. In some embodiments, the light chain or the fragment thereof may include a light chain variable region, and the light chain variable region includes an amino acid sequence shown in SEQ ID NO: 20.

In some embodiments, the antibody that binds to the CD137 protein may include a heavy chain or a fragment thereof. In some embodiments, the heavy chain or the fragment thereof of the antibody may include HCDR1-3, and the amino acid sequences of the HCDR1-3 may be sequentially SEQ ID NO: 77, SEQ ID NO: 78 and SEQ ID NO: 79. In some embodiments, the heavy chain or the fragment thereof of the antibody may include a heavy chain variable region, and the amino acid sequence of the heavy chain variable region may be selected from the group consisting of SEQ ID NO: 18 and SEQ ID NO: 25.

In some embodiments, the antibody that binds to the CD137 protein may include a scFv, and the scFv may include an amino acid sequence shown in SEQ ID NO: 83.

In the present application, the bispecific antibody may include a first polypeptide chain and a second polypeptide chain, wherein the first polypeptide chain may include the heavy chain variable region of the antibody that binds to the PD-L1 protein, the heavy chain variable region of the antibody that binds to the CD137 protein, and the light chain variable region of the antibody that binds to the CD137 protein; and the second polypeptide chain may include the light chain variable region of the antibody that binds to the PD-L1 protein.

For example, in the first polypeptide chain, the heavy chain variable region of the antibody that binds to the PD-L1 protein may be located at the N-terminus of the heavy chain variable region of the antibody that binds to the CD137 protein, and the heavy chain variable region of the antibody that binds to the CD137 protein may be located at the N-terminus of the light chain variable region of the antibody that binds to the CD137 protein. For another example, in the first polypeptide chain, the heavy chain variable region of the antibody that binds to the PD-L1 protein may be located at the N-terminus of the light chain variable region of the antibody that binds to the CD137 protein, and the light chain variable region of the antibody that binds to the CD137 protein may be located at the N-terminus of the heavy chain variable region of the antibody that binds to the CD137 protein.

For example, in the first polypeptide chain, the light chain variable region of the antibody that binds to the CD137 protein and the heavy chain variable region of the antibody that binds to the CD137 protein constitute scFv. For example, the scFv can include an amino acid sequence shown in SEQ ID NO: 83.

The first polypeptide chain may further include a human IgG constant region. For example, the human IgG constant region may be a human IgG1 constant region.

In some embodiments, the human IgG constant region may be located at the C-terminus of the heavy chain variable region of the antibody that binds to the PD-L1 protein and may be located at the N-terminus of the light chain variable region of the antibody that binds to the CD137 protein; alternatively, the human IgG constant region may be located at the C-terminus of the heavy chain variable region of the antibody that binds to the PD-L1 protein and may be located at the N-terminus of the heavy chain variable region of the antibody that binds to the CD137 protein.

In some embodiments, the first polypeptide chain may include an amino acid sequence shown in SEQ ID NO: 30, SEQ ID NO: 43 and SEQ ID NO: 44.

In some embodiments, the second polypeptide chain may further include a human Igλ constant region.

In the present application, the second polypeptide chain may include the following amino acid sequences: SEQ ID NO: 15 and SEQ ID NO: 34.

For example, in the first targeting moiety of the bispecific antibody of the present application, the amino acid sequence of the LCDR1 may be selected from the group consisting of SEQ ID NO: 54, SEQ ID NO: 55, SEQ ID NO: 56, SEQ ID NO: 57 and SEQ ID NO: 58 or a variant thereof; the amino acid sequence of the LCDR2 may be selected from the group consisting of SEQ ID NO: 60 and SEQ ID NO: 61 or a variant thereof; the amino acid sequence of the LCDR3 may be selected from the group consisting of SEQ ID NO: 63 and SEQ ID NO: 64 or a variant thereof; and the amino acid sequence of the HCDR1 may be selected from the group consisting of SEQ ID NO: 46 and SEQ ID NO: 47 or a variant thereof; the amino acid sequence of the HCDR2 may include SEQ ID NO: 48 or a variant thereof; and the amino acid sequence of the HCDR3 may be selected from the group consisting of SEQ ID NO: 50-52 or a variant thereof. In some embodiments, the amino acid sequence of the light chain variable region of the antibody, the antigen binding fragment or the variant thereof of the present application may be selected from the group consisting of SEQ ID NO: 4, SEQ ID NO: 11, SEQ ID NO: 33, SEQ ID NO: 37, SEQ ID NO: 39 and SEQ ID NO: 41 or a variant thereof; and the amino acid sequence of the heavy chain variable region may be selected from the group consisting of SEQ ID NO: 2, SEQ ID NO: 9, SEQ ID NO: 31 and SEQ ID NO: 35 or a variant thereof. In some embodiments, the antibody, the antigen binding fragment or the variant thereof of the present application may include a light chain and a heavy chain, the amino acid sequence of the light chain may be an amino acid sequence selected from the group consisting of SEQ ID NO: 8, SEQ ID NO: 15, SEQ ID NO: 34, SEQ ID NO: 38, SEQ ID NO: 40 and SEQ ID NO: 42, and the heavy chain amino acid sequence may be an amino acid sequence selected from the group consisting of SEQ ID NO: 6, SEQ ID NO: 13, SEQ ID NO: 32 and SEQ ID NO: 36.

For example, in the second targeting moiety of the bispecific antibody of the present application, the amino acid sequence of the LCDR1 may include SEQ ID NO: 80 or a variant thereof; the amino acid sequence of the LCDR2 may include SEQ ID NO: 81 or a variant thereof; the amino acid sequence of the LCDR3 may include SEQ ID NO: 82 or a variant thereof; and the amino acid sequence of the HCDR1 may include SEQ ID NO: 77 or a variant thereof; the amino acid sequence of the HCDR2 may include SEQ ID NO: 78 or a variant thereof; and the amino acid sequence of the HCDR3 may include SEQ ID NO: 79 or a variant thereof. In some embodiments, the amino acid sequence of the light chain variable region of the antibody, the antigen binding fragment or the variant thereof of the present application may include SEQ ID NO: 20 or a variant thereof; and the amino acid sequence of the heavy chain variable region may be those selected from the group consisting of SEQ ID NO: 18 and SEQ ID NO: 25 or their variants. In some embodiments, the antibody, the antigen binding fragment or the variant thereof of the present application may include a light chain and a heavy chain, the amino acid sequence of the light chain may be shown in SEQ ID NO: 23 and the heavy chain amino acid sequence may be shown in SEQ ID NO: 21 or SEQ ID NO: 27.

For example, in the bispecific antibody of the present application, the first polypeptide may include an amino acid sequence shown in SEQ ID NO: 30, and the second polypeptide may include an amino acid sequence shown in SEQ ID NO: 15. The bispecific antibody may include the antibody YN-007 or an antibody with the same first polypeptide and second polypeptide. wherein, the first polypeptide may include an amino acid sequence shown in SEQ ID NO: 25, an amino acid sequence shown in SEQ ID NO: 20 and an amino acid sequence shown in SEQ ID NO: 13; and the second polypeptide may include an amino acid sequence shown in SEQ ID NO: 15.

For another example, in the bispecific antibody of the present application, the first polypeptide may include an amino acid sequence shown in SEQ ID NO: 43, and the second polypeptide may include an amino acid sequence shown in SEQ ID NO: 34. The bispecific antibody may include the antibody YN-051 or an antibody with the same first polypeptide and second polypeptide. Wherein, the first polypeptide may include an amino acid sequence shown in SEQ ID NO: 25, an amino acid sequence shown in SEQ ID NO: 20 and an amino acid sequence shown in SEQ ID NO: 32; and the second polypeptide may include an amino acid sequence shown in SEQ ID NO: 34.

For another example, in the bispecific antibody of the present application, the first polypeptide may include an amino acid sequence shown in SEQ ID NO: 44, and the second polypeptide may include an amino acid sequence shown in SEQ ID NO: 34. The bispecific antibody may include the antibody YN-052 or an antibody with the same first polypeptide and second polypeptide. Wherein, the first polypeptide may include an amino acid sequence shown in SEQ ID NO: 25, an amino acid sequence shown in SEQ ID NO: 20 and an amino acid sequence shown in SEQ ID NO: 36; and the second polypeptide may include an amino acid sequence shown in SEQ ID NO: 34.

For example, in the bispecific antibody of the present application, the first polypeptide may include an amino acid sequence shown in SEQ ID NO: 30, and the second polypeptide may include an amino acid sequence shown in SEQ ID NO: 15. The bispecific antibody may include the antibody YN-007 or an antibody with the same first polypeptide and second polypeptide. Wherein, the first polypeptide may include an amino acid sequence shown in SEQ ID NO: 27, an amino acid sequence shown in SEQ ID NO: 23 and an amino acid sequence shown in SEQ ID NO: 13; and the second polypeptide may include an amino acid sequence shown in SEQ ID NO: 15.

For another example, in the bispecific antibody of the present application, the first polypeptide may include an amino acid sequence shown in SEQ ID NO: 43, and the second polypeptide may include an amino acid sequence shown in SEQ ID NO: 34. The bispecific antibody can include the antibody YN-051 or an antibody with the same first polypeptide and second polypeptide. Wherein, the first polypeptide may include an amino acid sequence shown in SEQ ID NO: 32, an amino acid sequence shown in SEQ ID NO: 27, an amino acid sequence shown in SEQ ID NO: 23; and the second polypeptide may include an amino acid sequence shown in SEQ ID NO: 34.

For another example, in the bispecific antibody of the present application, the first polypeptide may include an amino acid sequence shown in SEQ ID NO: 44, and the second polypeptide may include an amino acid sequence shown in SEQ ID NO: 34. The bispecific antibody may include the antibody YN-052 or an antibody with the same first polypeptide and second polypeptide. Wherein, the first polypeptide may include an amino acid sequence shown in SEQ ID NO: 36, an amino acid sequence shown in SEQ ID NO: 27, an amino acid sequence shown in SEQ ID NO: 23; and the second polypeptide may include an amino acid sequence shown in SEQ ID NO: 34.

Nucleic Acid, Vector, Host Cell and Preparation Method

In another aspect, the present application further provides one or more isolated nucleic acid molecules which can encode the antibody, the antigen binding fragment or the variant thereof, or the bispecific antibody of the present application. For example, each nucleic acid molecule of the one or more nucleic acid molecules may either encode the whole antibody or an antigen-binding fragment thereof, or encode a portion therein (e.g., one or more of HCDR1-3, LCDR1-3, VL, VH, light chain or heavy chain).

The nucleic acid molecule of the present application may be isolated. For example, it may be produced or synthesized by the following methods: (i) in vitro amplification, such as, amplification via a polymerase chain reaction (PCR), (ii) clonal recombination, (iii) purification, such as, fractionation by restriction enzyme digestion and gel electrophoresis, or (iv) synthesis, such as, by chemical synthesis. In some embodiments, the isolated nucleic acid is a nucleic acid molecule prepared by the recombinant DNA technology.

In the present application, the nucleic acid encoding the antibody or the antigen-binding fragment thereof may be prepared by a variety of methods known in the art, including but not limited to, overlap extension PCR by using restriction fragment operation or synthetic oligonucleotides. For specific operations, please refer to Sambrook et al., Molecular Cloning, A Laboratory Manual, Cold Spring Harbor Laboratory Press, Cold Spring Harbor, N.Y., 1989; and Ausube, et al., Current Protocols in Molecular Biology, Greene Publishing and Wiley-Interscience, New York N.Y., 1993.

In another aspect, the present application provides one or more vectors, and includes the one or more nucleic acid molecules of the present application. Each vector may include one or more of the nucleic acid molecules. Moreover, the vector may further include other genes, such as, marker genes that allow selecting this vector in an appropriate host cell and under appropriate conditions. Moreover, the vector may further include an expression control element that allows the coding region to be correctly expressed in an appropriate host cell. Such control elements are well known by persons skilled in the art, e.g., they may include promoters, ribosome binding sites, enhancers and other control elements for regulating gene transcription or mRNA translation, etc. In some embodiments, the expression control sequence is a regulatory element. The specific structure of the expression control sequence may vary depending on the function of the species or cell types, but usually includes 5'non-transcribed sequence and 5' and 3'non-translated sequence involved in transcription and translation initiation, such as, TATA box, capped sequence, CAAT sequence, etc. For example, 5'non-transcribed expression control sequence may include the promoter region that may include a promoter sequence for transcriptional control of the functionally linked nucleic acid. One or more nucleic acid molecules described in the present application may be operably linked to the expression control element.

The vector may include, e.g., plasmid, cosmid, virus, phage, or other vectors commonly used in genetic engineering, for example, the vector is an expression vector.

In another aspect, the present application provides a cell, which may include the nucleic acid molecule of the present application and/or the vector described in the present application. The cell may be a host cell. In some embodiments, each host cell may include one nucleic acid molecule or vector described in the present application. In some embodiments, each host cell may include multiple (e.g., two or more) nucleic acid molecules or vectors described in the present application. For example, the vector of the present application may be introduced into the host cell, e.g., a eukaryotic cell, e.g., a plant-derived cell, fungus or yeast cells, etc. The vector of the present application may be introduced into the host cell by methods known in the art, such as electroporation, lipofectine transfection, lipofectamin transfection, and the like.

In another aspect, the present application provides one or more host cells, which include the nucleic acid molecule or the vector.

In another aspect, the present application provides a method for preparing the antibody, the antigen binding fragment or the variant thereof, or the bispecific antibody. The method may include culturing the host cell of the present application under conditions that allow the antibody, the antigen-binding fragment or variant thereof, or the bispecific antibody to be expressed, and optionally harvesting the antibody, antigen-binding fragment or variant thereof. For example, it is possible to use an appropriate medium, an appropriate temperature, a culture time, etc., and these methods are understood by those of ordinary skills in the art.

Pharmaceutical Composition, Use

In another aspect, the present application provides a pharmaceutical composition which may include the antibody, the antigen binding fragment or the variant thereof, or the bispecific antibody, the nucleic acid molecule, the vector and/or the host cell, and optionally a pharmaceutical acceptable adjuvant.

The pharmaceutical acceptable adjuvant may include buffers, antioxidants, preservatives, low molecular weight polypeptides, proteins, hydrophilic polymers, amino acids, sugars, chelators, counter-ions, metal complexes and/or nonionic surfactant and the like.

In the present application, the pharmaceutical composition may be formulated for oral administration, intravenous administration, intramuscular administration, in situ administration at the tumor site, inhalation, rectal administration, vaginal administration, transdermal administration or administration via subcutaneous depot.

In another aspect, the present application provides use of the antibody, the antigen binding fragment or the variant thereof, or the bispecific antibody, the nucleic acid molecule, the vector, the host cell and/or the pharmaceutical composition in manufacture of a drug for relieving or treating tumors. Among others, the tumors include colon cancer.

In another aspect, the present application provides a method of enhancing the function of T cells, including administering the antibody that binds to the PD-L1 protein, the antigen binding fragment or the variant thereof, the antibody that binds to the CD137 protein, the antigen binding fragment or the variant thereof, or the bispecific antibody, the nucleic acid molecule, the vector, the host cell and/or the pharmaceutical composition to a subject in need thereof. Of those, the T cells are tumor associated dysfunctional T cells.

In another aspect, the present application provides a method of inhibiting the binding of PD-L1 protein to PD-1 protein which includes administering the antibody, the antigen binding fragment or the variant thereof, or the bispecific antibody, the nucleic acid molecule, the vector, the host cell and/or the pharmaceutical composition to a subject in need thereof.

In the present application, the position of the antibody CDR may be determined in accordance with the antibody Kabat definition method.

The present application further includes the following embodiments:

1. An antibody, an antigen binding fragment or a variant thereof which binds to a PD-L1 protein with a $K_D$ of $3 \times 10^{-9}$ M or less.
2. The antibody, the antigen binding fragment or the variant thereof according to embodiment 1, which binds to a PD-L1 protein with a $K_D$ of $8 \times 10^{-11}$ M or less.
3. The antibody, the antigen binding fragment or the variant thereof according to any of embodiments 1-2, which inhibits the binding of PD-L1 to PD-1.
4. The antibody, the antigen binding fragment or the variant thereof according to any of embodiments 1-3, is capable of relieving or treating tumor-associated diseases.
5. The antibody, the antigen binding fragment or the variant thereof according to embodiment 4, wherein the tumor includes colon cancer.
6. The antibody, the antigen binding fragment or the variant thereof according to any of embodiments 1-5, wherein the antibody is selected from the group consisting of monoclonal antibody, single-strand antibody, chimeric antibody, humanized antibody and fully human antibody.
7. The antibody, the antigen binding fragment or the variant thereof according to any of embodiments 1-6, wherein the antigen-binding fragment is selected from the group consisting of Fab, Fab', F(ab)$_2$ and Fv fragment.
8. The antibody, the antigen binding fragment or the variant thereof according to any of embodiments 1-7, wherein the variant is selected from the group consisting of:
   1) a protein or polypeptide obtained by substitution, deletion or addition of one or more amino acids in the antibody or the antigen-binding fragment thereof; and 2) a protein or polypeptide having 90% or more of sequence identity as the antibody or the antigen-binding fragment thereof.
9. The antibody, the antigen binding fragment or the variant thereof according to any of embodiments 1-8, which competes with a reference antibody which binds to the PD-L1 protein, wherein the reference antibody includes a light chain variable region and a heavy chain variable region, the light chain variable region of the reference antibody includes LCDR1-3, the light chain variable region of the reference antibody includes LCDR1-3, and the LCDR1 includes an amino acid sequence selected from the group consisting of SEQ ID NO: 54-58; the LCDR2 includes an amino acid sequence selected from the group consisting of SEQ ID NO: 60-61; and the LCDR3 includes an amino acid sequence selected from the group consisting of SEQ ID NO: 63-64; and the heavy chain variable region of the reference antibody includes HCDR1-3, the HCDR1 includes an amino acid sequence selected from the group consisting of SEQ ID NO: 46-47; the HCDR2 includes an amino acid sequence selected from the group consisting of SEQ ID NO: 48; and the HCDR3 includes an amino acid sequence selected from the group consisting of SEQ ID NO: 50-52.
10. The antibody, the antigen binding fragment or the variant thereof according to embodiment 9, wherein the light chain variable region of the reference antibody includes an amino acid sequence selected from the group consisting of SEQ ID NO: 4, SEQ ID NO: 11, SEQ ID NO: 33, SEQ ID NO: 37, SEQ ID NO: 39 and SEQ ID NO: 41, and the heavy chain variable region of the reference antibody includes an amino acid sequence selected from the group consisting of SEQ ID NO: 2, SEQ ID NO: 9, SEQ ID NO: 31 and SEQ ID NO: 35.
11. The antibody, the antigen binding fragment or the variant thereof according to any of embodiment 9-10, wherein the light chain of the reference antibody includes an amino acid sequence selected from the group consisting of SEQ ID NO: 8, SEQ ID NO: 15, SEQ ID NO: 34, SEQ ID NO: 38, SEQ ID NO: 40 and SEQ ID NO: 42; and the heavy chain of the reference antibody includes an amino acid sequence selected from the group consisting of SEQ ID NO: 6, SEQ ID NO: 13, SEQ ID NO: 32 and SEQ ID NO: 36.
12. The antibody, the antigen binding fragment or the variant thereof according to embodiments 1-11, wherein the antibody includes an antibody light chain or a fragment thereof which includes a LCDR1, and the LCDR1 includes an amino acid sequence shown in SEQ ID NO: 53: TGTX$_1$SX$_2$VGGYX$_3$X$_4$VS; wherein X$_1$ is S, R or V; X$_2$ is D, E or S; X$_3$ is N or R; X$_4$ is Y or E, and wherein the LCDR1 is determined according to the index of the antibody Kabat number.
13. The antibody, the antigen binding fragment or the variant thereof according to embodiment 12, wherein the LCDR1 includes an amino acid sequence selected from the group consisting of SEQ ID NO: 54-58.
14. The antibody, the antigen binding fragment or the variant thereof according to any of embodiments 11-13, wherein the antibody light chain or the fragment thereof includes a LCDR2 including an amino acid sequence shown in SEQ ID NO: 59: X$_1$NSX$_2$RPS, wherein X$_1$ is G or E; X$_2$ is N or I, and wherein the LCDR2 is determined according to the index of the antibody Kabat number.
15. The antibody, the antigen binding fragment or the variant thereof according to embodiment 14, wherein the LCDR2 includes an amino acid sequence selected from the group consisting of SEQ ID NO: 60-61.
16. The antibody, the antigen binding fragment or the variant thereof according to any of embodiments 11-15, wherein the antibody light chain or the fragment thereof includes a LCDR3 including an amino acid sequence shown in SEQ ID NO: 62: QSYDSSLSGX$_1$V, wherein X$_1$ is S or T, and wherein the LCDR3 is determined according to the index of the antibody Kabat number.
17. The antibody, the antigen binding fragment or the variant thereof according to any of embodiments 11-16, wherein the antibody light chain or the fragment thereof further includes framework regions L-FR1, L-FR2, L-FR3, and L-FR4.
18. The antibody, the antigen binding fragment or the variant thereof according to embodiment 17, wherein the framework regions are selected from the group consisting of human consensus framework sequences and human germline sequences.
19. The antibody, the antigen binding fragment or the variant thereof according to any of embodiments 17-18, wherein the C-terminus of the L-FR1 is directly or indirectly linked to the N-terminus of the LCDR1, and the L-FR1 includes an amino acid sequence selected from the group consisting of SEQ ID NO: 71.
20. The antibody, the antigen binding fragment or the variant thereof according to any of embodiments 17-19, wherein the L-FR2 is located between the LCDR1 and the LCDR2, and the L-FR2 includes an amino acid sequence selected from the group consisting of SEQ ID NO: 72.
21. The antibody, the antigen binding fragment or the variant thereof according to any of embodiments 17-20, wherein the L-FR3 is located between the LCDR2 and the LCDR3, and the L-FR3 includes an amino acid sequence selected from the group consisting of SEQ ID NO: 73-75.
22. The antibody, the antigen binding fragment or the variant thereof according to any of embodiments 17-21, wherein the N-terminus of the L-FR4 is directly or indirectly linked to the C-terminus of the LCDR3, and the L-FR4 includes an amino acid sequence selected from the group consisting of SEQ ID NO: 76.
23. The antibody, the antigen binding fragment or the variant thereof according to any of embodiments 12-22, wherein the antibody light chain or a fragment thereof includes a light chain variable region VL, and the light chain variable region VL includes an amino acid sequence selected from the group consisting of SEQ ID NO: 4, SEQ ID NO: 11, SEQ ID NO: 33, SEQ ID NO: 37, SEQ ID NO: 39 and SEQ ID NO: 41.
24. The antibody, the antigen binding fragment or the variant thereof according to any of embodiments 12-23, wherein the antibody light chain or the fragment thereof further includes a human constant region, and the human constant region includes a human Ig, constant region.
25. The antibody, the antigen binding fragment or the variant thereof according to any of embodiments 12-24, wherein the antibody light chain or the fragment thereof includes an amino acid sequence selected from the group consisting of SEQ ID NO: 8, SEQ ID NO: 15, SEQ ID NO: 34, SEQ ID NO: 38, SEQ ID NO: 40 and SEQ ID NO: 42.

26. The antibody, the antigen binding fragment or the variant thereof according to any of embodiments 1-25, wherein the antibody includes an antibody heavy chain or a fragment thereof which includes HCDR1, and the HCDR1 includes an amino acid sequence selected from the group consisting of those shown in SEQ ID NO: 45: $X_1$YAIS, wherein $X_1$ is S or T, and wherein the HCDR1 is determined according to the index of the antibody Kabat number.

27. The antibody, the antigen binding fragment or the variant thereof according to embodiment 26, wherein the antibody heavy chain or the fragment thereof includes HCDR2, the HCDR2 includes an amino acid sequence shown in SEQ ID NO: 48, and wherein the HCDR2 is determined according to the index of the antibody Kabat number.

28. The antibody, the antigen binding fragment or the variant thereof according to any of embodiments 26-27, wherein the antibody heavy chain or the fragment thereof includes HCDR3, and the HCDR3 includes an amino acid sequence selected from that shown in SEQ ID NO: 49: $TMX_1X_2YX_3X_4GNX_5DY$, wherein $X_1$ is D, E or G, $X_2$ is G or E, $X_3$ is S or G, $X_4$ is Y or F, $X_5$ is F or Y, and wherein the HCDR3 is determined according to the index of the antibody Kabat number.

29. The antibody, the antigen binding fragment or the variant thereof according to embodiment 28, wherein the HCDR3 includes an amino acid sequence selected from the group consisting of SEQ ID NO: 50-52.

30. The antibody, the antigen binding fragment or the variant thereof according to any of embodiments 26-29, wherein the antibody heavy chain or the fragment thereof further includes framework regions H-FRT, H-FR2, H-FR3, and H-FR4.

31. The antibody, the antigen binding fragment or the variant thereof according to embodiments 30, wherein the framework regions are selected from the group consisting of human consensus framework sequences and human germline sequences.

32. The antibody, the antigen binding fragment or the variant thereof according to any of embodiments 30-31, wherein the C-terminus of H-FR1 is directly or indirectly linked to the N-terminus of HCDR1, and the H-FR1 includes an amino acid sequence selected from the group consisting of SEQ ID NO: 65-67.

33. The antibody, the antigen binding fragment or the variant thereof according to any of embodiments 30-32, wherein the H-FR2 is located between the HCDR1 and the HCDR2, and the H-FR2 includes an amino acid sequence selected from the group consisting of SEQ ID NO: 68.

34. The antibody, the antigen binding fragment or the variant thereof according to any of embodiments 30-33, wherein the H-FR3 is located between the HCDR2 and the HCDR3, and the H-FR3 includes an amino acid sequence selected from the group consisting of SEQ ID NO: 69.

35. The antibody, the antigen binding fragment or the variant thereof according to any of embodiments 30-34, wherein the N-terminus of H-FR4 is directly or indirectly linked to the C-terminus of HCDR3, and the H-FR4 includes an amino acid sequence selected from the group consisting of SEQ ID NO: 70.

36. The antibody, the antigen binding fragment or the variant thereof according to any of embodiments 26-35, wherein the antibody heavy chain or the fragment thereof includes a heavy chain variable region VH, and the heavy chain variable region VH includes an amino acid sequence selected from the group consisting of SEQ ID NO: 2, SEQ ID NO: 9, SEQ ID NO: 31 and SEQ ID NO: 35.

37. The antibody, the antigen binding fragment or the variant thereof according to any of embodiments 26-36, wherein the antibody heavy chain or the fragment thereof further includes a human constant region, and the human constant region includes a human IgG1 constant region.

38. The antibody, the antigen binding fragment or the variant thereof according to any of embodiments 26-37, wherein the antibody heavy chain or the fragment thereof includes an amino acid sequence selected from the group consisting of SEQ ID NO: 6, SEQ ID NO: 13, SEQ ID NO: 32 and SEQ ID NO: 36.

39. The antibody, the antigen binding fragment or the variant thereof according to any of embodiments 1-38, wherein the PD-L1 protein is selected from the group consisting of human PD-L1 protein, monkey PD-L1 protein and murine PD-L1 protein.

40. An antibody, an antigen binding fragment or a variant thereof which binds to a CD137 protein with a $K_D$ of $5 \times 10^{-9}$ M or less.

41. The antibody, the antigen binding fragment or the variant thereof according to embodiment 40, which binds to a CD137 protein with a $K_D$ of $3 \times 10^{-9}$ M or less.

42. The antibody, the antigen binding fragment or the variant thereof according to any of embodiments 40-41, which has a CD137 agonistic activity.

43. The antibody, the antigen binding fragment or the variant thereof according to any of embodiments 40-42, is capable of relieving or treating tumors.

44. The antibody, the antigen binding fragment or the variant thereof according to embodiment 43, wherein the tumor includes colon cancer.

45. The antibody, the antigen binding fragment or the variant thereof according to any of embodiments 40-44, wherein the antibody is selected from the group consisting of monoclonal antibody, single-strand antibody, chimeric antibody, humanized antibody and fully human antibody.

46. The antibody, the antigen binding fragment or the variant thereof according to any of embodiments 40-45, wherein the antigen-binding fragment is selected from the group consisting of Fab, Fab', F(ab)$_2$ and Fv fragment.

47. The antibody, the antigen binding fragment or the variant thereof according to any of embodiments 40-46, wherein the variant is selected from the group consisting of:
1) a protein or polypeptide obtained by substitution, deletion or addition of one or more amino acids in the antibody or the antigen-binding fragment thereof; and
2) a protein or polypeptide having 90% or more of sequence identity as the antibody or the antigen-binding fragment thereof.

48. The antibody, the antigen binding fragment or the variant thereof according to any of embodiments 40-47, which competes with a reference antibody to bind to the CD137 protein, wherein the reference antibody includes a light chain variable region and a heavy chain variable region, the light chain variable region of the reference antibody includes LCDR1-3, and the amino acid sequence of the LCDR1-3 are sequentially shown in SEQ ID NO: 80-82, and the heavy chain variable region of the reference antibody includes HCDR1-3, and the amino acid sequences of the HCDR1-3 are sequentially shown in SEQ ID NO: 77-79.

49. The antibody, the antigen binding fragment or the variant thereof according to embodiment 48, wherein the light chain variable region of the reference antibody includes an amino acid sequence selected from that shown in SEQ ID NO: 20, and the heavy chain variable region of the reference antibody includes an amino acid sequence selected from those shown in SEQ ID NO: 18 and SEQ ID NO: 25.

50. The antibody, the antigen binding fragment or the variant thereof according to any of embodiments 48-49, wherein the light chain of the reference antibody includes an amino acid sequence selected from that shown in SEQ ID NO: 23; and the heavy chain of the reference antibody includes an amino acid sequence selected from those shown in SEQ ID NO: 21 and SEQ ID NO: 27.

51. The antibody, the antigen binding fragment or the variant thereof according to any of embodiments 40-50, wherein the antibody includes an antibody light chain or a fragment thereof.

52. The antibody, the antigen binding fragment or the variant thereof according to embodiment 51, wherein the antibody light chain or the fragment thereof includes a LCDR1, and the LCDR1 includes an amino acid sequence selected from that shown in SEQ ID NO: 80.

53. The antibody, the antigen binding fragment or the variant thereof according to any of embodiments 51-52, wherein the antibody light chain or the fragment thereof includes LCDR2, and the LCDR2 includes an amino acid sequence shown in SEQ ID NO: 81.

54. The antibody, the antigen binding fragment or the variant thereof according to any of embodiments 51-53, wherein the antibody light chain or the fragment thereof includes LCDR3, and the LCDR3 includes an amino acid sequence selected from that shown in SEQ ID NO: 82.

55. The antibody, the antigen binding fragment or the variant thereof according to any of embodiments 51-54, wherein the antibody light chain or the fragment thereof further includes framework regions L-FR1, L-FR2, L-FR3 and L-FR4.

56. The antibody, the antigen binding fragment or the variant thereof according to embodiment 55, wherein the framework regions are selected from the group consisting of human consensus framework sequences and human germline sequences.

57. The antibody, the antigen binding fragment or the variant thereof according to any of embodiments 55-56, wherein the C-terminus of the L-FR1 is directly or indirectly linked to the N-terminus of the LCDR1, and the L-FR1 includes an amino acid sequence selected from that shown in SEQ ID NO: 89.

58 The antibody, the antigen binding fragment or the variant thereof according to any of embodiments 55-57, wherein the L-FR2 is located between the LCDR1 and the LCDR2, and the L-FR2 includes an amino acid sequence selected from that shown in SEQ ID NO: 90.

59. The antibody, the antigen binding fragment or the variant thereof according to any of embodiments 55-58, wherein the L-FR3 is located between the LCDR2 and the LCDR3, and the L-FR3 includes an amino acid sequence selected from that shown in SEQ ID NO: 91.

60. The antibody, the antigen binding fragment or the variant thereof according to any of embodiments 55-59, wherein the N-terminus of the L-FR4 is directly or indirectly linked to the C-terminus of the LCDR3, and the L-FR4 includes an amino acid sequence selected from that shown in SEQ ID NO: 92.

61. The antibody, the antigen binding fragment or the variant thereof according to any of embodiments 51-60, wherein the antibody light chain or the fragment thereof includes a light chain variable region VL, and the light chain variable region VL includes an amino acid sequence selected from that shown in SEQ ID NO: 20.

62. The antibody, the antigen binding fragment or the variant thereof according to any of embodiments 51-61, wherein the antibody light chain or the fragment thereof further includes a human constant region and the human constant region includes a human Igλ constant region.

63. The antibody, the antigen binding fragment or the variant thereof according to any of embodiments 51-62, wherein the antibody light chain or the fragment thereof includes an amino acid sequence selected from that shown in SEQ ID NO: 23.

64. The antibody, the antigen binding fragment or the variant thereof according to any of embodiments 40-63, wherein the antibody includes an antibody heavy chain or a fragment thereof.

65. The antibody, the antigen binding fragment or the variant thereof according to embodiment 64, wherein the antibody heavy chain or the fragment thereof includes a HCDR1, and the HCDR1 includes an amino acid sequence selected from that shown in SEQ ID NO: 77.

66. The antibody, the antigen binding fragment or the variant thereof according to any of embodiments 64-65, wherein the antibody heavy chain or the fragment thereof includes a HCDR2, and the HCDR2 includes an amino acid sequence selected from that shown in SEQ ID NO: 78.

67. The antibody, the antigen binding fragment or the variant thereof according to any of embodiments 64-66, wherein the antibody heavy chain or the fragment thereof includes a HCDR3, and the HCDR3 includes an amino acid sequence selected from that shown in SEQ ID NO: 79.

68. The antibody, the antigen binding fragment or the variant thereof according to any of embodiments 64-67, wherein the antibody heavy chain or the fragment thereof further includes framework regions H-FRT, H-FR2, H-FR3 and H-FR4.

69. The antibody, the antigen binding fragment or the variant thereof according to embodiment 68, wherein the framework regions are selected from the group consisting of human consensus framework sequences and human germline sequences.

70. The antibody, the antigen binding fragment or the variant thereof according to any of embodiments 68-69, wherein the C-terminus of H-FR1 is directly or indirectly linked to the N-terminus of HCDR1, and the H-FR1 includes an amino acid sequence selected from that shown in SEQ ID NO: 84-85.

71. The antibody, the antigen binding fragment or the variant thereof according to any of embodiments 68-70, wherein the H-FR2 is located between the HCDR1 and the HCDR2, and the H-FR2 includes an amino acid sequence selected from that shown in SEQ ID NO: 86.

72. The antibody, the antigen binding fragment or the variant thereof according to any of embodiments 68-71, wherein the H-FR3 is located between the HCDR2 and the HCDR3, and the H-FR3 includes an amino acid sequence selected from that shown in SEQ ID NO: 87.
73. The antibody, the antigen binding fragment or the variant thereof according to any of embodiments 68-72, wherein the N-terminus of H-FR4 is directly or indirectly linked to the C-terminus of HCDR3, and the H-FR4 includes an amino acid sequence selected from that shown in SEQ ID NO: 88.
74. The antibody, the antigen binding fragment or the variant thereof according to any of embodiments 68-73, wherein the antibody heavy chain or the fragment thereof includes a heavy chain variable region VH, and the heavy chain variable region VH includes an amino acid sequence selected from that shown in SEQ ID NO: 18 or SEQ ID NO: 25.
75. The antibody, the antigen binding fragment or the variant thereof according to any of embodiments 64-74, wherein the antibody heavy chain or the fragment thereof further includes a human constant region, and the human constant region includes a human IgG constant region.
76. The antibody, the antigen binding fragment or the variant thereof according to embodiment 75, wherein the IgG constant region includes a human IgG1 constant region.
77. The antibody, the antigen binding fragment or the variant thereof according to any of embodiments 64-76, wherein the antibody heavy chain or the fragment thereof includes an amino acid sequence selected from that shown in SEQ ID NO: 21 or SEQ ID NO: 27.
78. The antibody, the antigen binding fragment or the variant thereof according to any of embodiments 40-77, wherein the CD137 protein includes a human CD137 protein.
79. A bispecific antibody which binds to a PD-L1 protein with a $K_D$ of $2\times10^{-9}$ M or less and binds to a CD137 protein at a $K_D$ of $8\times10^{-9}$ M or less.
80. The bispecific antibody according to embodiments 30 which includes a first targeting moiety that specifically binds to the PD-L1 protein, wherein the first targeting moiety includes the antibody, the antigen binding fragment or the variant thereof according to any of embodiments 1-39.
81. The bispecific antibody according to any of embodiments 30-31 which includes a second targeting moiety that specifically binds to the CD137 protein, wherein the second targeting moiety includes the antibody, the antigen binding fragment or the variant thereof according to any of embodiments 40-78.
82. The bispecific antibody according to any of embodiments 79-81 which includes a first polypeptide chain and a second polypeptide chain, wherein the first polypeptide chain includes the heavy chain variable region of the antibody that binds to the PD-L1 protein, the heavy chain variable region of the antibody that binds to the CD137 protein, and the light chain variable region of the antibody that binds to the CD137 protein; and the second polypeptide chain includes the light chain variable region of the antibody that binds to the PD-L1 protein.
83. The bispecific antibody according to embodiment 82, wherein in the first polypeptide chain, the heavy chain variable region of the antibody that binds to the PD-L1 protein is located at the N-terminus of the heavy chain variable region of the antibody that binds to the CD137 protein, and the heavy chain variable region of the antibody that binds to the CD137 protein is located at the N-terminus of the light chain variable region of the antibody that binds to the CD137 protein; alternatively, the heavy chain variable region of the antibody that binds to the PD-L1 protein is located at the N-terminus of the light chain variable region of the antibody that binds to the CD137 protein, and the light chain variable region of the antibody that binds to the CD137 protein is located at the N-terminus of the heavy chain variable region of the antibody that binds to the CD137 protein.
84. The bispecific antibody according to any of embodiments 82-83, wherein the light chain variable region of the antibody that binds to the CD137 protein and the heavy chain variable region of the antibody that binds to the CD137 protein in the first polypeptide chain constitute scFv.
85. The bispecific antibody according to any of embodiments 82-84, wherein the first polypeptide chain further includes a human IgG constant region, and the human IgG constant region is located at the C-terminus of the heavy chain variable region of the antibody that binds to the PD-L1 protein and located at the N-terminus of the light chain variable region of the antibody that binds to the CD137 protein; alternatively, the human IgG constant region is located at the C-terminus of the heavy chain variable region of the antibody that binds to the PD-L1 protein and located at the N-terminus of the heavy chain variable region of the antibody that binds to the CD137 protein.
86. The bispecific antibody according to any of embodiments 82-85, wherein the first polypeptide chain includes an amino acid sequence selected from the group consisting of SEQ ID NO: 30, SEQ ID NO: 43 and SEQ ID NO: 44.
87. The bispecific antibody according to any of embodiments 82-86, wherein the second polypeptide chain includes an amino acid sequence selected from the group consisting of SEQ ID NO: 15 and SEQ ID NO: 34.
88. One or more isolated nucleic acid molecules which encode the antibody, the antigen binding fragment or the variant thereof of any of embodiments 1-39, the antibody, the antigen binding fragment or the variant thereof of any of embodiments 40-78, or the bispecific antibody of any of embodiments 79-87.
89. A vector which includes the nucleic acid molecule according to embodiment 88.
90. A cell which includes the nucleic acid molecule according to embodiment 88 or the vector according to embodiment 89.
91. A method of preparing the antibody, the antigen binding fragment or the variant thereof of any of embodiments 1-39, the antibody, the antigen binding fragment or the variant thereof of any of embodiments 40-78, or the bispecific antibody of any of embodiments 79-87, including culturing the cell according to embodiment 90 under conditions that allow expression of the antibody, the antigen binding fragment or the variant thereof of any of embodiments 1-39, the antibody, the antigen binding fragment or the variant thereof of any of embodiments 40-78, or the bispecific antibody of any of embodiments 79-87.
92. A pharmaceutical composition which includes the antibody, the antigen binding fragment or the variant thereof of any of embodiments 1-39, the antibody, the antigen binding fragment or the variant thereof of any of embodiments 40-78, or the bispecific antibody of any of embodiments 79-87, the nucleic acid molecule of embodiment 88, the vector of embodiment 89 and/or the cell of embodiments 90, and optionally a pharmaceutical acceptable adjuvant.
93. Use of the antibody, the antigen binding fragment or the variant thereof of any of embodiments 1-39, the antibody, the antigen binding fragment or the variant thereof of any of embodiments 40-78, or the bispecific antibody of any of embodiments 79-87, the nucleic acid molecule of embodiment 88, the vector of embodiment 89, the cell of embodiment 90 and/or the pharmaceutical composition of embodiment 92 in manufacture of a drug for relieving or treating tumors.
94. Use according to embodiment 93, wherein the tumor includes colon cancer.
95. A method of inhibiting the binding of PD-L1 protein to PD-1 protein, including administering the antibody, the antigen binding fragment or the variant thereof of any of embodiments 1-39, the antibody, the antigen binding fragment or the variant thereof of any of embodiments 40-78, or the bispecific antibody of any of embodiments 79-87, the nucleic acid molecule of embodiment 88, the vector of embodiment 89, the cell of embodiment 90 and/or the pharmaceutical composition of embodiments 92.
96. A method of enhancing the function of T cells, including administering the antibody, the antigen binding fragment or the variant thereof of any of embodiments 1-39, the antibody, the antigen binding fragment or the variant thereof of any of embodiments 40-78, or the bispecific antibody of any of embodiments 79-87, the nucleic acid molecule of embodiment 88, the vector of embodiment 89, the cell of embodiment 90 and/or the pharmaceutical composition of embodiment 92.

Not to be limited by any theory, the following examples are only to illustrate the working methods of the apparatus, method and system of the present application, but not to limit the scope of the present application invention.

EXAMPLES

Example 1. Screening of Anti-PD-L1 Antibody by Use of Phage Antibody Library

Human PD-L1-Fc protein (Origincell Therapeutics Co., Ltd.) as antigen was used to sort the phage natural human antibody library (Origincell Therapeutics Co., Ltd.). The ELISA tube was coated with a CBS buffer containing 20 µg/ml (the first and the second rounds) or 10 µg/ml (the third and the fourth rounds) of PD-L1 protein at 4° C. overnight. The tube was then washed with a PBS buffer. 10% skimmed milk powder was added to block the ELISA tube, and then 1 ml of blocked phage was added and incubated at room temperature (20±5° C.) for 1 hour. After washing thoroughly with PBST, 800 µl of a Gly-HCl buffer solution at pH 2.2 was added for elution, and then 400 µl of a Tris-HCl buffer solution at pH 8.0 was added immediately for neutralization. Then, the mixture was added to 20 ml of E. coli SS320 in the logarithmic growth phase with an OD value of about 0.8, mixed well and stood at 37° C. for 1 hour. 500 µl of microbial solution was taken for measuring the phage titer and glycerin was used to protect the microbials, and the remaining microbial solution was used to coat the plate and cultivated at 37° C. overnight. On the next day, the bacteria on the plate were proportionally inoculated to 80 ml of 2YT-Amp medium, so that the microbial solution has an OD value of 0.2, and cultured for several hours. When the OD value reached 0.8, 160 µl of helper phage was added, mixed well, and stood at 37° C. for 1 hour. Then, IPTG and Kan antibiotics were added and cultured with shaking at 250 rpm at 30° C. overnight. Subsequently, the supernatant was collected for precipitation of the phage by PEG/NaCl solution, which was re-suspended in 1.5 ml of PBS buffer for enrichment screening.

96-well ELISA plates were coated with solutions containing 1 µg/ml of human PD-L1-Fc protein (Origincell Therapeutics Co., Ltd.) and mouse PD-L1-Fc protein (M5251, purchased from ACROBiosystems Inc.) at 4° C. overnight. The plate was then blocked with 10% skimmed milk powder at non-specific binding sites. After thorough washing, the monoclonal phage supernatant was taken and added to the 96-well plates and incubated at 37° C. for 2 hours. After thorough washing, HRP-labeled anti-M13 antibody (27-9421-01, GE healthcare) was added to each well, and reacted at 37° C. for 45 minutes. After washing thoroughly, TMB was added to each well for color development. After reacting at room temperature (20±5° C.) for 5-10 minutes, sulfuric acid was added to each well to stop the reaction. A microplate reader is used to measure the OD value of each well at 450 nm.

A phage antibody clone 1B10 which could specifically bind to both human PD-L1 and mouse PD-L1 was identified by ELISA. Sequencing results show that the nucleotide sequence encoding the heavy chain variable region VH of the phage antibody 1B10 is shown in SEQ ID NO: 1, and the amino acid sequence of the heavy chain variable region VH of the phage antibody 1B10 is shown in SEQ ID NO: 2; the nucleotide sequence encoding the light chain variable region VL of the phage antibody 1B10 is shown in SEQ ID NO: 3, and the amino acid sequence of the light chain variable region VL of the phage antibody 1B10 is shown in SEQ ID NO: 4.

Example 2. Expression and Purification of Anti-PD-L1 Fully Human Intact Antibody A primer was designed for PCR amplification of the VH of the phage antibody 1B10, and the PCR product was cloned by recombination into the pCMV-IgG1NDL vector which was double digested with AgeI and SalI. A design primer was designed for PCR amplification of the VL of the phage antibody 1B10, and the PCR product was cloned by recombination into a pCMV-λ vector which was double digested with AgeI and BsiWI. After sequencing exactly, the heavy chain and the light chain expression vectors were co-transfected into 293F cells for transient expression, and purified by ProteinA column to obtain an intact IgG1,λ antibody of the phage antibody 1B10. This anti-PD-L1 fully human antibody was named YN-002.

The sequencing results show that the nucleotide sequence of the VH encoding the antibody YN-002 is shown in SEQ ID NO: 1, and the amino acid sequence of VH of the antibody YN-002 is shown in SEQ ID NO: 2. The nucleotide sequence of VL encoding the antibody YN-002 is shown in SEQ ID NO: 3, and the amino acid sequence of VL of the antibody YN-002 is shown in SEQ ID NO: 4. The nucleotide sequence of the heavy chain encoding the antibody YN-002 is shown in SEQ ID NO: 5, and the amino acid sequence of the heavy chain of YN-002 is shown in SEQ ID NO: 6. The nucleotide sequence encoding the light chain of the antibody YN-002 is shown in SEQ ID NO: 7, and the amino acid sequence of light chain of the antibody YN-002 is shown in SEQ ID NO: 8.

Example 3. Germline Version of Anti-PD-L1 Fully Human Antibody YN-002

By comparing the antibody YN-002 heavy chain immunoglobulin sequence with the known human germline immunoglobulin heavy chain sequence, it was confirmed that the antibody YN-002 heavy chain used the VH segment from human germline IGHV1-69*09, the D segment from human germline IGHD5-18*01, and JH segment from human germline IGHJ4*02.

By comparing the light chain immunoglobulin sequence of the antibody YN-002 with the known human germline immunoglobulin light chain sequence, it was confirmed that the light chain of the antibody YN-002 used the VL segment from human germline IGLV2-14*01, and JL segment from human germline IGLJ2*01.

The sequence of the CDR region of the antibody YN-002 was analyzed by the Kabat system (see FIG. 1).

The sequencing results show that the amino acid sequences of LCDR1-3 of the antibody YN-002 are shown in SEQ ID NO: 54, SEQ ID NO: 60 and SEQ ID NO: 63, respectively; and the amino acid sequences of HCDR1-3 are shown in SEQ ID NO: 46, SEQ ID NO: 48 and SEQ ID NO: 50, respectively.

To minimize the immunogenicity of the antibody YN-002, some amino acid residues could be mutated back to the germline sequence. The antibody YN-003 is a germline version of the antibody YN-002, which is prepared by mutating one amino acid in the FR1 region of the YN-002 heavy chain variable region back to the germline sequence, and mutating 1 amino acid in the FR2 region and 6 amino acids in the FR3 region in the YN-002 light chain variable region back to the germline sequence (see FIG. 1). The heavy chain expression vector of the anti-PD-L1 fully human antibody YN-003 is obtained by site-directed mutagenesis using a mutation kit (Tiangen Point Mutation Kit, KM101) based on the above-constructed YN-002 heavy chain expression plasmid. The YN-003 light chain expression vector is obtained by site-directed mutagenesis using a mutation kit (Tiangen Point Mutation Kit, KM101) based on the YN-002 light chain expression plasmid.

The amino acid sequence of the antibody YN-003 VH is shown in SEQ ID NO: 9, which can be obtained by mutating one amino acid residue in the amino acid sequence of the antibody YN-002 VH. The nucleotide sequence encoding YN-003 VH is shown in SEQ ID NO: 10. The amino acid sequence of the antibody YN-003 VL is shown in SEQ ID NO: 11, which can be obtained by mutating 7 amino acid residues in the amino acid sequence of the antibody YN-002 VL, and the nucleotide sequence corresponding to YN-003VL is shown in SEQ ID NO: 12. The amino acid sequence of the heavy chain of the antibody YN-003 is shown in SEQ ID NO: 13; the nucleotide sequence encoding the heavy chain of YN-003 is shown in SEQ ID NO: 14; the amino acid sequence of the light chain of the antibody YN-003 is shown in SEQ ID NO: 15; and the nucleotide sequence encoding the light chain of the antibody YN-003 is shown in SEQ ID NO: 16.

For the expression and purification of the YN-003 antibody, please refer to the steps of expressing and purifying the YN-002 antibody in Example 2.

Example 4. Test of Binding Affinity of Anti-PD-L1 Antibody

The binding affinity of the antibody YN-002 and the antibody YN-003 to the recombinant human, *Macaca fascicularis*, mouse, and canine PD-L1 proteins was measured by a molecular interaction analyzer (Octet RED384, purchased from Pall ForteBio Analytics Co., Ltd.). The following proteins were labeled with biotin (EZ-Link Sulfo-NHS-LC-Biotin, Pierce, 21327): recombinant human PD-L1-Fc, recombinant *Macaca fascicularis* PD-L1-Fc (90251-C02H, purchased from Sino Biological Inc.), recombinant mouse PD-L1-Fc (M5251, purchased from ACROBiosystems Inc.), recombinant dog PD-L1-Fc (70110-D02H, purchased from Sino Biological Inc.). The antigen-antibody binding kinetics were analyzed by a biofilm interference (BLI) technology, using a molecular interaction analyzer (Octet RED384, purchased from Pall ForteBio Analytics Co., Ltd.) and using a PBS buffer containing 0.1% BSA and 0.02% Tween 20. A biotin-coupled antigen protein with a concentration of 50 nM was fixed with the SA sensor (Pall ForteBio Analytics Co., Ltd.), and bound at 1500 rpm for 10 minutes; then it was bound with the double-diluted antibody solution at 1500 rpm for 10 minutes; and finally dissociated at 1500 rpm for 10 minutes. The obtained results would be analyzed by Octet Data Analysis 9.0 software (Pall ForteBio Analytics Co., Ltd.) to give the $K_D$, $K_{on}$ (1/Ms) and $K_{off}$ (1/s).

The results of the measured binding affinity of the anti-PD-L1 antibodies YN-002 to YN-003 are shown in Tables 1-4.

TABLE 1

Binding Affinity of PD-L1 Antibody to Human PD-L1-Fc

| Antibody | Human PD-L1-Fc-Biotin | | |
|---|---|---|---|
| | $k_{on}$ (1/Ms) | $k_{off}$ (1/s) | $K_D$ (M) |
| YN-002 | $6.69 \times 10^5$ | $5.94 \times 10^{-4}$ | $8.88 \times 10^{-10}$ |
| YN-003 | $1.50 \times 10^6$ | $6.11 \times 10^{-4}$ | $4.08 \times 10^{-10}$ |

TABLE 2

Binding Affinity of PD-L1 Antibody to Mouse PD-L1-Fc

| Antibody | Mouse PD-L1-Fc-Biotin | | |
|---|---|---|---|
| | $k_{on}$ (1/Ms) | $k_{off}$ (1/s) | $K_D$ (M) |
| YN-002 | $9.77 \times 10^5$ | $1.68 \times 10^{-3}$ | $1.72 \times 10^{-9}$ |
| YN-003 | $1.03 \times 10^6$ | $9.97 \times 10^{-4}$ | $9.96 \times 10^{-10}$ |

TABLE 3

Binding Affinity of PD-L1 Antibody to Macaca Fascicularis PD-L1-Fc

| Antibody | Macaca Fascicularis PD-L1-Fc-Biotin | | |
|---|---|---|---|
| | $k_{on}$ (1/Ms) | $k_{off}$ (1/s) | $K_D$ (M) |
| YN-002 | $1.77 \times 10^6$ | $1.90 \times 10^{-3}$ | $1.07 \times 10^{-9}$ |
| YN-003 | $2.08 \times 10^6$ | $1.36 \times 10^{-3}$ | $6.54 \times 10^{-10}$ |

TABLE 4

Binding Affinity of PD-L1 Antibody to Dog PD-L1-Fc

| Antibody | Dog PD-L1-Fc-Biotin | | |
|---|---|---|---|
| | $k_{on}$ (1/Ms) | $k_{off}$ (1/s) | $K_D$ (M) |
| YN-002 | $1.02 \times 10^6$ | $7.59 \times 10^{-4}$ | $7.43 \times 10^{-10}$ |
| YN-003 | $8.64 \times 10^5$ | $5.14 \times 10^{-4}$ | $5.94 \times 10^{-10}$ |

Example 5: PD-L1 Antibody Inhibits the Binding of Human PD-L1 and Human PD-1

The human PD-1-Fc protein (ACROBiosystems Inc., H5257) was labeled with biotin (EZ-Link Sulfo-NHS-LC-Biotin, Pierce, 21327). The human PD-1-Fc labeled with a subsaturated concentration of biotin was added into $1 \times 10^6$/ml of the CHO cells that stably expressed human PD-L1, and then each antibody diluted in five-fold ratio was added, mixed well and incubated (4° C., 1 hr). After cell washing, Streptavidin R-PE Conjugate (life technology, SA10041) was added and incubated (4° C., 30 min). After cell washing, the fluorescence intensity was detected by a flow cytometer (Intellicyt iQue Screener). The results are shown in FIG. 2: both YN-002 and YN-003 can effectively inhibit the binding of human PD-1 to CHO cells expressing human PD-L1.

Example 6: PD-L1 Antibody Inhibits the Binding of *Macaca Fascicularis* PD-L1 to *Macaca fascicularis* PD-1

The capacity of anti-PD-L1 antibodies YN-002 and YN-003 for blocking the binding of *Macaca fascicularis* PD-L1-Fc (Sino Biological Inc., 90251-C02H) to *Macaca fascicularis* PD-1-Fc (Sino Biological Inc., 90311-C02H) was assessed by the Octet RED384 instrument ((Pall ForteBio Analytics Co., Ltd.). First, the *Macaca fascicularis* PD-1-Fc was labeled with biotin (EZ-Link Sulfo-NHS-LC-Biotin, Pierce, 21327). The binding kinetic analysis of PD-L1 antibody for inhibiting the binding of *Macaca fascicularis* PD-L1 to *Macaca fascicularis* PD-1 was performed by the biofilm interference (BLI) technology, using the fortebio octet RED384 instrument (PALL) molecular interaction analyzer (both the antigen and the antibody were diluted with 0.1% BSA and 0.02% Tween 20 in a PBS buffer). A 100 nM biotin-coupled recombinant human PD-1-Fc was fixed with the SA sensor at 1500 rpm/min and bound for 10 min. The *Macaca fascicularis* PD-L1 at a final concentration of 75 nM was mixed with a three-fold diluted antibody solution, incubated for 60 minutes and then combined on the machine for 10 minutes at 1500 rpm/min, and finally dissociated for 10 minutes at 1500 rpm/min. The obtained results will be subject to data analysis by Octet Data Analysis 9.0 software (Pall ForteBio Analytics Co., Ltd.). The results are shown in FIG. 3: both YN-002 and YN-003 can effectively inhibit the binding of *Macaca fascicularis* PD-L1-Fc to *Macaca fascicularis* PD-1-Fc.

Example 7: PD-L1 Antibody Inhibiting the Binding of Mouse PD-L1 to Mouse PD-1

Figure 4:
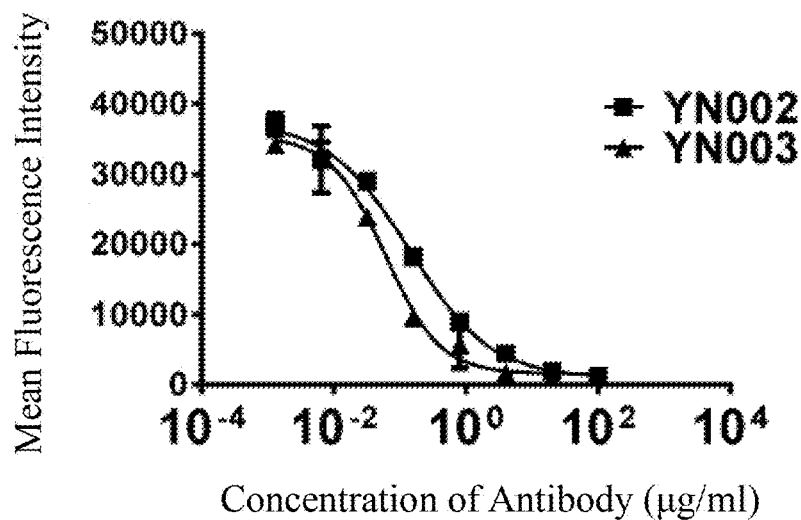
FIG. 4 shows the results of the PD-L1 antibody of the present application inhibiting the binding of the mouse PD-L1 to the mouse PD-1.

Mouse PD-1-Fc (ACROBiosystems Inc., M5259) was labeled with biotin (EZ-Link Sulfo-NHS-LC-Biotin, Pierce, 21327), mouse PD-1-Fc labeled with a subsaturated concentration of biotin was added into $1 \times 10^6$/ml of CHO cells that stably expressed mouse PD-L1, and then each antibody diluted in five-fold ratio was added, mixed well and incubated (4° C., 1 hr). After cell washing, Streptavidin R-PE Conjugate (life technology, SA10041) was added and incubated (4° C., 30 min). After cell washing, the fluorescence intensity was detected by flow cytometer (Intellicyt iQue Screener). The results are shown in FIG. 4: both YN-002 and YN-003 can effectively inhibit the binding of mouse PD-1 to the CHO cells expressing mouse PD-L1.

Example 8: Studies of Antitumor Effect of Anti-PD-L1 Monoclonal Antibody in Colon Cancer-Bearing Mice On Day 0, 6-8 week old C57BL/6 female mice were subcutaneously inoculated with $3 \times 10^6$ MC38 mouse colorectal cancer cells (Shanghai Linyuan Biological Technology Co., Ltd.). On Day 3, the mice were evenly divided into 7 groups with 8-9 mice in each group. The tumor-bearing mice in each group were intraperitoneally injected with the human antibody IgG-Fc protein (10 mg/kg, twice per week, two weeks in total), YN-003 antibody (10 mg/kg, twice per week, two weeks in total), Atezolizumab (10 mg/kg, twice per week, two weeks in total), respectively. The mice in each group were regularly observed for the change of body weight and tumor size. The experimental results show: as compared with the control IgG1-Fc, both YN-003 and Atezolizumab can effectively inhibit the tumor growth, wherein the antitumor effect of YN-003 is more significant (FIG. 5).

Example 9: Screening Anti-CD137 Antibody by Phage Antibody Library

The CD137 protein (purchased from Sino Biological Inc.) was used as an antigen to sort the phage natural human antibody library (Origincell Therapeutics Co., Ltd.). The ELISA tube was coated with a CBS buffer containing 20 μg/ml (the first and the second rounds) or 10 μg/ml (the third and the fourth rounds) of CD137 protein at 4° C. overnight. The tube was then washed with a PBS buffer. 10% skimmed milk powder was added to block the ELISA tube, and then 1 ml of blocked phage was added and incubated at room temperature (20±5° C.) for 1 hour. After washing thoroughly with PBST, 800 μl of a Gly-HCl buffer solution at pH 2.2 was added for elution, and then 400 μl of a Tris-HCl buffer solution at pH 8.0 was added immediately for neutralization. Then, the mixture was added to 20 ml of *E. coli* SS320 in the logarithmic growth phase with an OD value of about 0.8, mixed well and stood at 37° C. for 1 hour. 500 μl of microbial solution was taken for measuring the phage titer and glycerin was used to protect the microbials, and the remaining microbial solution was used to coat the plate and cultivated at 37° C. overnight. On the next day, the bacteria on the plate were proportionally inoculated to 80 ml of 2YT-Amp medium, so that the microbial solution has an OD value of 0.2, and cultured for several hours. When the OD value reached 0.8, 160 μl of helper phage was added, mixed well, and stood at 37° C. for 1 hour. Then, IPTG and Kan antibiotics were added and cultured with shaking at 250 rpm at 30° C. overnight. Subsequently, the supernatant was collected for precipitation of the phage by PEG/NaCl solution, which was re-suspended in 1.5 ml of PBS buffer for enrichment screening.

96-well ELISA plates were coated with solutions containing 1 μg/ml of human CD137 protein at 4° C. overnight. The plate was then blocked with 10% skimmed milk powder at non-specific binding sites. After thorough washing, the monoclonal phage supernatant was taken and added to the 96-well plates and incubated at 37° C. for 2 hours. After thorough washing, HRP-labeled anti-M13 antibody (27-9421-01, GE healthcare) was added to each well, and reacted at 37° C. for 45 minutes. After washing thoroughly, TMB was added to each well for color development. After reacting at room temperature (20±5° C.) for 5-10 minutes, sulfuric acid was added to each well to stop the reaction. A microplate reader is used to measure the OD value of each well at 450 nm.

A phage antibody clone 1A6 which could specifically bind to human CD137 was identified by ELISA, and the VH and VL gene sequences were obtained by sequencing. The sequencing results showed that the nucleotide sequence encoding the VH of the phage antibody 1A6 is shown in SEQ ID NO: 17, the amino acid sequence of the VH of the phage antibody 1A6 is shown in SEQ ID NO: 18; the nucleoside acid sequence encoding the VL of the phage antibody 1A6 is shown in SEQ ID NO: 19, and the amino acid sequence of VL of the phage antibody 1A6 is shown in SEQ ID NO: 20.

Example 10. Expression and Purification of Anti-CD137 Fully Human Intact Antibody A primer was designed for the PCR amplification of the VH of phage antibody 1A6. The PCR product was cloned by recombination into the pCMV-IgG2 vector double digested with AgeI and SalI. A primer was designed for the PCR amplification of the VL of phage antibody 1A6, and the PCR product was cloned by recombination into pCMV-λ vector digested with AgeI and BsiWI. After correct sequencing, the heavy chain and the light chain expression vectors were co-transfected into 293F cells for transient expression, and purified by ProteinA column. The intact IgG2, λ antibody of 1A6, the anti-CD137 fully human antibody, was named YN-005.

The sequencing results showed that the amino acid sequence of the antibody YN-005 VH is shown in SEQ ID NO: 18, the nucleotide sequence encoding the antibody YN-005 VH is shown in SEQ ID NO: 17; and the amino acid sequence of the antibody YN-005 VL is shown in SEQ ID NO: 20, and the nucleotide sequence encoding the antibody YN-005 VL is shown in SEQ ID NO: 19. The amino acid sequence of the heavy chain of the antibody YN-005 is shown in SEQ ID NO: 21, the nucleotide sequence encoding the heavy chain of the antibody YN-005 is shown in SEQ ID NO: 22; the amino acid sequence of the light chain of the antibody YN-005 is shown in SEQ ID NO: 23, and the nucleotide sequence encoding the light chain of the antibody YN-005 is shown in SEQ ID NO: 24.

Example 11: Germline Version of Anti-CD137 Fully Human Antibody YN-005

By comparing the antibody YN-005 heavy chain immunoglobulin sequence with the known human germline immunoglobulin heavy chain sequence, it was confirmed that the antibody YN-005 heavy chain utilized the VH segment from human germline IGHV3-23*04, the D segment from human germline IGHD7-27*01 and the JH segment from human germline IGHJ3*02.

By comparing the YN-005 light chain immunoglobulin sequence with the known human germline immunoglobulin light chain sequence, it was confirmed that the antibody YN-005 light chain utilized the VL segment from human germline IGLV1-44*01 and the JL segment from human germline IGLJ1*01.

The Kabat system was used to analyze the sequence of the CDR region of the antibody YN-005 (see FIG. 6), and the sequencing results show that the amino acid sequence of HCDR1-3 of the antibody YN-005 is shown in SEQ ID NO: 77, SEQ ID NO: 78 and SEQ ID NO: 79, respectively. The amino acid sequence of the LCDR1-3 of the antibody YN-005 is shown in SEQ ID NO: 80, SEQ ID NO: 81 and SEQ ID NO: 82, respectively.

In order to minimize the immunogenicity of the antibody YN-005, some amino acid residues can be mutated back to the germline sequence. The antibody YN-006 is a germline version of the antibody YN-005, which is prepared by mutating one amino acid in the FR1 region in the YN-005 heavy chain variable region back to the germline sequence (see FIG. 6). The heavy chain expression vector of the anti-CD137 fully human antibody YN-006 is obtained by site-directed mutagenesis using a mutation kit (Tiangen Point Mutation Kit, KM101) based on the above-constructed heavy chain express plasmid of YN-005.

Sequencing shows that the amino acid sequence of the antibody YN-006 VH is shown in SEQ ID NO: 25, and the nucleotide sequence encoding the YN-006 VH is shown in SEQ ID NO: 26. The amino acid sequence of the antibody YN-006 VL is shown in SEQ ID NO: 20, and the nucleotide sequence encoding the YN-006 VL is shown in SEQ ID NO: 19. The amino acid sequence of the antibody YN-006 heavy chain is shown in SEQ ID NO: 27; the nucleotide sequence encoding the antibody YN-006 heavy chain is shown in SEQ ID NO: 28; and the amino acid sequence of the antibody YN-006 light chain is shown in SEQ ID NO: 23, and the nucleotide sequence encoding the YN-006 light chain is shown in SEQ ID NO: 24.

For the expression and purification of the YN-006 antibody, please refer to the specific steps of expressing and purifying YN-005 antibody in Example 9.

Example 12: Determination of Binding Affinity of Anti-CD137 Antibody

The binding affinity of the antibody YN-005 and the antibody YN-006 to the recombinant human CD137-His protein (Origincell Therapeutics Co., Ltd.) was measured by a molecular interaction analyzer (Octet RED384, purchased from Pall ForteBio Analytics Co., Ltd.). The antigen-antibody binding kinetics were analyzed by the biofilm interference (BLI) technology, using a molecular interaction analyzer (Octet RED384, purchased from Pall ForteBio Analytics Co., Ltd.) and using a PBS buffer containing 0.1% BSA and 0.02% Tween 20. The antibody with a concentration of 50 nM was fixed with the AHC sensor, and bound at 1500 rpm for 5 minutes; then it was bound with the double-diluted recombinant CD137-His protein antigen solution (100, 50, 25, 12.5, 6.25, 3.125, 1.56 nM) at 1500 rpm for 5 minutes; and finally dissociated at 1500 rpm for 10 minutes. The AHC sensor is regenerated by glycine pulses and then reused. The obtained results would be analyzed by Octet Data Analysis 9.0 software (Pall ForteBio Analytics Co., Ltd.) to give the $K_D$, $K_{on}$ (1/Ms) and $K_{off}$ (1/s). The measured results of the binding affinity of the CD137 antibodies YN-005 and YN-006 are shown in Table 5.

TABLE 5

Affinity of CD137 Antibody to Human CD137-His

| Antibody | CD137-His | | |
|---|---|---|---|
| | $K_{on}$ (1/Ms) | $K_{off}$ (1/s) | $K_D$ (M) |
| YN-005 | $9.38 \times 10^4$ | $4.55 \times 10^{-5}$ | $4.85 \times 10^{-10}$ |
| YN-006 | $9.68 \times 10^4$ | $1.33 \times 10^{-5}$ | $1.37 \times 10^{-10}$ |

Figure 7:
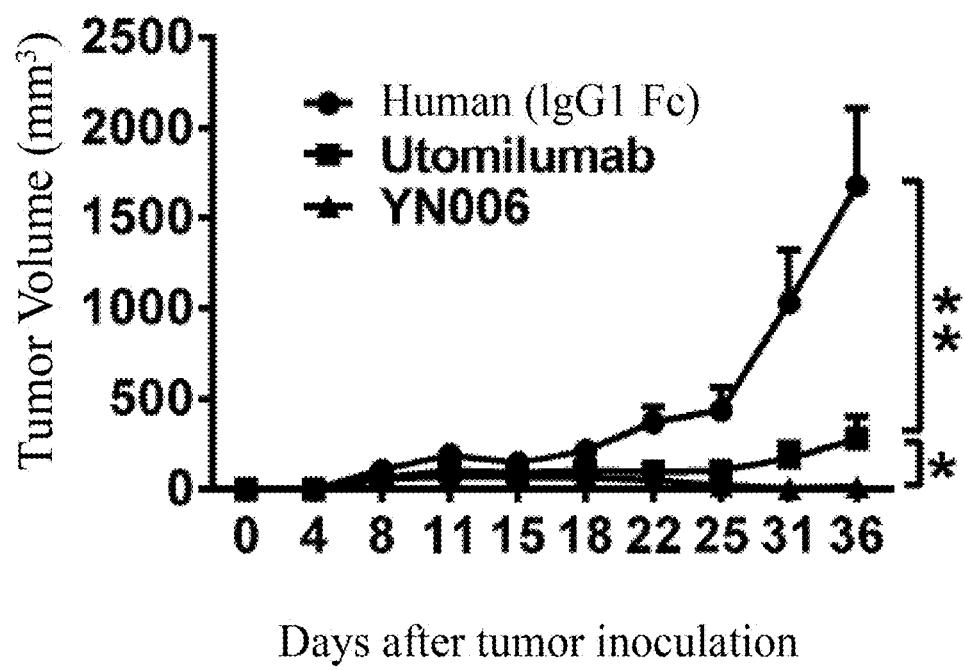
FIG. 7 shows the effect of the CD137 antibody of the present application on the MC38 tumor growth in C57BL/6 female mouse with human CD137 gene knocked-in (*, P<0.05; **, P<0.01; Unpaired t-test).

Example 13: Studies of Antitumor Effect of CD137 Monoclonal Antibody in Colon Cancer-Bearing mice On Day 0, 6-8 week old C57BL/6 female mice with human CD137 gene (B-hTNFRSF9 (4-1BB) mice, purchased from Beijing BioCytogen Co., Ltd.) were subcutaneously inoculated with $1.5 \times 10^6$ MC38 mouse colorectal cancer. On Day 3, the mice were evenly divided into 3 groups with 7 mice in each group. The tumor-bearing mice in each group were intraperitoneally injected with the human antibody IgG-Fc protein (3 mg/kg, twice per week, two weeks in total), CD137 antibody YN-006 antibody (3 mg/kg, twice per week, two weeks in total), and CD137 antibody Utomilumab (3 mg/kg, twice per week, two weeks in total), respectively. The mice in each group were regularly observed for the change of body weight and tumor size. The experimental results show: as compared with the control IgG1-Fc, both YN-006 and Utomilumab can effectively inhibit the tumor growth, and it is worth noting that the antitumor effect of YN-006 is more significant than Utomilumab (e.g., as shown in FIG. 7).

Example 14: Construction of Anti-PD-L1/CD137 Bispecific Antibody YN-007

The first polypeptide gene of the anti-PD-L1/CD137 bispecific antibody YN-007 was constructed by a molecular cloning method, such as, Overlap PCR, Site-directed Mutation, or the like using the heavy chain gene of the anti-PD-L1 antibody YN-003 and the heavy chain and the light chain genes of the anti-human CD137 antibody YN-006, and cloned by combination into the pCMV-IgG1AEM vector double digested with AgeI and BamHI to construct the expression vector of the first polypeptide of YN-007.

The second polypeptide gene of YN-007 is the same as that of the light chain gene of YN-003. The expression vector of the second polypeptide of YN-007 is the above-constructed expression vector of the light chain of YN-003.

After correct sequencing, the expression vectors of the first polypeptide and the second polypeptide were co-transfected into 293F cells for transient expression, and purified by Protein A Column to obtain the anti-PD-L1/CD137 bispecific antibody YN-007.

The nucleotide sequence encoding the first polypeptide of the antibody YN-007 is shown in SEQ ID NO: 29, and the amino acid sequence of the first polypeptide of the antibody YN-007 is shown in SEQ ID NO: 30; the nucleotide sequence encoding the second polypeptide of the antibody YN-007 is shown in SEQ ID NO: 16, and the amino acid sequence of the second polypeptide of the antibody YN-007 is shown in SEQ ID NO: 15.

Example 15: Determination of Binding Affinity of Anti-PD-L1/CD137 Bispecific Antibody YN-007

The binding affinity of the anti-PD-L1/CD137 bispecific antibody YN-007 to the recombinant human PD-L1-Fc protein and the recombinant mouse PD-L1-Fc was measured by a molecular interaction analyzer (Octet RED384, purchased from Pall ForteBio Analytics Co., Ltd.). The recombinant human PD-L1-Fc protein and the recombinant mouse PD-L1-Fc were labeled with biotin (EZ-Link Sulfo-NHS-LC-Biotin, Pierce, 21327). The antigen-antibody binding kinetics were analyzed by the biofilm interference (BLI) technology, using a molecular interaction analyzer (Octet RED384, purchased from Pall ForteBio Analytics Co., Ltd.) and using a PBS buffer containing 0.1% BSA and 0.02% Tween 20. A biotin-coupled antigen protein with a concentration of 50 nM was fixed with the SA sensor (Pall ForteBio Analytics Co., Ltd.), and bound at 1500 rpm for 10 minutes; then it was bound with the double-diluted YN-007 antibody solution at 1500 rpm for 10 minutes; and finally dissociated at 1500 rpm for 10 minutes. The obtained results would be analyzed by Octet Data Analysis 9.0 software (Pall ForteBio Analytics Co., Ltd.) to give the $K_D$, $K_{on}$ (1/Ms) and $K_{off}$ (1/s).

The measured results of the binding affinity of YN-007 to human PD-L1-Fc are shown in Table 6.

The measured results of the binding affinity of YN-007 to mouse PD-L1-Fc were shown in Table 7.

TABLE 6

Binding Affinity of Anti-PD-L1/CD137 Bispecific Antibody YN-007 to Human PD-L1-Fc

| Antibody | Human PD-L1-Fc-Biotin | | |
|---|---|---|---|
| | $k_{on}$ (1/Ms) | $k_{off}$ (1/s) | $K_D$ (M) |
| YN-007 | $1.13 \times 10^6$ | $5.92 \times 10^{-4}$ | $5.25 \times 10^{-10}$ |

TABLE 7

Binding Affinity of Anti-PD-L1/CD137 Bispecific Antibody YN-007 to Mouse PD-L1-Fc

| Antibody | Mouse PD-L1-Fc-Biotin | | |
|---|---|---|---|
| | $k_{on}$ (1/Ms) | $k_{off}$ (1/s) | $K_D$ (M) |
| YN-007 | $8.1 \times 10^5$ | $1.09 \times 10^{-3}$ | $1.34 \times 10^{-9}$ |

The binding affinity of the anti-PD-L1/CD137 bispecific antibody YN-007 to the recombinant human CD137-His protein was measured by a molecular interaction analyzer (Octet RED384, purchased from Pall ForteBio Analytics Co., Ltd.). The antigen-antibody binding kinetics were analyzed by the biofilm interference (BLI) technology, using a molecular interaction analyzer (Octet RED384, purchased from Pall ForteBio Analytics Co., Ltd.) and using a PBS buffer containing 0.1% BSA and 0.02% Tween 20. The antibody with a concentration of 50 nM was fixed with the AHC sensor, and bound at 1500 rpm for 5 minutes; then it was bound with the double-diluted recombinant human CD137-His protein antigen solution (100, 50, 25, 12.5, 6.25, 3.125, 1.56 nM) at 1500 rpm for 5 minutes; and finally dissociated at 1500 rpm for 10 minutes. The AHC sensor was regenerated by glycine pulses and then reused. The obtained results would be analyzed by Octet Data Analysis 9.0 software (Pall ForteBio Analytics Co., Ltd.) to calculate the binding strength between the antigen and the antibody, to give the $K_D$, $K_{on}$ (1/Ms) and $K_{off}$ (1/s).

The measured results of the binding affinity of anti-PD-L1/CD137 bispecific antibody YN-007 to human CD137 are shown in Table 8.

TABLE 8

Binding Affinity of Anti-PD-L1/CD137 Bispecific
Antibody YN-007 to Human CD137-His

| | Human CD137-His | | |
|---|---|---|---|
| Antibody | $K_{on}$ (1/Ms) | $K_{off}$ (1/s) | $K_D$ (M) |
| YN-007 | $8.96 \times 10^4$ | $9.83 \times 10^{-5}$ | $1.1 \times 10^{-9}$ |

Example 16: Affinity Maturation of PD-L1 Antibody YN-003

A primer was designed to construct the single-chain antibody (ScFv) gene of the PD-L1 antibody YN-003 by overlapping PCR, and cloned into the pDF phagemid vector, and denoted as pDF-YN-003 ScFv. The pDF-YN-003 ScFv was used as a template to design a degenerate primer to randomize 6 CDR regions (including some amino acid residues in the CDR regions and individual amino acid residues in the FR regions adjacent to the CDR regions) of the antibody YN-003 by overlapping PCR, respectively (as shown in FIG. 8).

The CDR region-randomized scFv gene fragments obtained by overlapping PCR were double digested with BssHII and NheI, and then ligated with the pDF phagemid vector double digested by BssHII and NheI. 1 μg of the ligation product was electroporated into TG1 electro-competent cells, and coated onto a 2YT+AG plate after multiple dilutions. On the next day, the lawn was scraped from the plate, and expanded to 300 ml of 2YT+Amp medium. It was cultured at 37° C. to an OD of about 0.8. The helper phage was added and mixed well, stood for 1 hour, and IPTG with a final concentration of 1 mM and 50 μg/ml of Kana were added and shaken at 30° C. overnight. On the next day, the supernatant was collected by centrifugation, and filtered with 0.45 filter. ⅕ volume of PEG-NaCl was added to precipitate phage, and centrifuged to collect the precipitate. 1/10 volume of PBS was used to resuspend the precipitate, and OD260 was measured to calculate the phage pfu. The product was stored at 4° C. The phage antibody library can be used directly for later panning.

The human PD-L1-His protein (Origincell Therapeutics Co., Ltd.) as the antigen was used to sort the above phage antibody library. In ELISA tubes, a CBS buffer was used to coat the antigen PD-L1 (1 ml) with a concentration of 100 nM (the first and the second rounds) or 5 nM (the third round) at 4° C. overnight. On the next day, 2 ml of PBS buffer containing 10% skimmed milk powder was used to block the tube. 1 ml of the blocked phage was added into the tube and incubated for 1 hr at room temperature; washed with PBST for 20 times (the first round), 50 times (the second round) or 100 times (the third round). 800 μl of Gly-HCl buffer (pH2.2) was added for elution, and 400 μl of Tris-HCl buffer (pH 8.0) was immediately added for neutralization. It was added to 20 ml of *E. coli* TG1 with logarithmic growth phase OD of about 0.8, mixed well and stood at 37° C. for 1 hr. 500 μl was taken for determining the phage titer and glycerol was used to protect the microbials. The remaining microbial liquid was spread on the plate and incubated at 37° C. in the incubator overnight. On the next day, the microbials on the plate were scraped and inoculated in 80 ml of 2YT-Amp medium at a certain proportion to allow the OD to be 0.2. The mixture were incubated for several hours until the OD reached 0.8. 160 μl of helper phage was added, mixed well and stood at 37° C. for 1 h. IPTG and Kan antibiotics were added, and incubated under shaking at 250 rpm at 30° C. overnight. The supernatant was collected and treated with PEG/NaCl solution for precipitating the phages, which were resuspended in 1.5 ml of PBS buffer. The resuspended phage was used for the next round of enrichment screening. After 3 rounds of sorting, a significant enrichment was observed. The sorted phage antibody clones were identified by ELISA: human PD-L1-His protein was coated on a 96-well ELISA plate at a concentration of 1 μg/ml at 4° C. overnight. Then, the non-specific binding sites were blocked with 10% skimmed milk powder. After sufficient washing, the monoclonal phage supernatant was added to a 96-well plate and incubated at 37° C. for 2 hours. After thorough washing, HRP-labeled anti-M13 antibody (GE healthcare, 27-9421-01) was added and reacted at 37° C. for 45 minutes. After thorough washing, TMB was added to develop color and reacted at room temperature for 5-10 minutes. Finally, the reaction was stopped with sulfuric acid. The OD value of each well was measured at 450 nm, and the phage antibody clone with higher OD450 value was selected for sequencing. After obtaining the heavy chain and the light chain variable region gene sequences of each phage antibody clone, each phage antibody was re-designed as a full-length IgG1,λ antibody: a primer was designed to perform PCR amplification of the VH of each phage antibody clone, and the PCR product was cloned by recombination to the pCMV-IgG1NDL antibody heavy chain expression vector double digested with AgeI and SalI. A primer was designed for PCR amplification of the VL of each phage antibody clone, and the PCR product was cloned into the pCMV-λ antibody light chain expression vector doubled digested with AgeI and BsiWI. After correct sequencing, the heavy chain and the light chain expression vectors of each antibody were co-transfected into 293F cells for transient expression. After 7 days of culture in serum-free medium, the cell culture supernatant was collected and purified by ProteinA column to obtain antibody protein. Purified antibody was dialyzed with PBS, and finally quantified with BCA Protein Assay Kit (Pierce, 23225). The binding affinity of the above full-length antibody against the recombinant human PD-L1-His protein (Origincell Therapeutics Co., Ltd.) by using a molecular interaction analyzer (Octet RED384, purchased from Pall ForteBio Analytics Co., Ltd.). The antigen-antibody binding kinetics were analyzed by the biofilm interference (BLI) technology, using a molecular interaction analyzer (Octet RED384, purchased from Pall ForteBio Analytics Co., Ltd.) and using a PBS buffer containing 0.1% BSA and 0.02% Tween20. The antibody with a concentration of 50 nM was fixed with the AHC sensor, and bound at 1500 rpm for 5 minutes; then bounded with the double-diluted antigen solution (50, 25, 12.5, 6.25, 3.125, 1.56 nM) with 7 concentration gradients at 1500 rpm for 5 minutes, and finally dissociated at 1500 rpm for 10 minutes. The AHC sensor was regenerated by glycine pulses and then reused. The results obtained will be analyzed by Octet Data Analysis 9.0 software (Pall ForteBio Analytics Co., Ltd.) to obtain the $K_D$, $K_{on}$ (1/Ms) and $K_{off}$ (1/s). After screening the obtained mutant clones with increased affinity, the amino acid mutation points with increased affinity in different CDR regions were combined by using methods such as Overlapping PCR, and then the antibody protein was expressed and purified according to the above method and the affinity was determined. After multiple rounds of screening and combination, the top 5 YN-003 antibody mutant clones with high affinity were named YN-035 antibody, YN-036 antibody, YN-037 antibody, YN-038 antibody, and YN-039 antibody, respectively. The affinity values of the 5 antibodies obtained by the above method are shown in Table 9. The results show that the affinity of YN-035 antibody, YN-036 antibody, YN-037 antibody, YN-038 antibody, and YN-039 antibody were all higher than the anti-PD-L1 antibodies Atezolizumab and Avelumab.

TABLE 9

Binding Affinity of PD-L1 Antibody to Human PD-L1-His

Human PD-L1-His

| Antibody | $K_D$ (M) | $K_D$ Error | $K_{on}$ (1/Ms) | $K_{on}$ Error | $K_{off}$ (1/s) | $K_{off}$ Error | Full R^2 |
|---|---|---|---|---|---|---|---|
| Atezolizumab | $9.16 \times 10^{-10}$ | $8.79 \times 10^{-12}$ | $3.78 \times 10^5$ | $1.95 \times 10^3$ | $3.46 \times 10^{-4}$ | $2.80 \times 10^{-6}$ | 0.9984 |
| Avelumab | $1.03 \times 10^{-9}$ | $9.20 \times 10^{-12}$ | $2.96 \times 10^5$ | $1.31 \times 10^3$ | $3.05 \times 10^{-4}$ | $2.37 \times 10^{-6}$ | 0.9991 |
| YN-035 | $4.52 \times 10^{-10}$ | $3.54 \times 10^{-12}$ | $4.27 \times 10^5$ | $1.16 \times 10^3$ | $1.93 \times 10^{-4}$ | $1.42 \times 10^{-6}$ | 0.9995 |
| YN-036 | $4.74 \times 10^{-10}$ | $4.95 \times 10^{-12}$ | $3.69 \times 10^5$ | $1.22 \times 10^3$ | $1.75 \times 10^{-4}$ | $1.73 \times 10^{-6}$ | 0.9994 |
| YN-037 | $3.82 \times 10^{-10}$ | $5.66 \times 10^{-12}$ | $3.55 \times 10^5$ | $1.36 \times 10^3$ | $1.36 \times 10^{-4}$ | $1.94 \times 10^{-6}$ | 0.9991 |
| YN-038 | $4.47 \times 10^{-10}$ | $4.61 \times 10^{-12}$ | $3.50 \times 10^5$ | $1.05 \times 10^3$ | $1.56 \times 10^{-4}$ | $1.54 \times 10^{-6}$ | 0.9995 |
| YN-039 | $4.85 \times 10^{-10}$ | $4.41 \times 10^{-12}$ | $3.56 \times 10^5$ | $1.02 \times 10^3$ | $1.73 \times 10^{-4}$ | $1.49 \times 10^{-6}$ | 0.9995 |

The amino acid sequence of the YN-035 antibody heavy chain variable region (YN-035 VH) is shown in SEQ ID NO: 31, the amino acid sequence of the YN-035 antibody heavy chain is shown in SEQ ID NO: 32, the amino acid sequence of the YN-035 antibody light chain variable region (YN-035 VL) is shown in SEQ ID NO: 33, and the amino acid sequence of the YN-035 antibody light chain is shown in SEQ ID NO: 34.

The amino acid sequence of the YN-036 antibody heavy chain variable region (YN-036 VH) is shown in SEQ ID NO: 35, the amino acid sequence of the YN-036 antibody heavy chain is shown in SEQ ID NO: 36, The amino acid sequence of the YN-036 antibody light chain variable region (YN-036VL) is shown in SEQ ID NO: 33, and the amino acid sequence of the YN-036 antibody light chain is shown in SEQ ID NO: 34.

The amino acid sequence of the YN-037 antibody heavy chain variable region (YN-037 VH) is shown in SEQ ID NO: 35, the amino acid sequence of the YN-037 antibody heavy chain is shown in SEQ ID NO: 36, the amino acid sequence of the YN-037 antibody light chain variable region (YN-037VL) is shown in SEQ ID NO: 37, and the amino acid sequence of the YN-037 antibody light chain is shown in SEQ ID NO: 38.

The amino acid sequence of the YN-038 antibody heavy chain variable region (YN-038 VH) is shown in SEQ ID NO: 35, the amino acid sequence of the YN-038 antibody heavy chain is shown in SEQ ID NO: 36, the amino acid sequence of the YN-038 antibody light chain variable region (YN-038VL) is shown in SEQ ID NO: 39, and the amino acid sequence of the YN-038 antibody light chain is shown in SEQ ID NO: 40.

The amino acid sequence of the YN-039 antibody heavy chain variable region (YN-039VH) is shown in SEQ ID NO: 35, the amino acid sequence of the YN-039 antibody heavy chain is shown in SEQ ID NO: 36, the amino acid sequence of the YN-039 antibody light chain variable region (YN-039 VL) is shown in SEQ ID NO: 41, and the amino acid sequence of the YN-039 antibody light chain is shown in SEQ ID NO: 42.

Figure 10:
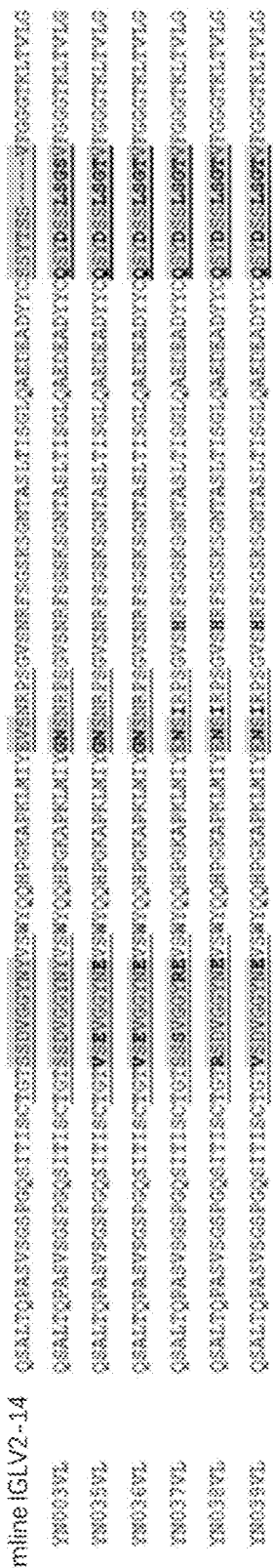
FIG. 10 shows the alignment of the amino acid sequences of the light chain variable regions of the PD-L1 antibody of the present application with the related germline sequences. The underlined are the CDRs determined according to the Kabat definition method, and the shaded parts are the CDRs determined according to the IMGT definition method.

FIG. 9 shows the amino acid sequence alignment of the heavy chain variable regions and related germline sequences of the antibodies YN-003, and YN-035 to YN-039, wherein the underlined are the CDRs determined according to the Kabat definition method. FIG. 10 shows the amino acid sequence alignment of the light chain variable regions and related germline sequences of the antibodies YN-003 and YN-035 to YN-039, wherein the underlined are the CDRs determined according to the Kabat definition. Of those, the amino acid sequence of HCDR1 of the antibody YN-003 is shown in SEQ ID NO: 46, the amino acid sequence of HCDR1 of YN-035 to YN-039 is shown in SEQ ID NO: 47; the amino acid sequence of HCDR2 of the antibody YN-003 and the amino acid sequence of HCDR2 of the antibodies YN-035 to YN-039 is shown in SEQ ID NO: 48; the amino acid sequence of HCDR3 of YN-003 is shown in SEQ ID NO: 50; the amino acid sequence of HCDR3 of YN-035 is shown in SEQ ID NO: 51; and the amino acid sequence of HCDR3 of the antibodies YN-036 to YN-039 is shown in SEQ ID NO: 52.

The amino acid sequence of LCDR1 of the antibody YN-003 is shown in SEQ ID NO: 54, the amino acid sequence of LCDR1 of the antibodies YN-035 and YN-036 is shown in SEQ ID NO: 55, the amino acid sequence of LCDR1 of the antibody YN-037 is shown in SEQ ID NO: 56, the amino acid sequence of LCDR1 of the antibody YN-038 is shown in SEQ ID NO: 57, the amino acid sequence of LCDR1 of the antibody YN-039 is shown in SEQ ID NO: 58; the amino acid sequence of LCDR2 of the antibody YN-003 and the antibodies YN-035 to YN-036 is shown in SEQ ID NO: 60, the amino acid sequence of LCDR2 of the antibodies YN-037 to YN-039 is shown in SEQ ID NO: 61; the amino acid sequence of LCDR3 of the antibody YN-003 is shown in SEQ ID NO: 63; and the amino acid sequence of LCDR3 of antibodies YN-035 to YN-039 is shown in SEQ ID NO: 64.

Figure 11:
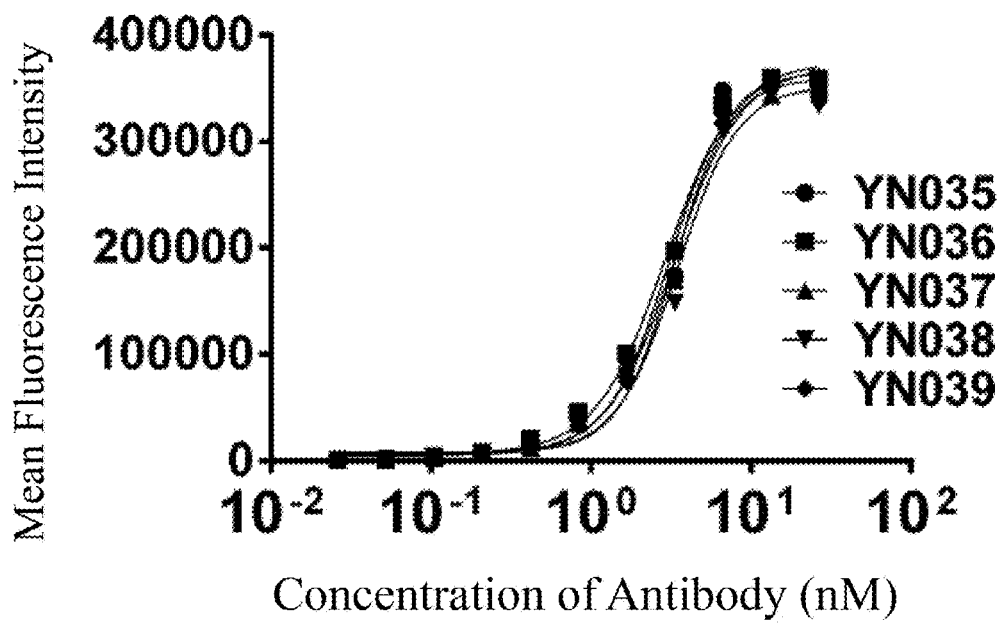
FIG. 11 shows the binding of the PD-L1 antibody of the present application to the CHO cells that stably expresses the human PD-L1.

The binding activity of the PD-L1 antibodies YN-035, YN-036, YN-037, YN-038, YN-039 to human PD-L1 was detected by flow cytometry: to $1 \times 10^6$/ml of the CHO cells that stably expressed human PD-L1 was added individual double-diluted PD-L1 antibodies. The mixture was mixed well and incubated at 4° C. for 1 hr. After cell washing, Goat F(ab')$_2$ Anti-Human IgG-Fc (DyLight 650) (ab98593, Abcam) was added and incubated at 4° C. for 30 min. After cell washing, the fluorescence intensity was detected by a flow cytometer (Intellicyt iQue Screener). The experimental results are shown in FIG. 11: YN-035, YN-036, YN-037, YN-038, YN-039 all can effectively bind to CHO cells expressing human PD-L1.

Figure 12:
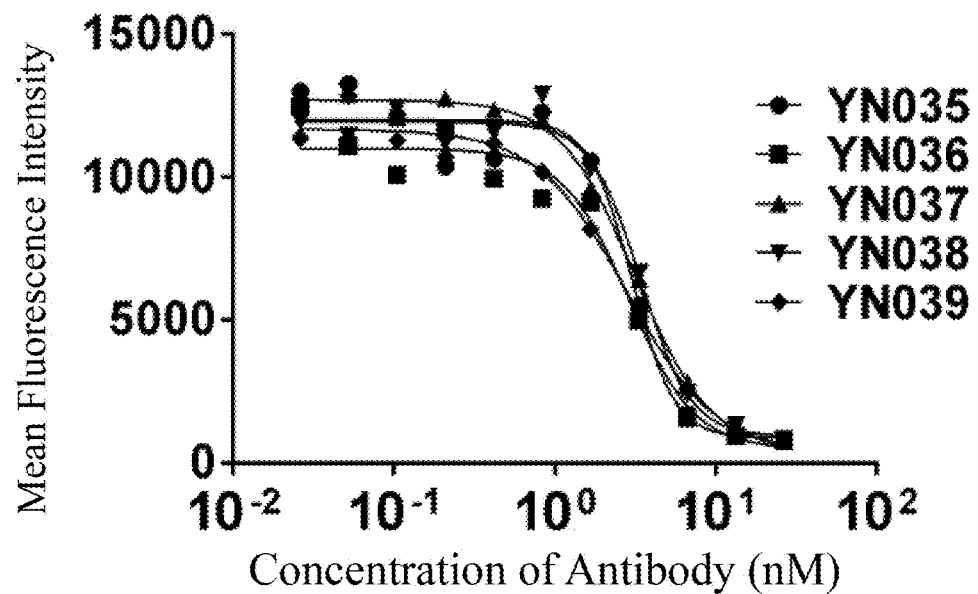
FIG. 12 shows the status that the PD-L1 antibody of the present application inhibits the binding of human PD-1 to human PD-L1.

The inhibitory capacity of the PD-L1 antibodies YN-035, YN-036, YN-037, YN-038, YN-039 to human PD-L1/human PD-1 was detected by flow cytometry: the human PD-1-Fc protein (Origincell Therapeutics Co., Ltd.) was labeled with biotin (EZ-Link Sulfo-NHS-LC-Biotin, Pierce, 21327). The human PD-1-Fc labeled with a subsaturated concentration of biotin was added into $1\times10^6$/ml of the CHO cells that stably expressed human PD-L1, and then individual double-diluted antibodies were immediately added, mixed well and incubated (4° C., 1 hr). After cell washing, Streptavidin R-PE Conjugate (life technology, SA10041) was added and incubated (4° C., 30 min). After cell washing, the fluorescence intensity was detected by a flow cytometer (Intellicyt iQue Screener). The experimental results are shown in FIG. 12: the PD-L1 antibodies YN-035, YN-036, YN-037, YN-038, YN-039 all can effectively inhibit the binding of human PD-1 to CHO cells expressing human PD-L1.

Figure 13:
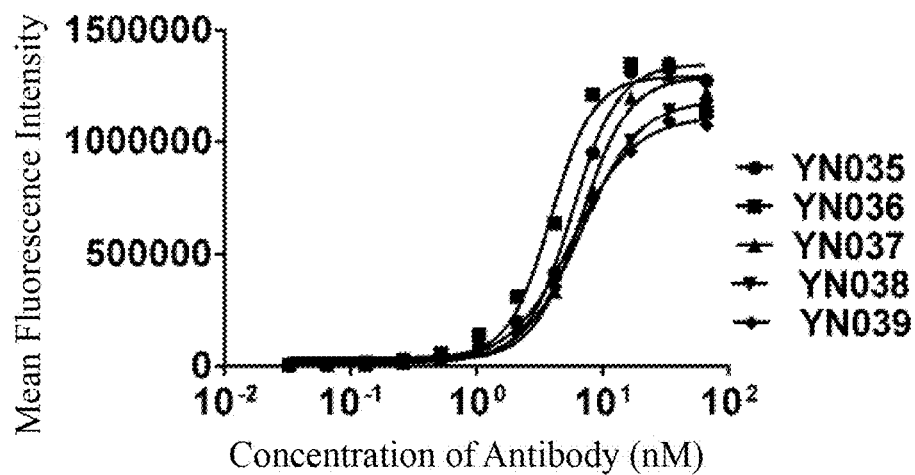
FIG. 13 shows the status that the PD-L1 antibody of the present application binds to the CHO cells that stably expresses mouse PD-L1.

The binding activity of the PD-L1 antibodies YN-035, YN-036, YN-037, YN-038, YN-039 to mouse PD-L1 was detected by flow cytometry: to $1\times10^6$/ml CHO cells that stably expressed mouse PD-L1 were added individual double diluted PD-L1 antibodies. The mixture was mixed well and incubated at 4° C. for 1 hr. After cell washing, Goat F(ab')$_2$ Anti-Human IgG-Fc (DyLight 650) (ab98593) was added and incubated at 4° C. for 30 min. After cell washing, the fluorescence intensity was detected by a flow cytometer (Intellicyt iQue Screener). The experimental results are shown in FIG. 13: YN-035, YN-036, YN-037, YN-038, YN-039 all can effectively bind to the CHO cells expressing mouse PD-L1.

Figure 14:
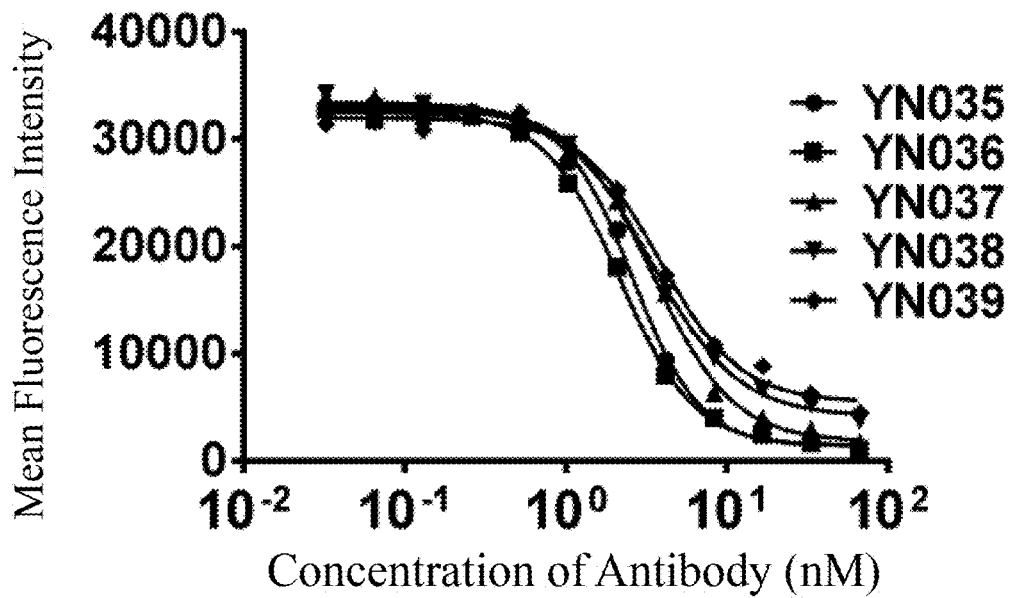
FIG. 14 shows the status that the PD-L1 antibody of the present application inhibits the binding of mouse PD-1 to mouse PD-L1.

The inhibitory capacity of the PD-L1 antibodies YN-035, YN-036, YN-037, YN-038, YN-039 to mouse PD-L1/mouse PD-1 was detected by flow cytometry: mouse PD-1-Fc (Origincell Therapeutics Co., Ltd.) was labeled with biotin (EZ-Link Sulfo-NHS-LC-Biotin, Pierce, 21327). The mouse PD-1-Fc labeled with a subsaturated concentration of biotin was added into $1\times10^6$/ml of the CHO cells that stably expressed mouse PD-L1, and then individual double-diluted antibodies were immediately added, mixed well and incubated (4° C., 1 hr). After cell washing, Streptavidin R-PE Conjugate (life technology, SA10041) was added and incubated (4° C., 30 min). After cell washing, the fluorescence intensity was detected by a flow cytometer (Intellicyt iQue Screener). The results are shown in FIG. 14: the PD-L1 antibodies YN-035, YN-036, YN-037, YN-038, YN-039 all can effectively inhibit the binding of mouse PD-1 to the CHO cells that stably expressed mouse PD-L1.

Example 17: Construction and Identification of Anti-PD-L1/CD137 Bispecific Antibodies YN-051 and YN-052

The first polypeptide gene of anti-PD-L1/CD137 bispecific antibody YN-051 was constructed by molecular cloning method, such as, Overlap PCR, Site-directed Mutation, or the like, using the heavy chain gene of the anti-PD-L1 antibody YN-035 and the heavy chain and the light chain genes of the anti-human CD137 antibody YN-006, and cloned by recombination into the pCMV-IgG1AEM vector double digested with AgeI and BamHI, so as to construct the first polypeptide expression vector of YN-051. The second polypeptide gene of YN-051 is the same as the light chain gene of YN-035. The second polypeptide expression vector of YN-035 is the light chain expression vector of YN-035.

After correct sequencing, the first polypeptide and the second polypeptide expression vectors of the anti-PD-L1/CD137 bispecific antibody YN-051 were co-transfected into 293F cell for transient expression. After culturing in serum-free medium for 7 days, the cell culture supernatant was collected and purified by Protein A column to obtain the antibody protein. The purified antibody was dialyzed with PBS, and finally quantified with BCA Protein Assay Kit (Pierce, 23225).

The amino acid sequence of the first polypeptide of YN-051 is shown in SEQ ID NO: 43, and the amino acid sequence of the second polypeptide of YN-051 is shown in SEQ ID NO: 34.

The first polypeptide gene of anti-PD-L1/CD137 bispecific antibody YN-052 was constructed by molecular cloning method, such as, Overlap PCR, Site-directed Mutation, or the like, using the heavy chain gene of the anti-PD-L1 antibody YN-036 and the heavy chain and the light chain genes of the anti-human CD137 antibody YN-006, and cloned by recombination into the pCMV-IgG1AEM vector double digested with AgeI and BamHI, so as to construct the first polypeptide expression vector of YN-052. The second polypeptide gene of YN-052 is the same as the light chain gene of YN-036. The second polypeptide expression vector of YN-052 is the light chain expression vector of YN-036.

After correct sequencing, the first polypeptide and the second polypeptide expression vectors of the anti-PD-L1/CD137 bispecific antibody YN-052 were co-transfected into 293F cell for transient expression. After culturing in serum-free medium for 7 days, the cell culture supernatant was collected and purified by Protein A column to obtain the antibody protein. The purified antibody was dialyzed with PBS, and finally quantified with BCA Protein Assay Kit (Pierce, 23225).

The amino acid sequence of the first polypeptide of YN-052 is shown in SEQ ID NO: 44, and the amino acid sequence of the second polypeptide of YN-052 is shown in SEQ ID NO: 34.

The binding affinity of the anti-PD-L1/CD137 bispecific antibodies YN-051 and YN-051 to the recombinant human PD-L1-His protein (Origincell Therapeutics Co., Ltd.) was measured by a molecular interaction analyzer (Octet RED384, purchased from Pall ForteBio Analytics Co., Ltd.). The antigen-antibody binding kinetics were analyzed by the biofilm interference (BLI) technology, using a molecular interaction analyzer (Octet RED384, purchased from Pall ForteBio Analytics Co., Ltd.) and using a PBS buffer containing 0.1% BSA and 0.02% Tween 20. The antibody with a concentration of 50 nM was fixed with the AHC sensor, and bound at 1500 rpm for 5 minutes; then it was bound with the double-diluted antigen solution (50, 25, 12.5, 6.25, 3.125, 1.56 nM) with 7 concentration gradients at 1500 rpm for 5 minutes; and finally dissociated at 1500 rpm for 10 minutes. The AHC sensor was regenerated by glycine pulses and then reused. The obtained results would be analyzed by Octet Data Analysis 9.0 software (Pall ForteBio Analytics Co., Ltd.) to give the $K_D$, $K_{on}$ (1/Ms) and $K_{off}$ (1/s). The measured results of the binding affinity of YN-007 to human PD-L1-Fc are shown in Table 10.

TABLE 10

Binding Affinity of Anti-PD-L1/CD137 Bispecific Antibody to Human PD-L1-His

| | Human PD-L1-His | | | | | | |
|---|---|---|---|---|---|---|---|
| Antibody | $K_D$ (M) | $K_D$ Error | $K_{on}$ (1/Ms) | $K_{on}$ Error | $K_{off}$ (1/s) | $K_{off}$ Error | Full R^2 |
| YN-051 | $5.17 \times 10^{-10}$ | $4.97 \times 10^{-12}$ | $5.32 \times 10^5$ | $2.54 \times 10^3$ | $2.75 \times 10^{-4}$ | $2.29 \times 10^{-6}$ | 0.9981 |
| YN-052 | $5.72 \times 10^{-10}$ | $5.69 \times 10^{-12}$ | $4.48 \times 10^5$ | $2.06 \times 10^3$ | $2.57 \times 10^{-4}$ | $2.26 \times 10^{-6}$ | 0.9984 |

The binding affinity of the anti-PD-L1/CD137 bispecific antibodies YN-051 and YN-052 to the recombinant human CD137-His protein (Origincell Therapeutics Co., Ltd.) was measured by a molecular interaction analyzer (Octet RED384, purchased from Pall ForteBio Analytics Co., Ltd.). The antigen-antibody binding kinetics were analyzed by the biofilm interference (BLI) technology, using a molecular interaction analyzer (Octet RED384, purchased from Pall ForteBio Analytics Co., Ltd.) and using a PBS buffer containing 0.1% BSA and 0.02% Tween 20. The antibody with a concentration of 50 nM was fixed with the AHC sensor, and bound at 1500 rpm for 5 minutes; then it was bound with the double-diluted recombinant human CD137-His protein antigen solution (100, 50, 25, 12.5, 6.25, 3.125, 1.56 nM) at 1500 rpm for 5 minutes; and finally dissociated at 1500 rpm for 10 minutes. The AHC sensor was regenerated by glycine pulses and then reused. The obtained results would be analyzed by Octet Data Analysis 9.0 software (Pall ForteBio Analytics Co., Ltd.) to give the $K_D$, $K_{on}$ (1/Ms) and $K_{off}$ (1/s).

The measured results of the binding affinity of anti-PD-L1/CD137 bispecific antibodies YN-051 and YN-052 to human CD137 are shown in Table 11.

TABLE 11

Binding Affinity of Anti-PD-L1/CD137 Bispecific Antibody to Human CD137-His

| | Human 4-1BB-His | | | | | | |
|---|---|---|---|---|---|---|---|
| Antibody | $K_D$ (M) | $K_D$ Error | kon (1/Ms) | kon Error | kdis (1/s) | kdis Error | Full R^2 |
| YN-051 | $1.64 \times 10^{-9}$ | $3.93 \times 10^{-11}$ | $8.99 \times 10^4$ | $7.25 \times 10^2$ | $1.47 \times 10^{-4}$ | $3.33 \times 10^{-6}$ | 0.9981 |
| YN-052 | $2.08 \times 10^{-9}$ | $4.36 \times 10^{-11}$ | $8.37 \times 10^4$ | $6.93 \times 10^2$ | $1.74 \times 10^{-4}$ | $3.35 \times 10^{-6}$ | 0.9982 |

Figure 15:
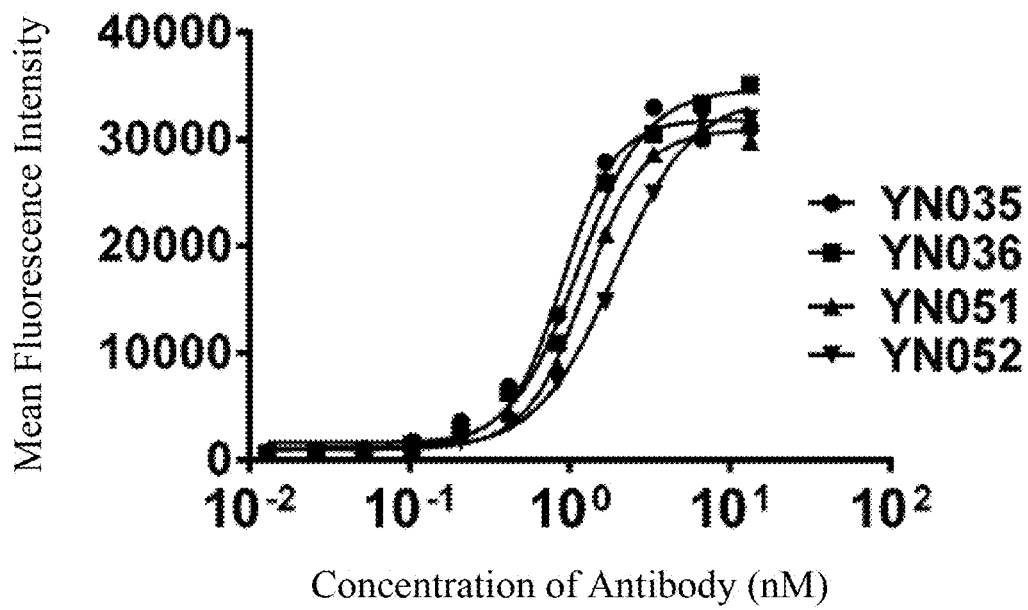
FIG. 15 shows the status that the PD-L1 antibody of the present application binds to MDA-MB-231 cells.

Human breast cell strain MDA-MB-231 (Shanghai Chinese Academy of Sciences Cell Library) highly expresses the human PD-L1 molecule. The binding of the PD-1 antibodies YN-035, YN-036 and the anti-PD-L1/CD137 bispecific antibodies YN-051 and YN-052 to MDA-MB-231 cells was detected by flow cytometry: to $1 \times 10^6$/ml of MDA-MB-231 cells was added individual double-diluted antibodies, respectively, mixed well and incubated at 4° C. for 1 hr. After cell washing, Goat F(ab')$_2$ Anti-Human IgG-Fc (DyLight 650) (ab98593, abcam) was added and incubated at 4° C. for 30 min. After cell washing, the fluorescence intensity was detected by a flow cytometer (Intellicyt iQue Screener). The experimental results are shown in FIG. 15: YN-035, YN-036, YN-051 and YN-052 all can effectively bind to MDA-MB-231 cells.

Figure 16:
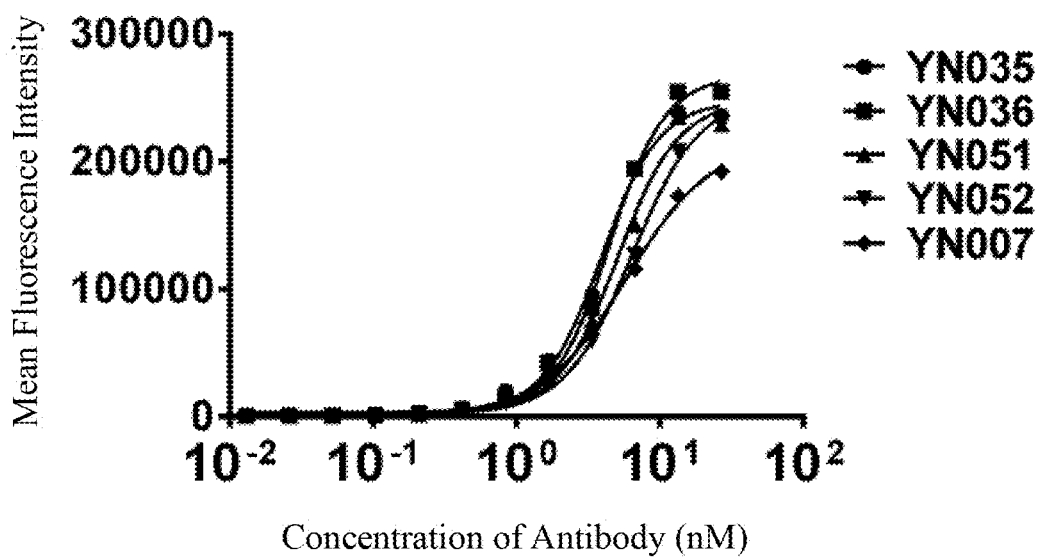
FIG. 16 shows the status that the PD-L1 antibody and the PD-L1/CD137 bispecific antibody of the present application bind to the CHO cells which stably express human PD-L1.

The binding activity of the PD-1 antibodies YN-035, YN-036 and the anti-PD-L1/CD137 bispecific antibodies YN-051 and YN-052 to human PD-L1 was detected by flow cytometry: to $1 \times 10^6$/ml of the CHO cells that stably expressed human PD-L1 was added individual double-diluted antibodies, respectively, mixed well and incubated at 4° C. for 1 hr. After cell washing, Goat F(ab')$_2$ Anti-Human IgG-Fc (DyLight 650) (ab98593, abcam) was added and incubated at 4° C. for 30 min. After cell washing, the fluorescence intensity was detected by a flow cytometer (Intellicyt iQue Screener). The experimental results are shown in FIG. 16: YN-035, YN-036, YN-051, YN-052, YN-007 all can effectively bind to CHO cells expressing human PD-L1.

Figure 17:
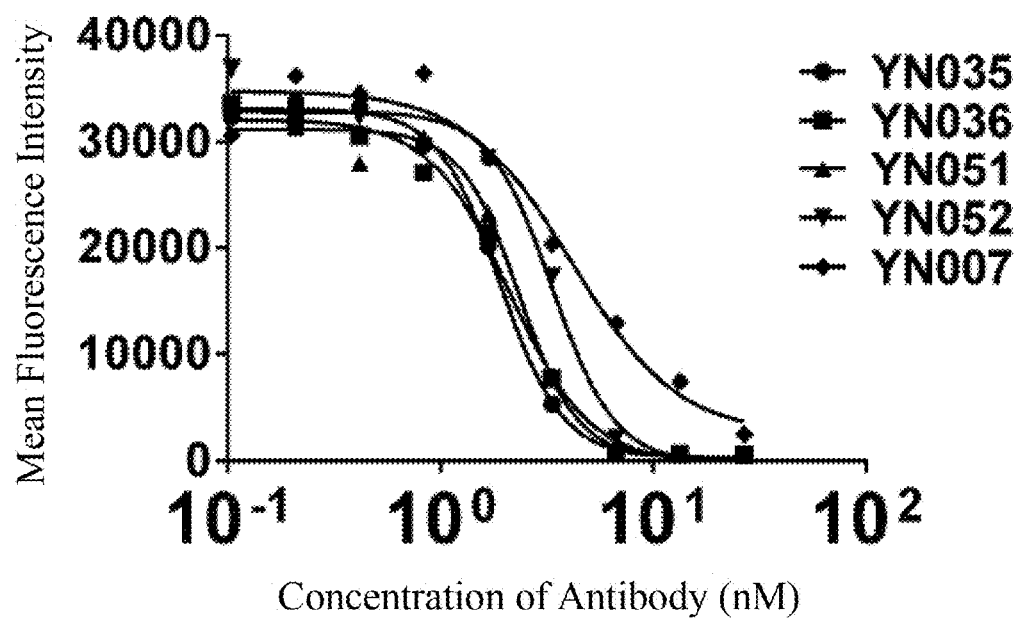
FIG. 17 shows the status that the PD-L1 antibody and PD-L1/CD137 bispecific antibody of the present application inhibit the binding of human PD-1 to human PD-L1.

The inhibitory capacity of the PD-1 antibodies YN-035, YN-036 and the anti-PD-L1/CD137 bispecific antibodies YN-051, YN-052, YN-007 to human PD-L1/human PD-1 was detected by flow cytometry: the human PD-1-Fc protein was labeled with biotin (EZ-Link Sulfo-NHS-LC-Biotin, Pierce, 21327). The human PD-1-Fc labeled with a subsaturated concentration of biotin was added into $1 \times 10^6$/ml of the CHO cells that stably expressed human PD-L1, and then individual double-diluted antibodies were immediately added, mixed well and incubated (4° C., 1 hr). After cell washing, Streptavidin R-PE Conjugate (life technology, SA10041) was added and incubated (4° C., 30 min). After cell washing, the fluorescence intensity was detected by a flow cytometer (Intellicyt iQue Screener). The experimental results are shown in FIG. 17: the PD-L1 antibodies YN-035, YN-036, YN-051, YN-052, YN-007 all can effectively inhibit the binding of human PD-1 to the CHO cells expressing human PD-L1.

Figure 18:
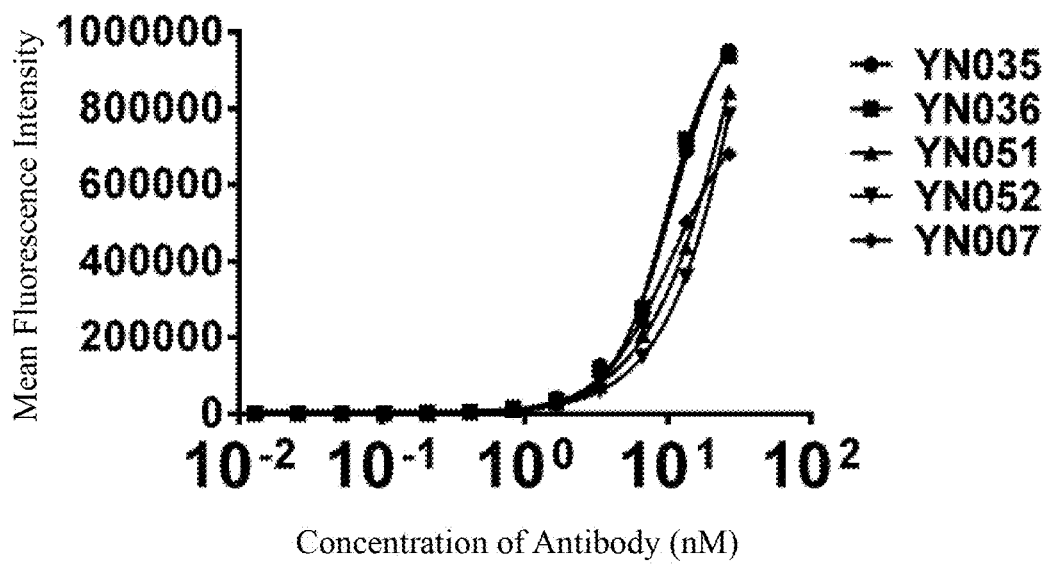
FIG. 18 shows the status that the PD-L1 antibody and PD-L1/CD137 bispecific antibody of the present application bind to the CHO cells which stably express mouse PD-L1.

The binding activity of the PD-1 antibodies YN-035, YN-036 and the anti-PD-L1/CD137 bispecific antibodies YN-007, YN-051 and YN-052 to mouse PD-L1 was detected by flow cytometry: to $1 \times 10^6$/ml of the CHO cells that stably expressed mouse PD-L1 was added individual double-diluted antibodies, respectively, mixed well and incubated at 4° C. for 1 hr. After cell washing, Goat F(ab')$_2$ Anti-Human IgG-Fc (DyLight 650) (ab98593, abcam) was added and incubated at 4° C. for 30 min. After cell washing, the fluorescence intensity was detected by a flow cytometer (Intellicyt iQue Screener). The experimental results are shown in FIG. 18: YN-035, YN-036, YN-051, YN-052, YN007 all can effectively bind to the CHO cells expressing mouse PD-L1.

The inhibitory capacity of the PD-1 antibodies YN-035, YN-036 and the anti-PD-L1/CD137 bispecific antibodies YN-007, YN-051 and YN-052 to mouse PD-L1/mouse PD-1 was detected by flow cytometry: the mouse PD-1-Fc labeled with biotin (EZ-Link Sulfo-NHS-LC-Biotin, Pierce, 21327).

Figure 19:
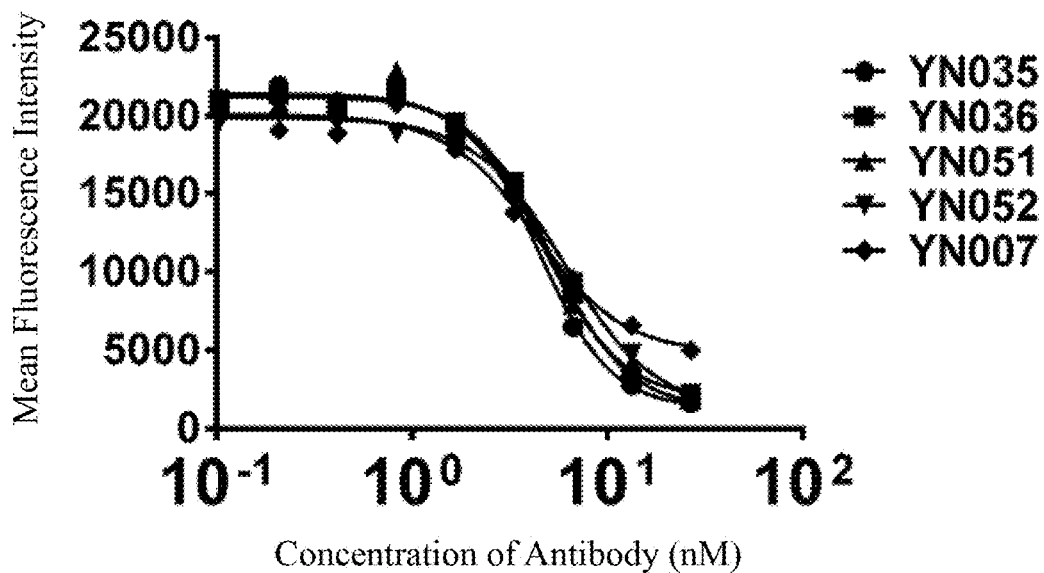
FIG. 19 shows the status that the PD-L1 antibody and PD-L1/CD137 bispecific antibody of the present application inhibit the binding of mouse PD-1 to mouse PD-L1.

The mouse PD-1-Fc labeled with a subsaturated concentration of biotin was added into $1\times10^6$/ml of CHO cells stably expressing mouse PD-L1, and then individual double-diluted antibodies were immediately added, mixed well and incubated (4° C., 1 hr). After cell washing, Streptavidin R-PE Conjugate (life technology, SA10041) was added and incubated (4° C., 30 min). After cell washing, the fluorescence intensity was detected by a flow cytometer (Intellicyt iQue Screener). The results are shown in FIG. 19: the PD-L1 antibodies YN-035, YN-036, YN-051, YN-052, YN-007 all can effectively inhibit the binding of mouse PD-1 to the CHO cells expressing mouse PD-L1.

Figure 20:
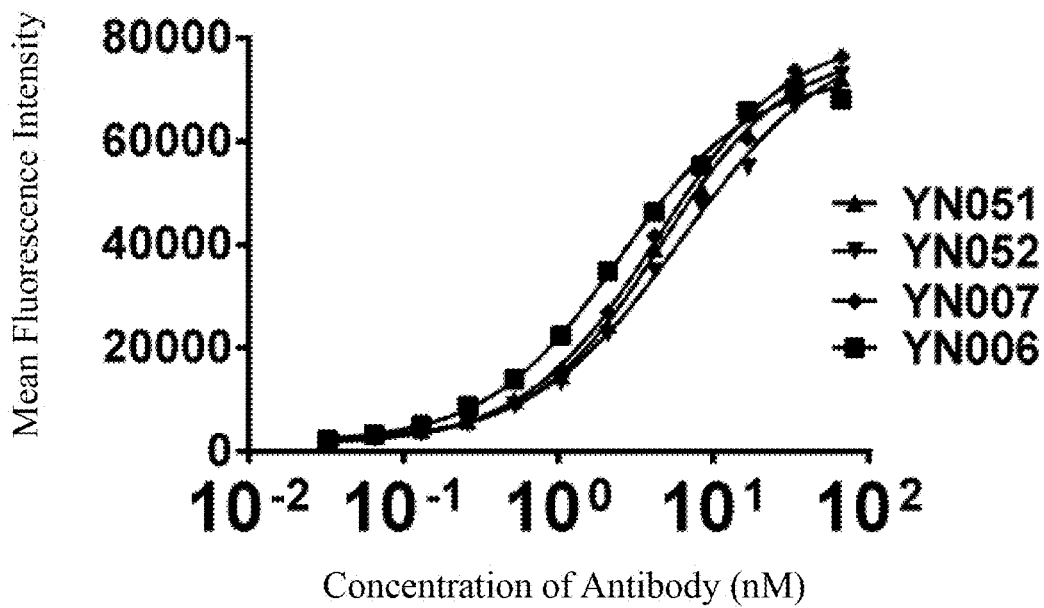
FIG. 20 shows the status that the CD137 antibody and PD-L1/CD137 bispecific antibody of the present application bind to the 293T cells which stably express human CD137.

The binding activity of the CD137 antibody YN-006 and the anti-PD-L1/CD137 bispecific antibodies YN-007, YN-051 and YN-052 to human CD137 was detected by flow cytometry: to $1\times10^6$/ml of 293T cells that stably express human CD137 was added individual double-diluted antibodies, respectively, mixed well and incubated at 4° C. for 1 hr. After cell washing, Goat F(ab')$_2$ Anti-Human IgG-Fc (DyLight 650) (ab98593, abcam) was added and incubated at 4° C. for 30 min. After cell washing, the fluorescence intensity was detected by a flow cytometer (Intellicyt iQue Screener). The experimental results are shown in FIG. 20: YN-006, YN-007, YN-051 and YN-052 all can effectively bind to the 293T cells expressing human CD137.

Example 18: SDS Polyacrylamide Gel Electrophoresis (SDS-PAGE) Analysis

Figure 21A:
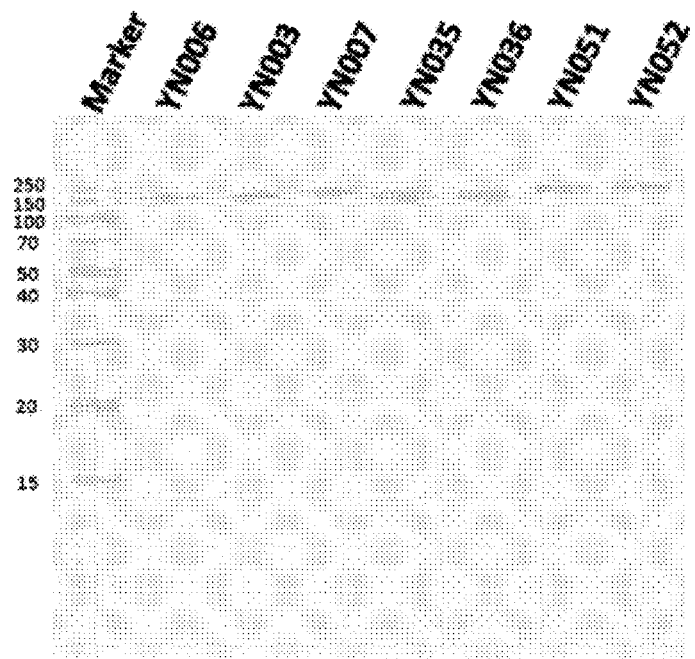
FIGS. 21a and 21b show the status that the molecular weight of the antibody of the present application is analyzed by SDS-PAGE analysis. a, non-reduced; and b, reduced.
Figure 21B:
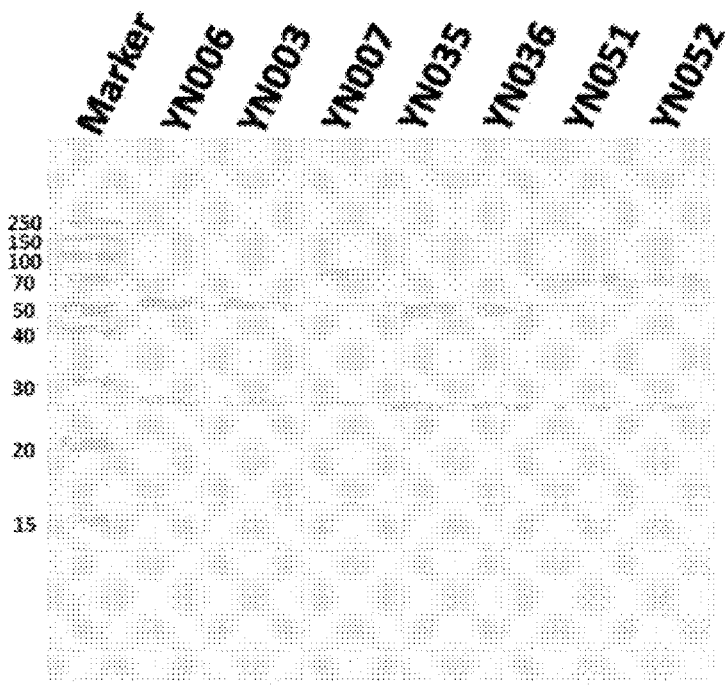

After being purified as above, the antibodies YN-003, YN-006, YN-007, YN-035, YN-036, YN-051, YN-052 were measured by SDS-PAGE under reducing and non-reducing conditions for their molecular weights. The results are shown in FIGS. 21a and 21b: under non-reducing conditions (as shown in FIG. 21a), the monoclonal antibodies YN-003, YN006, YN-035, and YN-036 are all presented as a band with a molecular weight of about 150 kDa, while the bispecific antibodies YN-007, YN-051, YN-052 are all presented as a band with a molecular weight of about 200 kDa. Under reducing conditions (as shown in FIG. 21b), the monoclonal antibodies YN-003, YN006, YN-035, and YN-036 are all presented as two bands with a molecular weight of about 55 kDa and 25 kDa, while the bispecific antibodies YN-007, YN-051, YN-052 are all presented as two bands with a molecular weight of about 75 kDa and 25 kDa.

Example 19: Agonistic Activity of Anti-PD-L1/CD137 Bispecific Antibody (Luciferase Activity Assay)

Figure 22:
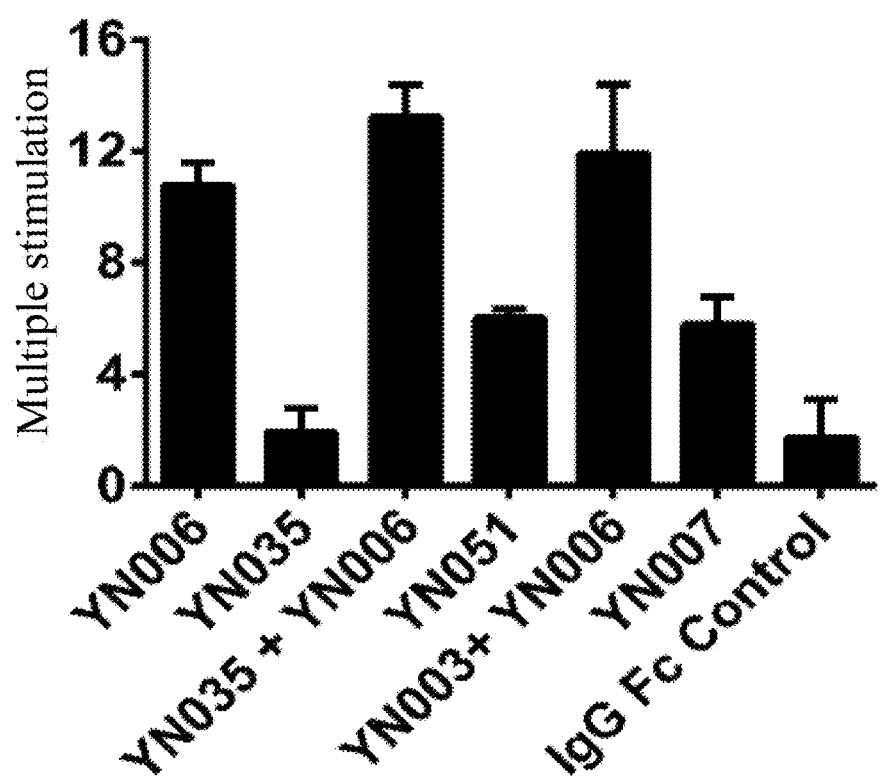
FIG. 22 shows the results of various antibodies of the present application stimulating the luciferase activity of the 293T cells which express the human CD137 and stably integrate luciferase reporter gene.

293T cells expressing human CD137 and stably integrated NFκB luciferase reporter gene were prepared. The cells were harvested, washed and resuspended in complete medium without phenol red (DMEM medium containing 10% fetal bovine serum, HEPES buffer, non-essential amino acids and L-glutamine) at a density of $6\times10^5$ cells/mL. 96-well plates (purchased from PerkinElmer) were plated, and 50 µl of cell suspension was added to each well. A cross-linked antibody (goat anti-human IgG Fc) was added at a ratio of 2.5:1, then YN-006 (10 µg/ml), YN-035 (10 µg/ml), YN-035+YN-006 (10 µg/ml+10 µg/ml), YN-051 (10 µg/ml), YN-003+YN006 (10 µg/ml+10 µg/ml), YN-007 (10 µg/ml), and control antibody IgG Fc (10 µg/ml) were added, respectively, and incubated at 37° C. for 5 hours. Subsequently, 75 µL of Bright-Glo Luciferase reagent (purchased from Promega) was added, and the luciferase activity was measured with a microplate reader (purchased from Tecan). The ratio of the cell fluorescence values of each antibody-treated cell group to the non-antibody-treated group was compared (see FIG. 22). The results show that as compared with the control IgG Fc, YN-006, YN035+YN-006, YN003+YN006, YN-007, YN-051 all have an obvious agonistic activity, while the anti-PD-L1 antibody YN-035 does not (see FIG. 22).

Figure 23:
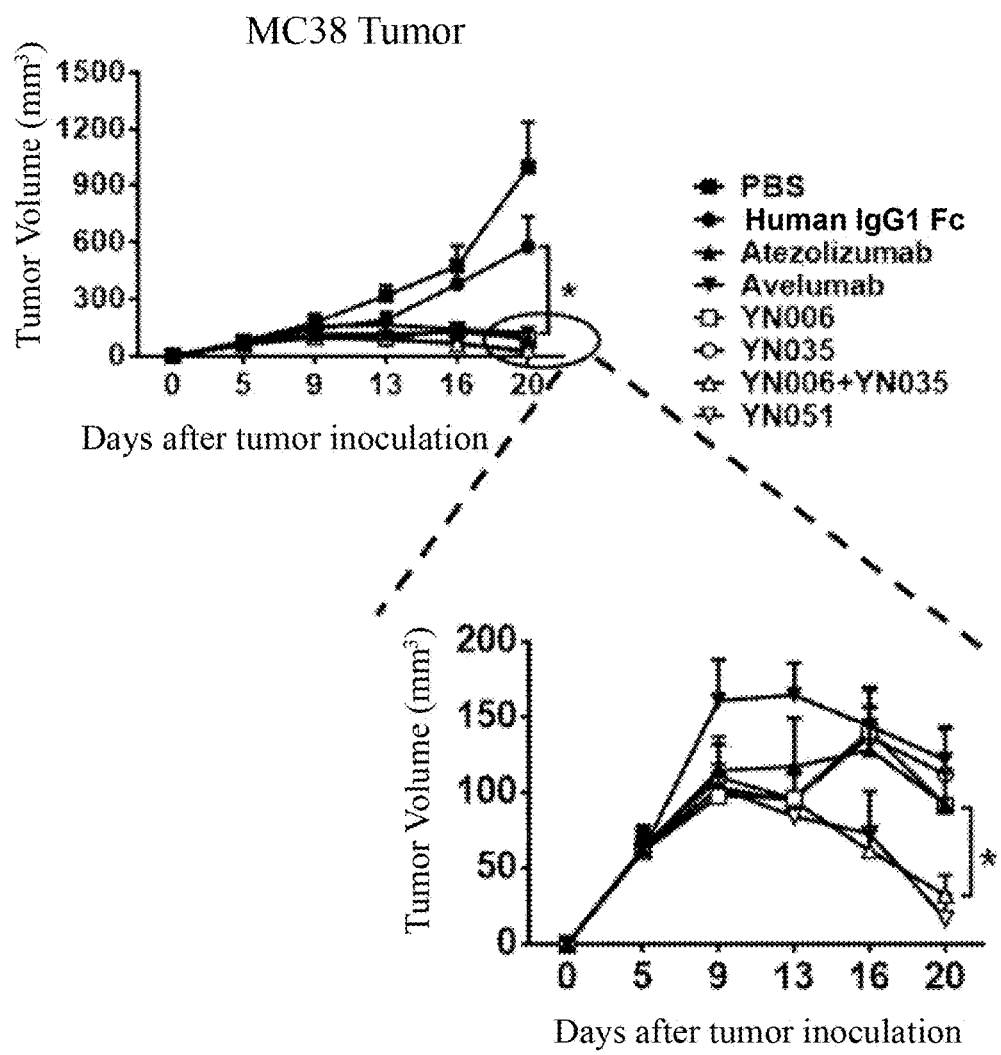
FIG. 23 shows the effect of the antibodies of the present application on the growth of MC38 tumors in C57BL/6 female mice with human CD137 gene (*, P<0.05; Unpaired t test).

Example 20: Studies of Antitumor Effect of Anti-PD-L1/CD137 Bispecific Antibody in Colon Cancer-Bearing Mice On Day 0, 6-8 week old C57BL/6 female mice with human 4-1BB (B-hTNFRSF9 (4-1BB) mice, purchased from Beijing Biocytogen Co., Ltd.) were subcutaneously inoculated with $3\times10^6$ MC38 mouse colorectal cancer cells (Shanghai Linyuan Biotechnology Co., Ltd.). On Day 6, the mice were evenly divided into 8 groups. The tumor-bearing mice in each group were intraperitoneally injected with PBS (twice per week, two weeks in total), control antibody human IgG-Fc protein (7.5 mg/kg, twice per week, two weeks in total), CD137 antibody YN-006 antibody (3 mg/kg, twice per week, two weeks in total), PD-L1 antibody YN-035 (7.5 mg/kg, twice per week, two weeks in total), CD137 antibody YN-006 antibody (3 mg/kg, twice per week, two weeks in total)+PD-L1 antibody YN-035 (7.5 mg/kg, twice per week, two weeks in total), anti-PD-L1/CD137 bispecific antibody YN-051 (7.5 mg/kg, twice per week, two weeks in total), anti-PD-L1 antibody Atezolizumab (7.5 mg/kg, twice per week, two weeks in total), and anti-PD-L1 antibody Avelumab (7.5 mg/kg, twice per week, two weeks in total), respectively. Except that the PBS group included 5 mice, each of the remainder 7 groups included 6 mice. The mice in each group were regularly observed for the change of body weight and tumor size. The experimental results are shown in FIG. 23 and Table 12. FIG. 23 shows that YN006, YN035, YN006+YN035, YN051, Atezolizumab, and Avelumab all have a significant antitumor activity as compared with the PBS group or the control antibody human IgG-Fc group. Among them, the anti-tumor activities of YN006+YN035 and YN051 are significantly stronger than YN006, YN035, Atezolizumab, and Avelumab. Table 12 shows that at the end of the animal experiment, 5 mice in the YN051 group had tumors completely regressed, while only 1 mouse in the YN006+YN035 group had tumors completely regressed, indicating that the therapeutic effect of YN051 was better than that of YN006+YN035.

TABLE 12

Number of Mice in Which the Tumors are Completely Eliminated of Each Group

| Antibody | Number of mice in which the tumors are completed eliminated/total number of experiment animals in each group |
|---|---|
| PBS | 0/5 |
| Human IgG1 Fc | 0/6 |
| Atezolizumab | 0/6 |
| Avelumab | 0/6 |
| YN-006 | 0/6 |
| YN-035 | 1/6 |
| YN-006 + YN-035 | 1/6 |
| YN-051 | 5/6 |

What is claimed is:

1. A bispecific antibody, comprising:
a first targeting moiety that specifically binds to a PD-L1 protein, and
a second targeting moiety that specifically binds to a CD137 protein,
wherein said first targeting moiety comprises an antibody or an antigen binding fragment thereof, and
said second targeting moiety comprises an antibody or an antigen binding fragment thereof,
said antibody of the first targeting moiety comprises an antibody heavy chain or a fragment thereof comprising HCDR1-3, and said HCDR1-3 comprise the amino acid sequences as set forth in SEQ ID NO: 47, 48 and 51, respectively,
said antibody of the first targeting moiety comprises an antibody light chain or a fragment thereof comprising LCDR1-3, and said LCDR1-3 comprise the amino acid sequences as set forth in SEQ ID NO: 55, 60 and 64, respectively,
said antibody of the second targeting moiety comprises an antibody heavy chain or a fragment thereof comprising HCDR1-3, and said HCDR1-3 comprise the amino acid sequences as set forth in SEQ ID NO: 77-79, respectively, and
said antibody of the second targeting moiety comprises an antibody light chain or a fragment thereof comprising LCDR1-3, and said LCDR1-3 comprise the amino acid sequences as set forth in SEQ ID NO: 80-82, respectively.

2. The bispecific antibody according to claim 1,
wherein said antibody of the first targeting moiety comprises a heavy chain variable region VH and a light chain variable region VL,
said VH comprises the amino acid sequence as set forth in SEQ ID NO: 31, and
said VL comprises the amino acid sequence as set forth in SEQ ID NO: 33.

3. The bispecific antibody according to claim 1,
wherein said antibody of the second targeting moiety comprises a heavy chain variable region VH and a light chain variable region VL,
said VH comprises the amino acid sequence as set forth in SEQ ID NO: 25, and
said VL comprises the amino acid sequence as set forth in SEQ ID NO: 20.

4. The bispecific antibody according to claim 1,
wherein said antibody heavy chain or the fragment thereof of the antibody of the first targeting moiety comprises the amino acid sequence as set forth in SEQ ID NO: 32, and
said antibody light chain or the fragment thereof of the antibody of the first targeting moiety comprises the amino acid sequence as set forth in SEQ ID NO: 34.

5. The bispecific antibody according to claim 3,
wherein said antibody heavy chain or the fragment thereof of the antibody of the second targeting moiety comprises the amino acid sequence as set forth in SEQ ID NO: 27, and
said antibody light chain or the fragment thereof of the antibody of the second targeting moiety comprises the amino acid sequence as set forth in SEQ ID NO: 23.

6. The bispecific antibody according to claim 1, comprising:
a first polypeptide chain, and
a second polypeptide chain,
wherein said first polypeptide chain comprises a heavy chain variable region of the antibody of the first targeting moiety, a heavy chain variable region of the antibody of the second targeting moiety, and a light chain variable region of the antibody of the second targeting moiety; and
said second polypeptide chain comprises a light chain variable region of the antibody of the first targeting moiety.

7. The bispecific antibody according to claim 1,
wherein in said first polypeptide chain,
said heavy chain variable region of the antibody of the first targeting moiety is located at an N-terminus of said heavy chain variable region of the antibody of the second targeting moiety, and said heavy chain variable region of the antibody of the second targeting moiety is located at an N-terminus of said light chain variable region of the antibody of the second targeting moiety; or,
said heavy chain variable region of the antibody of the first targeting moiety is located at the N-terminus of said light chain variable region of the antibody of the second targeting moiety, and said light chain variable region of the antibody of the second targeting moiety is located at the N-terminus of said heavy chain variable region of the antibody of the second targeting moiety.

8. The bispecific antibody according to claim 1, wherein said antibody of the second targeting moiety comprises a scFv.

9. The bispecific antibody according to claim 8, said scFv comprises the amino acid sequence as set forth in SEQ ID NO: 83.

10. The bispecific antibody according to claim 1, further comprising:
a first polypeptide chain, and
a second polypeptide chain,
wherein said first polypeptide chain comprises the amino acid sequence as set forth in SEQ ID NO: 43.

11. The bispecific antibody according to claim 10, wherein said second polypeptide chain comprises the amino acid sequence as set forth in SEQ ID NO: 34.

12. A pharmaceutical composition, comprising:
said bispecific antibody according to claim 1 and a pharmaceutically acceptable adjuvant.

13. A method for treating a tumor, the method comprising: administrating said bispecific antibody according to claim 1 to a subject in need of.

\* \* \* \* \*

SEQUENCE LISTING

<160> NUMBER OF SEQ ID NOS: 92

<210> SEQ ID NO 1
<211> LENGTH: 363
<212> TYPE: DNA
<213> ORGANISM: Artificial Sequence
<220> FEATURE:
<223> OTHER INFORMATION: Nucleotide sequence encoding PD-L1 antibody YN-002 VH

<400> SEQUENCE: 1

```
caggtgcagc tggtgcagtc tggggctgag gtgaggaagc ctgggtcctc ggtgaaggtc      60
tcctgcaagg cttctggagg caccttcagc agctatgcta tcagctgggt gcgacaggcc     120
cctggacaag gcttgagtg gatgggaagg atcatccct tccttggtat agcaaactac       180
gcacagaagt tccagggcag agtcacgatt accgcggaca atccacgag cacagcctac      240 atggagctga gcagcctgag atctgaggac acggccgtgt attactgtgc gagaacgatg    300
gacggataca gctatggcaa ctttgactac tggggccagg gaaccctggt cactgtctcc    360
tca                                                                   363
```

<210> SEQ ID NO 2
<211> LENGTH: 121
<212> TYPE: PRT
<213> ORGANISM: Artificial Sequence
<220> FEATURE:
<223> OTHER INFORMATION: VH of PD-L1 antibody YN-002

<400> SEQUENCE: 2

```
Gln Val Gln Leu Val Gln Ser Gly Ala Glu Val Arg Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Met Asp Gly Tyr Ser Tyr Gly Asn Phe Asp Tyr Trp Gly
            100                 105                 110

Gln Gly Thr Leu Val Thr Val Ser Ser
        115                 120
```

<210> SEQ ID NO 3
<211> LENGTH: 336
<212> TYPE: DNA
<213> ORGANISM: Artificial Sequence
<220> FEATURE:
<223> OTHER INFORMATION: Nucleotide sequence encoding PD-L1 antibody YN-002 VL

<400> SEQUENCE: 3

```
cagtctgccc tgactcagcc tgcctccgtg tctgggtctc ctggacagtc gatcaccatc      60
```

```
tcctgcaccg gaaccagcag tgacgttggt ggttataact atgtctcctg gtaccaacag    120
cacccaggca agccccccaa actcctcatc tatggtaaca gcaatcggcc ctcagggtc     180 cctgaccgat tctctggctc caagtctggc acctcagcct ccctggccat cactgggctc    240
caggctgagg atgaggctga ttattactgc cagtcctatg acagcagcct gagtggttcg    300
gtattcggcg gagggaccaa gctgaccgtc ctaggc                              336
```

<210> SEQ ID NO 4
<211> LENGTH: 112
<212> TYPE: PRT
<213> ORGANISM: Artificial Sequence
<220> FEATURE:
<223> OTHER INFORMATION: VL of PD-L1 antibody YN-002

<400> SEQUENCE: 4

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Gly Gly Thr Lys Leu Thr Val Leu Gly
            100                 105                 110
```

<210> SEQ ID NO 5
<211> LENGTH: 1353
<212> TYPE: DNA
<213> ORGANISM: Artificial Sequence
<220> FEATURE:
<223> OTHER INFORMATION: Nucleotide sequence encoding the heavy chain of
      PD-L1 antibody YN-002

<400> SEQUENCE: 5

```
caggtgcagc tggtgcagtc tggggctgag gtgaggaagc ctgggtcctc ggtgaaggtc    60
tcctgcaagg cttctggagg caccttcagc agctatgcta tcagctgggt gcgacaggcc    120
cctggacaag gcttgagtg gatgggaagg atcatcccta tccttggtat agcaaactac     180
gcacagaagt tccagggcag agtcacgatt accgcggaca atccacgag cacagcctac     240 atggagctga gcagcctgag atctgaggac acggccgtgt attactgtgc gagaacgatg    300
gacggataca gctatggcaa ctttgactac tggggccagg gaaccctggt cactgtctcc    360
tcagcgtcga ccaagggccc atcggtcttc cccctggcac cctcctccaa gagcacctct    420
gggggcacag cggccctggg ctgcctggtc aaggactact cccccgaacc ggtgacggtg    480
tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gaaagttgag    660
cccaaatctt gtgacaaaac tcacacatgc ccaccgtgcc cagcacctga actcctgggg    720
ggaccgtcag tcttcctctt ccccccaaaa cccaaggaca cctcatgat ctcccggacc     780 cctgaggtca catgcgtggt ggtggacgtg agccacgaag accctgaggt caagttcaac    840
```

```
tggtacgtgg acggcgtgga ggtgcataat gccaagacaa agccgcggga ggagcagtac      900
aacagcacgt accgtgtggt cagcgtcctc accgtcctgc accaggactg gctgaatggc      960
aaggagtaca agtgcaaggt ctccaacaaa gccctcccag cccccatcga gaaaaccatc     1020
tccaaagcca aagggcagcc ccgagaacca caggtgtaca ccctgccccc atcccgggat     1080
gagctgacca agaaccaggt cagcctgacc tgcctggtca aaggcttcta tcccagcgac     1140
atcgccgtgg agtgggagag caatgggcag ccggagaaca actacaagac cacgcctccc     1200
gtgctggact ccgacggctc cttcttcctc tacagcaagc tcaccgtgga caagagcagg     1260
tggcagcagg ggaacgtctt ctcatgctcc gtgatgcatg aggctctgca caaccactac     1320
acgcagaaga gcctctccct gtctccgggt aaa                                  1353
```

<210> SEQ ID NO 6
<211> LENGTH: 451
<212> TYPE: PRT
<213> ORGANISM: Artificial Sequence
<220> FEATURE:
<223> OTHER INFORMATION: Heavy chain of PD-L1 antibody YN-002

<400> SEQUENCE: 6

```
Gln Val Gln Leu Val Gln Ser Gly Ala Glu Val Arg Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Met Asp Gly Tyr Ser Tyr Gly Asn Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270
```

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 7
<211> LENGTH: 651
<212> TYPE: DNA
<213> ORGANISM: Artificial Sequence
<220> FEATURE:
<223> OTHER INFORMATION: Nucleotide sequence encoding the light chain of
      PD-L1 antibody YN-002

<400> SEQUENCE: 7
cagtctgccc tgactcagcc tgcctccgtg tctgggtctc ctggacagtc gatcaccatc      60
tcctgcaccg gaaccagcag tgacgttggt ggttataact atgtctcctg gtaccaacag     120
cacccaggca agcccccaa actcctcatc tatggtaaca gcaatcggcc ctcaggggtc     180
cctgaccgat tctctggctc caagtctggc acctcagcct ccctggccat cactgggctc     240
caggctgagg atgaggctga ttattactgc cagtcctatg acagcagcct gagtggttcg     300
gtattcggcg gagggaccaa gctgaccgtc ctaggccagc ccaaggctgc cccctcggtc     360
actctgttcc cacccctcctc tgaggagctt caagccaaca ggccacact ggtgtgtctc     420 ataagtgact tctacccggg agccgtgaca gtggcctgga aggcagatag cagccccgtc     480
aaggcgggag tggagaccac cacaccctcc aaacaaagca acaacaagta cgcggccagc     540
agctacctga gcctgacgcc tgagcagtgg aagtcccaca aagctacag ctgccaggtc     600 acgcatgaag ggagcaccgt ggagaagaca gtggccccta cagaatgttc a               651

<210> SEQ ID NO 8
<211> LENGTH: 217
<212> TYPE: PRT
<213> ORGANISM: Artificial Sequence
<220> FEATURE:
<223> OTHER INFORMATION: Light chain of PD-L1 antibody YN-002

<400> SEQUENCE: 8

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Leu Ile Tyr Gly Asn Ser Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
210                 215

<210> SEQ ID NO 9
<211> LENGTH: 121
<212> TYPE: PRT
<213> ORGANISM: Artificial Sequence
<220> FEATURE:
<223> OTHER INFORMATION: VH of PD-L1 antibody YN-003

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Met Asp Gly Tyr Ser Tyr Gly Asn Phe Asp Tyr Trp Gly
            100                 105                 110

Gln Gly Thr Leu Val Thr Val Ser Ser
        115                 120

<210> SEQ ID NO 10
```

```
<211> LENGTH: 363
<212> TYPE: DNA
<213> ORGANISM: Artificial Sequence
<220> FEATURE:
<223> OTHER INFORMATION: Nucleotide sequence encoding PD-L1 antibody
      YN-003 VH

<400> SEQUENCE: 10
caggtgcagc tggtgcagtc tggggctgag gtgaagaagc ctgggtcctc ggtgaaggtc    60
tcctgcaagg cttctggagg caccttcagc agctatgcta tcagctgggt gcgacaggcc   120
cctggacaag gcttgagtg gatgggaagg atcatcccta tccttggtat agcaaactac   180
gcacagaagt tccagggcag agtcacgatt accgcggaca atccacgag cacagcctac   240 atggagctga gcagcctgag atctgaggac acggccgtgt attactgtgc gagaacgatg   300
gacggataca gctatggcaa ctttgactac tggggccagg gaaccctggt cactgtctcc   360
tca                                                                 363

<210> SEQ ID NO 11
<211> LENGTH: 112
<212> TYPE: PRT
<213> ORGANISM: Artificial Sequence
<220> FEATURE:
<223> OTHER INFORMATION: VL of PD-L1 antibody YN-003

<400> SEQUENCE: 11

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Gly Asn Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Gly Gly Thr Lys Leu Thr Val Leu Gly
            100                 105                 110

<210> SEQ ID NO 12
<211> LENGTH: 336
<212> TYPE: DNA
<213> ORGANISM: Artificial Sequence
<220> FEATURE:
<223> OTHER INFORMATION: Nucleotide sequence encoding PD-L1 antibody
      YN-003 VL

<400> SEQUENCE: 12
cagtctgccc tgactcagcc tgcctccgtg tctgggtctc ctggacagtc gatcaccatc    60
tcctgcaccg gaaccagcag tgacgttggt ggttataact atgtctcctg gtaccaacag   120
cacccaggca agccccccaa actcatgatc tatggtaaca gcaatcggcc ctcagggtc   180 tctaatcgat tctctggctc caagtctggc aacacggcct ccctgaccat ctctgggctc   240
caggctgagg atgaggctga ttattactgc cagtcctatg acagcagcct gagtggttcg   300
gtattcggcg gagggaccaa gctgaccgtc ctaggc                             336

<210> SEQ ID NO 13
```

<211> LENGTH: 451
<212> TYPE: PRT
<213> ORGANISM: Artificial Sequence
<220> FEATURE:
<223> OTHER INFORMATION: Heavy chain of PD-L1 antibody YN-003

<400> SEQUENCE: 13

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Met Asp Gly Tyr Ser Tyr Gly Asn Phe Asp Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380
```

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly Lys
    450

<210> SEQ ID NO 14
<211> LENGTH: 1353
<212> TYPE: DNA
<213> ORGANISM: Artificial Sequence
<220> FEATURE:
<223> OTHER INFORMATION: Nucleotide sequence encoding the heavy chain of
      PD-L1 antibody YN-003

<400> SEQUENCE: 14
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaagg atcatcccta tccttggtat agcaaactac     180
gcacagaagt tccagggcag agtcacgatt accgcggaca atccacgag cacagcctac     240 atggagctga gcagcctgag atctgaggac acggccgtgt attactgtgc gagaacgatg     300
gacggataca gctatggcaa ctttgactac tggggccagg gaaccctggt cactgtctcc     360
tcagcgtcga ccaagggccc atcggtcttc cccctggcac cctcctccaa gagcacctct     420
gggggcacag cggccctggg ctgcctggtc aaggactact tccccgaacc ggtgacggtg     480
tcgtggaact caggcgccct gaccagcggc gtgcacacct tcccggctgt cctacagtcc     540
tcaggactct actccctcag cagcgtggtg accgtgccct ccagcagctt gggcacccag     600
acctacatct gcaacgtgaa tcacaagccc agcaacacca aggtggacaa gaaagttgag     660
cccaaatctt gtgacaaaac tcacacatgc ccaccgtgcc cagcacctga actcctgggg     720
ggaccgtcag tcttcctctt ccccccaaaa cccaaggaca cctcatgat ctcccggacc     780 cctgaggtca catgcgtggt ggtggacgtg agccacgaag accctgaggt caagttcaac     840
tggtacgtgg acggcgtgga ggtgcataat gccaagacaa agccgcggga ggagcagtac     900
aacagcacgt accgtgtggt cagcgtcctc accgtcctgc accaggactg gctgaatggc     960
aaggagtaca agtgcaaggt ctccaacaaa gccctcccag ccccatcga gaaaaccatc    1020 tccaaagcca aagggcagcc ccgagaacca caggtgtaca ccctgccccc atcccgggat    1080
gagctgacca agaaccaggt cagcctgacc tgcctggtca aaggcttcta tcccagcgac    1140
atcgccgtgg agtgggagag caatgggcag ccggagaaca actacaagac cacgcctccc    1200
gtgctggact ccgacggctc cttcttcctc tacagcaagc tcaccgtgga caagagcagg    1260
tggcagcagg ggaacgtctt ctcatgctcc gtgatgcatg aggctctgca caaccactac    1320
acgcagaaga gcctctccct gtctccgggt aaa                                 1353

<210> SEQ ID NO 15
<211> LENGTH: 217
<212> TYPE: PRT
<213> ORGANISM: Artificial Sequence
<220> FEATURE:

<223> OTHER INFORMATION: Light chain of PD-L1 antibody YN-003; The
second polypeptide of PD-L1/4-1BB bispecific antibody YN-007

<400> SEQUENCE: 15

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Gly Asn Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 16
<211> LENGTH: 651
<212> TYPE: DNA
<213> ORGANISM: Artificial Sequence
<220> FEATURE:
<223> OTHER INFORMATION: Nucleotide sequence encoding the light chain of
PD-L1 antibody YN-003; Nucleotide sequence encoding the second
polypeptide of YN-007

<400> SEQUENCE: 16
cagtctgccc tgactcagcc tgcctccgtg tctgggtctc ctggacagtc gatcaccatc      60
tcctgcaccg gaaccagcag tgacgttggt ggttataact atgtctcctg gtaccaacag     120
cacccaggca agcccccaa actcatgatc tatggtaaca gcaatcggcc ctcaggggtc      180
tctaatcgat tctctggctc caagtctggc aacacggcct ccctgaccat ctctgggctc     240
caggctgagg atgaggctga ttattactgc cagtcctatg acagcagcct gagtggttcg     300
gtattcggcg gagggaccaa gctgaccgtc ctaggccagc ccaaggctgc ccctcggtc      360 actctgttcc caccctcctc tgaggagctt caagccaaca ggccacact ggtgtgtctc      420 ataagtgact tctacccggg agccgtgaca gtggcctgga aggcagatag cagccccgtc     480
aaggcgggag tggagaccac cacaccctcc aaacaaagca acaacaagta cgcggccagc     540
agctacctga gcctgacgcc tgagcagtgg aagtcccaca gaagctacag ctgccaggtc     600
acgcatgaag ggagcaccgt ggagaagaca gtggcccta cagaatgttc a        651

<210> SEQ ID NO 17
<211> LENGTH: 360
<212> TYPE: DNA
<213> ORGANISM: Artificial Sequence
<220> FEATURE:
<223> OTHER INFORMATION: Nucleotide sequence encoding 4-1BB antibody
      YN-005 VH

<400> SEQUENCE: 17
caggtccagc tggtgcagtc tggggggaggc ttggtacagc ctgggggtc cctgagactc     60 tcctgtgcag cctctggatt caccttagc agctatgcca tgagctgggt ccgccaggct    120
ccagggaagg gctggagtg gtctcagct attagtggta gtggtggtag cacatactac    180
gcagactccg tgaagggccg gttcaccatc tccagagaca attccaagaa cacgctgtat    240
cttcaaatga acagcctgag agccgaggac acggccgtgt attactgtgc gaaaactaac    300
tggggcccct ctgatgcttt tgatatctgg ggccaaggga caatggtcac cgtctcctca    360

<210> SEQ ID NO 18
<211> LENGTH: 120
<212> TYPE: PRT
<213> ORGANISM: Artificial Sequence
<220> FEATURE:
<223> OTHER INFORMATION: VH of 4-1BB antibody YN-005

<400> SEQUENCE: 18

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Asn Trp Gly Pro Ser Asp Ala Phe Asp Ile Trp Gly Gln
            100                 105                 110

Gly Thr Met Val Thr Val Ser Ser
        115                 120

<210> SEQ ID NO 19
<211> LENGTH: 333
<212> TYPE: DNA
<213> ORGANISM: Artificial Sequence
<220> FEATURE:
<223> OTHER INFORMATION: Nucleotide sequence encoding 4-1BB antibody
      YN-005 VL; Nucleotide sequence encoding YN-006 VL

<400> SEQUENCE: 19
cagagcgtct tgactcagcc accctcagcg tctgggaccc ccgggcagag ggtcaccatc     60
tcttgttctg gaagcacctc cgacatcgga agttacagcg taaactggta ccagcagctc    120
ccaggaacgg ccccccaaact cctcatctat agtaataatc agcggccctc aggggtccct    180
gaccgattct ctggctccaa gtctggcacc tcagcctccc tggccatcag tgggctccag    240
tctgaggatg aggctgatta ttactgtgca gcatgggatg acagcctgaa tggttatgtc    300
ttcggaactg ggaccaagct gaccgtccta ggt        333

<210> SEQ ID NO 20
<211> LENGTH: 111
<212> TYPE: PRT
<213> ORGANISM: Artificial Sequence
<220> FEATURE:
<223> OTHER INFORMATION: VL of human 4-1BB antibody YN-006; VL of YN-005

<400> SEQUENCE: 20

Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Asp Ile Gly Ser Tyr
            20                  25                  30

Ser Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Leu Thr Val Leu Gly
            100                 105                 110

<210> SEQ ID NO 21
<211> LENGTH: 446
<212> TYPE: PRT
<213> ORGANISM: Artificial Sequence
<220> FEATURE:
<223> OTHER INFORMATION: Heavy chain of 4-1BB antibody YN-005

<400> SEQUENCE: 21

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Asn Trp Gly Pro Ser Asp Ala Phe Asp Ile Trp Gly Gln
            100                 105                 110

Gly Thr Met Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

```
Ser Ser Asn Phe Gly Thr Gln Thr Tyr Thr Cys Asn Val Asp His Lys
    195                 200                 205

Pro Ser Asn Thr Lys Val Asp Lys Thr Val Glu Arg Lys Cys Cys Val
210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 22
<211> LENGTH: 1338
<212> TYPE: DNA
<213> ORGANISM: Artificial Sequence
<220> FEATURE:
<223> OTHER INFORMATION: Nucleotide sequence encoding the heavy chain of
      4-1BB antibody YN-005

<400> SEQUENCE: 22
caggtccagc tggtgcagtc tggggggaggc ttggtacagc ctgggggtc cctgagactc      60 tcctgtgcag cctctggatt cacctttagc agctatgcca tgagctgggt ccgccaggct     120
ccagggaagg gctggagtg gtctcagct attagtggta gtggtggtag cacatactac       180
gcagactccg tgaagggccg gttcaccatc tccagagaca attccaagaa cacgctgtat     240
cttcaaatga acagcctgag agccgaggac acggccgtgt attactgtgc gaaaactaac     300
tggggcccct ctgatgcttt tgatatctgg ggccaaggga caatggtcac cgtctcctca     360
gcgtcgacca agggcccatc ggtcttcccc ctggcgccct gctccaggag cacctccgag     420
agcacagcgg ccctgggctg cctggtcaag gactacttcc ccgaaccagt gacggtgtcg     480
tggaactcag gcgctctgac cagcggcgtg cacaccttcc cggctgtcct acagtcctca     540
ggactctact ccctcagcag cgtagtgacc gtgccctcca gcaacttcgg cacccagacc     600
```

```
tacacctgca acgtagatca caagcccagc aacaccaagg tggacaagac agttgagcgc    660
aaatgttgtg tcgagtgccc accgtgccca gcaccacctg tggcaggacc gtcagtcttc    720 ctcttcccc caaaacccaa ggacaccctc atgatctccc ggacccctga ggtcacgtgc    780
gtggtggtgg acgtgagcca cgaagacccc gaggtccagt tcaactggta cgtggacggc    840
gtggaggtgc ataatgccaa gacaaagcca cgggaggagc agttcaacag cacgttccgt    900
gtggtcagcg tcctcaccgt cgtgcaccag gactggctga acggcaagga gtacaagtgc    960
aaggtctcca caaaggcct cccagccccc atcgagaaaa ccatctccaa aaccaaaggg   1020
cagccccgag aaccacaggt gtacaccctg cccccatccc gggaggagat gaccaagaac   1080
caggtcagcc tgacctgcct ggtcaaaggc ttctacccca gcgacatcgc cgtggagtgg   1140
gagagcaatg ggcagccgga gaacaactac aagaccacac ctcccatgct ggactccgac   1200
ggctccttct tcctctacag caagctcacc gtggacaaga gcaggtggca gcaggggaac   1260
gtcttctcat gctccgtgat gcatgaggct ctgcacaacc actacacaca gaagagcctc   1320
tccctgtctc cgggtaaa                                                 1338
```

<210> SEQ ID NO 23
<211> LENGTH: 216
<212> TYPE: PRT
<213> ORGANISM: Artificial Sequence
<220> FEATURE:
<223> OTHER INFORMATION: Light chain of 4-1BB antibody YN-005; YN-006 light chain

<400> SEQUENCE: 23

```
Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Asp Ile Gly Ser Tyr
            20                  25                  30

Ser Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 24
<211> LENGTH: 648
<212> TYPE: DNA
<213> ORGANISM: Artificial Sequence
<220> FEATURE:
<223> OTHER INFORMATION: The nucleotide sequence of the light chain of
 4-1BB antibody YN-005; Nucleotide sequence encoding YN-006 light
 chain

<400> SEQUENCE: 24

```
cagagcgtct tgactcagcc accctcagcg tctgggaccc ccgggcagag ggtcaccatc      60
tcttgttctg gaagcacctc cgacatcgga agttacagcg taaactggta ccagcagctc     120
ccaggaacgg cccccaaact cctcatctat agtaataatc agcggccctc aggggtccct     180
gaccgattct ctggctccaa gtctggcacc tcagcctccc tggccatcag tgggctccag     240
tctgaggatg aggctgatta ttactgtgca gcatgggatg acagcctgaa tggttatgtc     300
ttcggaactg ggaccaagct gaccgtccta ggtcagccca aggctgcccc ctcggtcact     360
ctgttcccac cctcctctga ggagcttcaa gccaacaagg ccacactggt gtgtctcata     420
agtgacttct acccgggagc cgtgacagtg gcctggaagg cagatagcag ccccgtcaag     480
gcgggagtgg agaccaccac accctccaaa caaagcaaca caagtacgc ggccagcagc      540 tacctgagcc tgacgcctga gcagtggaag tcccacagaa gctacagctg ccaggtcacg     600
catgaaggga gcaccgtgga agacagtg gcccctacag aatgttca                    648
```

<210> SEQ ID NO 25
<211> LENGTH: 120
<212> TYPE: PRT
<213> ORGANISM: Artificial Sequence
<220> FEATURE:
<223> OTHER INFORMATION: VH of human 4-1BB antibody YN-006

<400> SEQUENCE: 25

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Asn Trp Gly Pro Ser Asp Ala Phe Asp Ile Trp Gly Gln
            100                 105                 110

Gly Thr Met Val Thr Val Ser Ser
        115                 120
```

<210> SEQ ID NO 26
<211> LENGTH: 360
<212> TYPE: DNA
<213> ORGANISM: Artificial Sequence
<220> FEATURE:
<223> OTHER INFORMATION: Nucleotide sequence encoding 4-1BB antibody
 YN-006 VH

<400> SEQUENCE: 26

```
caggtccagc tggtggaatc tgggggaggc ttggtacagc ctgggggtc cctgagactc        60 tcctgtgcag cctctggatt caccttagc agctatgcca tgagctgggt ccgccaggct       120
ccagggaagg gctggagtg gtctcagct attagtggta gtggtggtag cacatactac         180
gcagactccg tgaagggccg gttcaccatc tccagagaca attccaagaa cacgctgtat       240
cttcaaatga acagcctgag agccgaggac acggccgtgt attactgtgc gaaaactaac       300
tggggcccct ctgatgcttt tgatatctgg ggccaaggga caatggtcac cgtctcctca       360
```

<210> SEQ ID NO 27
<211> LENGTH: 446
<212> TYPE: PRT
<213> ORGANISM: Artificial Sequence
<220> FEATURE:
<223> OTHER INFORMATION: Heavy chain of 4-1BB antibody YN-006

<400> SEQUENCE: 27

```
Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Thr Asn Trp Gly Pro Ser Asp Ala Phe Asp Ile Trp Gly Gln
            100                 105                 110

Gly Thr Met Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300
```

```
Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
            435                 440                 445

<210> SEQ ID NO 28
<211> LENGTH: 1338
<212> TYPE: DNA
<213> ORGANISM: Artificial Sequence
<220> FEATURE:
<223> OTHER INFORMATION: Nucleotide sequence encoding heavy chain of
      4-1BB antibody YN-006

<400> SEQUENCE: 28
caggtccagc tggtggaatc tgggggaggc ttggtacagc ctggggggtc cctgagactc      60
tcctgtgcag cctctggatt cacctttagc agctatgcca tgagctgggt ccgccaggct     120
ccagggaagg gctggagtg gtctcagct attagtggta gtggtggtag cacatactac      180
gcagactccg tgaagggccg gttcaccatc tccagagaca attccaagaa cacgctgtat     240
cttcaaatga acagcctgag agccgaggac acggccgtgt attactgtgc gaaaactaac     300
tggggcccct ctgatgcttt tgatatctgg ggccaaggga caatggtcac cgtctcctca     360
gcgtcgacca agggcccatc ggtcttcccc ctggcgccct gctccaggag cacctccgag     420
agcacagcgg ccctgggctg cctggtcaag gactacttcc ccgaaccagt gacggtgtcg     480
tggaactcag gcgctctgac cagcggcgtg cacaccttcc cggctgtcct acagtcctca     540
ggactctact ccctcagcag cgtagtgacc gtgccctcca gcaacttcgg cacccagacc     600
tacacctgca acgtagatca caagcccagc aacaccaagg tggacaagac agttgagcgc     660
aaatgttgtg tcgagtgccc accgtgccca gcaccacctg tggcaggacc gtcagtcttc     720
ctcttccccc caaaacccaa ggacaccctc atgatctccc ggaccctga ggtcacgtgc      780 gtggtggtgg acgtgagcca cgaagacccc gaggtccagt tcaactggta cgtggacggc     840
gtggaggtgc ataatgccaa gacaaagcca cgggaggagc agttcaacag cacgttccgt     900
gtggtcagcg tcctcaccgt cgtgcaccag gactggctga acggcaagga gtacaagtgc     960
aaggtctcca acaaaggcct cccagccccc atcgagaaaa ccatctccaa aaccaaaggg    1020
cagccccgag aaccacaggt gtacaccctg cccccatccc gggaggagat gaccaagaac    1080
caggtcagcc tgacctgcct ggtcaaaggc ttctacccca gcgacatcgc cgtggagtgg    1140
gagagcaatg ggcagccgga gaacaactac aagaccacac tcccatgct ggactccgac    1200
```

```
ggctccttct tcctctacag caagctcacc gtggacaaga gcaggtggca gcagggaac      1260 gtcttctcat gctccgtgat gcatgaggct ctgcacaacc actacacaca gaagagcctc    1320
tccctgtctc cgggtaaa                                                  1338
```

<210> SEQ ID NO 29
<211> LENGTH: 2139
<212> TYPE: DNA
<213> ORGANISM: Artificial Sequence
<220> FEATURE:
<223> OTHER INFORMATION: Nucleotide sequence encoding the first
      polypeptide of PD-L1/CD137 bispecific antibody YN-007

<400> SEQUENCE: 29

```
caggtgcagc tggtgcagtc tggggctgag gtgaagaagc ctgggtcctc ggtgaaggtc     60
tcctgcaagg cttctggagg caccttcagc agctatgcta tcagctgggt gcgacaggcc    120
cctggacaag gcttgagtg gatgggaagg atcatcccta tccttggtat agcaaactac     180
gcacagaagt tccagggcag agtcacgatt accgcggaca atccacgag cacagcctac     240 atggagctga gcagcctgag atctgaggac acggccgtgt attactgtgc gagaacgatg    300
gacggataca gctatggcaa cttttgactac tggggccagg gaaccctggt cactgtctcc   360
tcagcgtcga ccaagggccc atcggtcttc ccctggcac cctcctccaa gagcacctct    420
gggggcacag cggccctggg ctgcctggtc aaggactact ccccgaacc ggtgacggtg    480 tcgtggaact caggcgccct gaccagcggc gtgcacacct tcccggctgt cctacagtcc    540
tcaggactct actccctcag cagcgtggtg accgtgccct ccagcagctt gggcacccag   600
acctacatct gcaacgtgaa tcacaagccc agcaacacca aggtggacaa gaaagttgag    660
cccaaatctt gtgacaaaac tcacacatgc ccaccgtgcc cagcacctga actcctgggg   720
ggaccgtcag tcttcctctt ccccccaaaa cccaaggaca cctcatgat ctcccggacc    780 cctgaggtca catgcgtggt ggtggacgtg agccacgaag accctgaggt caagttcaac    840
tggtacgtgg acggcgtgga ggtgcataat gccaagacaa agccgcggga ggagcagtac    900
gcaagcacgt accgtgtggt cagcgtcctc accgtcctgc accaggactg gctgaatggc    960
aaggagtaca agtgcaaggt ctccaacaaa gccctcccag cccccatcga gaaaaccatc   1020
tccaaagcca agggcagcc cgagaaccag gtgtaca ccctgccccc atcccgggaa      1080
gagatgacca agaaccaggt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttcctc tacagcaagc tcaccgtgga caagagcagg   1260
tggcagcagg ggaacgtctt ctcatgctcc gtgatgcatg aggctctgca caaccactac   1320
acgcagaaga gcctctccct gtctccgggt aaaggtggaa cggcggtgg cggaagcggc   1380 ggtggcggca gccaggtcca gctggtggaa tctggggag cttggtaca gcctgggggg   1440 tccctgagac tctcctgtgc agcctctgga ttcacctta gcagctatgc catgagctgg   1500
gtccgccagg ctccagggaa ggggctggag tgggtctcag ctattagtgg tagtggtggt   1560
agcacatact acgcagactc cgtgaagggc cggttcacca tctccagaga caattccaag   1620
aacacgctgt atcttcaaat gaacagcctg agagccgagg acacggccgt gtattactgt   1680
gcgaaaacta actggggccc ctctgatgct tttgatatct ggggccaagg acaatggtc    1740 accgtctcct cagcctccac cggtggcggt ggaagcggcg gtggcggaag cggcggtggc   1800
ggcagccaga gcgtcttgac tcagccaccc tcagcgtctg gaccccggg gcagagggtc   1860
```

```
accatctctt gttctggaag cacctccgac atcggaagtt acagcgtaaa ctggtaccag    1920
cagctcccag gaacggcccc caaactcctc atctatagta ataatcagcg gccctcaggg    1980
gtccctgacc gattctctgg ctccaagtct ggcacctcag cctccctggc catcagtggg    2040
ctccagtctg aggatgaggc tgattattac tgtgcagcat gggatgacag cctgaatggt    2100
tatgtcttcg gaactgggac caagctgacc gtcctaggt                          2139
```

<210> SEQ ID NO 30
<211> LENGTH: 713
<212> TYPE: PRT
<213> ORGANISM: Artificial Sequence
<220> FEATURE:
<223> OTHER INFORMATION: The first polypeptide of PD-L1/CD137 bispecific antibody YN-007

<400> SEQUENCE: 30

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Met Asp Gly Tyr Ser Tyr Gly Asn Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
```

```
            305                 310                 315                 320
Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Met Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Gly Gly Gly Ser Gly Gly Gly Gly Ser Gly Gly Gly Gly Ser
                450                 455                 460

Gln Val Gln Leu Val Glu Ser Gly Gly Gly Leu Val Gln Pro Gly Gly
465                 470                 475                 480

Ser Leu Arg Leu Ser Cys Ala Ala Ser Gly Phe Thr Phe Ser Ser Tyr
                485                 490                 495

Ala Met Ser Trp Val Arg Gln Ala Pro Gly Lys Gly Leu Glu Trp Val
                500                 505                 510

Ser Ala Ile Ser Gly Ser Gly Gly Ser Thr Tyr Tyr Ala Asp Ser Val
                515                 520                 525

Lys Gly Arg Phe Thr Ile Ser Arg Asp Asn Ser Lys Asn Thr Leu Tyr
                530                 535                 540

Leu Gln Met Asn Ser Leu Arg Ala Glu Asp Thr Ala Val Tyr Tyr Cys
545                 550                 555                 560

Ala Lys Thr Asn Trp Gly Pro Ser Asp Ala Phe Asp Ile Trp Gly Gln
                565                 570                 575

Gly Thr Met Val Thr Val Ser Ser Ala Ser Thr Gly Gly Gly Gly Ser
                580                 585                 590

Gly Gly Gly Gly Ser Gly Gly Gly Gly Ser Gln Ser Val Leu Thr Gln
                595                 600                 605

Pro Pro Ser Ala Ser Gly Thr Pro Gly Gln Arg Val Thr Ile Ser Cys
610                 615                 620

Ser Gly Ser Thr Ser Asp Ile Gly Ser Tyr Ser Val Asn Trp Tyr Gln
625                 630                 635                 640

Gln Leu Pro Gly Thr Ala Pro Lys Leu Leu Ile Tyr Ser Asn Asn Gln
                645                 650                 655

Arg Pro Ser Gly Val Pro Asp Arg Phe Ser Gly Ser Lys Ser Gly Thr
                660                 665                 670

Ser Ala Ser Leu Ala Ile Ser Gly Leu Gln Ser Glu Asp Glu Ala Asp
                675                 680                 685

Tyr Tyr Cys Ala Ala Trp Asp Asp Ser Leu Asn Gly Tyr Val Phe Gly
                690                 695                 700

Thr Gly Thr Lys Leu Thr Val Leu Gly
705                 710

<210> SEQ ID NO 31
```

```
<211> LENGTH: 121
<212> TYPE: PRT
<213> ORGANISM: Artificial Sequence
<220> FEATURE:
<223> OTHER INFORMATION: YN-035VH

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Arg Gly Pro Phe Ser Thr Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Met Glu Gly Tyr Gly Phe Gly Asn Phe Asp Tyr Trp Gly
            100                 105                 110

Gln Gly Thr Leu Val Thr Val Ser Ser
        115                 120

<210> SEQ ID NO 32
<211> LENGTH: 451
<212> TYPE: PRT
<213> ORGANISM: Artificial Sequence
<220> FEATURE:
<223> OTHER INFORMATION: heavy chain of YN-035

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Arg Gly Pro Phe Ser Thr Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Met Glu Gly Tyr Gly Phe Gly Asn Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
```

```
                195                 200                 205
Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 33
<211> LENGTH: 112
<212> TYPE: PRT
<213> ORGANISM: Artificial Sequence
<220> FEATURE:
<223> OTHER INFORMATION: YN-035VL/YN-036VL

<400> SEQUENCE: 33

Gln Ser Ala Leu Thr Gln Pro Ala Ser Val Ser Gly Ser Pro Gly Gln
1               5                   10                  15

Ser Ile Thr Ile Ser Cys Thr Gly Thr Val Ser Glu Val Gly Gly Tyr
                20                  25                  30

Asn Glu Val Ser Trp Tyr Gln Gln His Pro Gly Lys Ala Pro Lys Leu
            35                  40                  45

Met Ile Tyr Gly Asn Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp Ser Ser
                85                  90                  95

Leu Ser Gly Thr Val Phe Gly Gly Gly Thr Lys Leu Thr Val Leu Gly
```

-continued

<210> SEQ ID NO 34
<211> LENGTH: 217
<212> TYPE: PRT
<213> ORGANISM: Artificial Sequence
<220> FEATURE:
<223> OTHER INFORMATION: light chain of YN-035; light chain of YN-036;
    second polypeptide of YN-051; second polypeptide of YN-052

<400> SEQUENCE: 34

Gln Ser Ala Leu Thr Gln Pro Ala Ser Val Ser Gly Ser Pro Gly Gln
1               5                   10                  15

Ser Ile Thr Ile Ser Cys Thr Gly Thr Val Ser Glu Val Gly Gly Tyr
            20                  25                  30

Asn Glu Val Ser Trp Tyr Gln Gln His Pro Gly Lys Ala Pro Lys Leu
        35                  40                  45

Met Ile Tyr Gly Asn Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp Ser Ser
                85                  90                  95

Leu Ser Gly Thr Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 35
<211> LENGTH: 121
<212> TYPE: PRT
<213> ORGANISM: Artificial Sequence
<220> FEATURE:
<223> OTHER INFORMATION: YN-036VH/YN-037VH/YN-038VH/YN-039VH

<400> SEQUENCE: 35

Gln Val Gln Leu Val Gln Ser Gly Ala Glu Val Lys Lys Pro Gly Ser
1               5                   10                  15

Ser Val Lys Val Ser Cys Lys Ala Ser Arg Gly Pro Phe Ser Thr Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

-continued

```
Met Glu Leu Ser Ser Leu Arg Ser Glu Asp Thr Ala Val Tyr Tyr Cys
                85                  90                  95

Ala Arg Thr Met Gly Glu Tyr Ser Tyr Gly Asn Tyr Asp Tyr Trp Gly
            100                 105                 110

Gln Gly Thr Leu Val Thr Val Ser Ser
        115                 120

<210> SEQ ID NO 36
<211> LENGTH: 451
<212> TYPE: PRT
<213> ORGANISM: Artificial Sequence
<220> FEATURE:
<223> OTHER INFORMATION: YN-036/YN-037/YN-038/YN-039 heavy chain

<400> SEQUENCE: 36

Gln Val Gln Leu Val Gln Ser Gly Ala Glu Val Lys Lys Pro Gly Ser
1               5                   10                  15

Ser Val Lys Val Ser Cys Lys Ala Ser Arg Gly Pro Phe Ser Thr Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Met Gly Glu Tyr Ser Tyr Gly Asn Tyr Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320
```

```
Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 37
<211> LENGTH: 112
<212> TYPE: PRT
<213> ORGANISM: Artificial Sequence
<220> FEATURE:
<223> OTHER INFORMATION: YN-037VL

<400> SEQUENCE: 37

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Val Gly Gly Tyr
            20                  25                  30

Arg Glu Val Ser Trp Tyr Gln Gln His Pro Gly Lys Ala Pro Lys Leu
            35                  40                  45

Met Ile Tyr Glu Asn Ser Ile Arg Pro Ser Gly Val Ser His Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp Ser Ser
            85                  90                  95

Leu Ser Gly Thr Val Phe Gly Gly Gly Thr Lys Leu Thr Val Leu Gly
            100                 105                 110

<210> SEQ ID NO 38
<211> LENGTH: 217
<212> TYPE: PRT
<213> ORGANISM: Artificial Sequence
<220> FEATURE:
<223> OTHER INFORMATION: YN-037 light chain

<400> SEQUENCE: 38

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Val Gly Gly Tyr
            20                  25                  30

Arg Glu Val Ser Trp Tyr Gln Gln His Pro Gly Lys Ala Pro Lys Leu
            35                  40                  45

Met Ile Tyr Glu Asn Ser Ile Arg Pro Ser Gly Val Ser His Arg Phe
```

```
Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp Ser Ser
                85                  90                  95

Leu Ser Gly Thr Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 39
<211> LENGTH: 112
<212> TYPE: PRT
<213> ORGANISM: Artificial Sequence
<220> FEATURE:
<223> OTHER INFORMATION: YN-038VL

<400> SEQUENCE: 39

```
Gln Ser Ala Leu Thr Gln Pro Ala Ser Val Ser Gly Ser Pro Gly Gln
1               5                   10                  15

Ser Ile Thr Ile Ser Cys Thr Gly Thr Arg Ser Asp Val Gly Gly Tyr
            20                  25                  30

Asn Glu Val Ser Trp Tyr Gln Gln His Pro Gly Lys Ala Pro Lys Leu
        35                  40                  45

Met Ile Tyr Glu Asn Ser Ile Arg Pro Ser Gly Val Ser His Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp Ser Ser
                85                  90                  95

Leu Ser Gly Thr Val Phe Gly Gly Gly Thr Lys Leu Thr Val Leu Gly
            100                 105                 110
```

<210> SEQ ID NO 40
<211> LENGTH: 217
<212> TYPE: PRT
<213> ORGANISM: Artificial Sequence
<220> FEATURE:
<223> OTHER INFORMATION: YN-038 light chain

<400> SEQUENCE: 40

```
Gln Ser Ala Leu Thr Gln Pro Ala Ser Val Ser Gly Ser Pro Gly Gln
1               5                   10                  15

Ser Ile Thr Ile Ser Cys Thr Gly Thr Arg Ser Asp Val Gly Gly Tyr
            20                  25                  30
```

Asn Glu Val Ser Trp Tyr Gln Gln His Pro Gly Lys Ala Pro Lys Leu
                35                  40                  45

Met Ile Tyr Glu Asn Ser Ile Arg Pro Ser Gly Val Ser His Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly Thr Val Phe Gly Gly Gly Thr Lys Leu Thr Val Leu Gly
                100                 105                 110

Gln Pro Lys Ala Ala Pro Ser Val Thr Leu Phe Pro Pro Ser Ser Glu
                115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
                195                 200                 205

Lys Thr Val Ala Pro Thr Glu Cys Ser
                210                 215

<210> SEQ ID NO 41
<211> LENGTH: 112
<212> TYPE: PRT
<213> ORGANISM: Artificial Sequence
<220> FEATURE:
<223> OTHER INFORMATION: YN-039VL

<400> SEQUENCE: 41

Gln Ser Ala Leu Thr Gln Pro Ala Ser Val Ser Gly Ser Pro Gly Gln
 1               5                  10                  15

Ser Ile Thr Ile Ser Cys Thr Gly Thr Val Ser Asp Val Gly Gly Tyr
                20                  25                  30

Asn Glu Val Ser Trp Tyr Gln Gln His Pro Gly Lys Ala Pro Lys Leu
                35                  40                  45

Met Ile Tyr Glu Asn Ser Ile Arg Pro Ser Gly Val Ser His Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly Thr Val Phe Gly Gly Gly Thr Lys Leu Thr Val Leu Gly
                100                 105                 110

<210> SEQ ID NO 42
<211> LENGTH: 217
<212> TYPE: PRT
<213> ORGANISM: Artificial Sequence
<220> FEATURE:
<223> OTHER INFORMATION: YN-039 light chain

<400> SEQUENCE: 42

Gln Ser Ala Leu Thr Gln Pro Ala Ser Val Ser Gly Ser Pro Gly Gln
 1               5                  10                  15

-continued

Ser Ile Thr Ile Ser Cys Thr Gly Thr Val Ser Asp Val Gly Gly Tyr
            20                  25                  30

Asn Glu Val Ser Trp Tyr Gln Gln His Pro Gly Lys Ala Pro Lys Leu
         35                  40                  45

Met Ile Tyr Glu Asn Ser Ile Arg Pro Ser Gly Val Ser His Arg Phe
     50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Asp Ser Ser
                85                  90                  95

Leu Ser Gly Thr Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 43
<211> LENGTH: 713
<212> TYPE: PRT
<213> ORGANISM: Artificial Sequence
<220> FEATURE:
<223> OTHER INFORMATION: first polypeptide of YN-051

<400> SEQUENCE: 43

Gln Val Gln Leu Val Gln Ser Gly Ala Glu Val Lys Lys Pro Gly Ser
1               5                   10                  15

Ser Val Lys Val Ser Cys Lys Ala Ser Arg Gly Pro Phe Ser Thr Tyr
            20                  25                  30

Ala Ile Ser Trp Val Arg Gln Ala Pro Gly Gln Gly Leu Glu Trp Met
         35                  40                  45

Gly Arg Ile Ile Pro Ile Leu Gly Ile Ala Asn Tyr Ala Gln Lys Phe
     50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Met Glu Gly Tyr Gly Phe Gly Asn Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

-continued

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Ala Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Gly Gly Gly Ser Gly Gly Gly Gly Ser Gly Gly Gly Gly Ser
    450                 455                 460

Gln Val Gln Leu Val Glu Ser Gly Gly Gly Leu Val Gln Pro Gly Gly
465                 470                 475                 480

Ser Leu Arg Leu Ser Cys Ala Ala Ser Gly Phe Thr Phe Ser Ser Tyr
            485                 490                 495

Ala Met Ser Trp Val Arg Gln Ala Pro Gly Lys Gly Leu Glu Trp Val
            500                 505                 510

Ser Ala Ile Ser Gly Ser Gly Gly Ser Thr Tyr Tyr Ala Asp Ser Val
            515                 520                 525

Lys Gly Arg Phe Thr Ile Ser Arg Asp Asn Ser Lys Asn Thr Leu Tyr
        530                 535                 540

Leu Gln Met Asn Ser Leu Arg Ala Glu Asp Thr Ala Val Tyr Tyr Cys
545                 550                 555                 560

Ala Lys Thr Asn Trp Gly Pro Ser Asp Ala Phe Asp Ile Trp Gly Gln
            565                 570                 575

```
Gly Thr Met Val Thr Val Ser Ala Ser Thr Gly Gly Gly Ser
            580                 585                 590

Gly Gly Gly Gly Ser Gly Gly Gly Ser Gln Ser Val Leu Thr Gln
        595                 600                 605

Pro Pro Ser Ala Ser Gly Thr Pro Gly Gln Arg Val Thr Ile Ser Cys
        610                 615                 620

Ser Gly Ser Thr Ser Asp Ile Gly Ser Tyr Ser Val Asn Trp Tyr Gln
625                 630                 635                 640

Gln Leu Pro Gly Thr Ala Pro Lys Leu Leu Ile Tyr Ser Asn Asn Gln
                645                 650                 655

Arg Pro Ser Gly Val Pro Asp Arg Phe Ser Gly Ser Lys Ser Gly Thr
            660                 665                 670

Ser Ala Ser Leu Ala Ile Ser Gly Leu Gln Ser Glu Asp Glu Ala Asp
        675                 680                 685

Tyr Tyr Cys Ala Ala Trp Asp Asp Ser Leu Asn Gly Tyr Val Phe Gly
        690                 695                 700

Thr Gly Thr Lys Leu Thr Val Leu Gly
705                 710

<210> SEQ ID NO 44
<211> LENGTH: 713
<212> TYPE: PRT
<213> ORGANISM: Artificial Sequence
<220> FEATURE:
<223> OTHER INFORMATION: first polypeptide of YN-052

<400> SEQUENCE: 44

Gln Val Gln Leu Val Gln Ser Gly Ala Glu Val Lys Lys Pro Gly Ser
1               5                   10                  15

Ser Val Lys Val Ser Cys Lys Ala Ser Arg Gly Pro Phe Ser Thr Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Met Gly Glu Tyr Ser Tyr Gly Asn Tyr Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

-continued

```
Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Ala Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Gly Gly Gly Ser Gly Gly Gly Gly Ser Gly Gly Gly Gly Ser
450                 455                 460

Gln Val Gln Leu Val Glu Ser Gly Gly Gly Leu Val Gln Pro Gly Gly
465                 470                 475                 480

Ser Leu Arg Leu Ser Cys Ala Ala Ser Gly Phe Thr Phe Ser Ser Tyr
            485                 490                 495

Ala Met Ser Trp Val Arg Gln Ala Pro Gly Lys Gly Leu Glu Trp Val
            500                 505                 510

Ser Ala Ile Ser Gly Ser Gly Gly Ser Thr Tyr Tyr Ala Asp Ser Val
            515                 520                 525

Lys Gly Arg Phe Thr Ile Ser Arg Asp Asn Ser Lys Asn Thr Leu Tyr
            530                 535                 540

Leu Gln Met Asn Ser Leu Arg Ala Glu Asp Thr Ala Val Tyr Tyr Cys
545                 550                 555                 560

Ala Lys Thr Asn Trp Gly Pro Ser Asp Ala Phe Asp Ile Trp Gly Gln
                565                 570                 575

Gly Thr Met Val Thr Val Ser Ser Ala Ser Thr Gly Gly Gly Gly Ser
            580                 585                 590

Gly Gly Gly Gly Ser Gly Gly Gly Ser Gln Ser Val Leu Thr Gln
            595                 600                 605

Pro Pro Ser Ala Ser Gly Thr Pro Gly Gln Arg Val Thr Ile Ser Cys
            610                 615                 620

Ser Gly Ser Thr Ser Asp Ile Gly Ser Tyr Ser Val Asn Trp Tyr Gln
625                 630                 635                 640

Gln Leu Pro Gly Thr Ala Pro Lys Leu Leu Ile Tyr Ser Asn Asn Gln
```

```
                    645                 650                 655
Arg Pro Ser Gly Val Pro Asp Arg Phe Ser Gly Ser Lys Ser Gly Thr
            660                 665                 670

Ser Ala Ser Leu Ala Ile Ser Gly Leu Gln Ser Glu Asp Glu Ala Asp
        675                 680                 685

Tyr Tyr Cys Ala Ala Trp Asp Asp Ser Leu Asn Gly Tyr Val Phe Gly
    690                 695                 700

Thr Gly Thr Lys Leu Thr Val Leu Gly
705                 710

<210> SEQ ID NO 45
<211> LENGTH: 5
<212> TYPE: PRT
<213> ORGANISM: Artificial Sequence
<220> FEATURE:
<223> OTHER INFORMATION: HCDR1 of PD-L1 antibody
<220> FEATURE:
<221> NAME/KEY: X1
<222> LOCATION: (1)..(1)
<223> OTHER INFORMATION: X1 is S or T

<400> SEQUENCE: 45

Xaa Tyr Ala Ile Ser
1               5

<210> SEQ ID NO 46
<211> LENGTH: 5
<212> TYPE: PRT
<213> ORGANISM: Artificial Sequence
<220> FEATURE:
<223> OTHER INFORMATION: HCDR1 of YN-002; HCDR1 of YN-003

<400> SEQUENCE: 46

Ser Tyr Ala Ile Ser
1               5

<210> SEQ ID NO 47
<211> LENGTH: 5
<212> TYPE: PRT
<213> ORGANISM: Artificial Sequence
<220> FEATURE:
<223> OTHER INFORMATION: HCDR1 of YN-035; HCDR1 of YN-036; HCDR1 of
      YN-037; HCDR1 of YN-038; HCDR1 of YN-039

<400> SEQUENCE: 47

Thr Tyr Ala Ile Ser
1               5

<210> SEQ ID NO 48
<211> LENGTH: 17
<212> TYPE: PRT
<213> ORGANISM: Artificial Sequence
<220> FEATURE:
<223> OTHER INFORMATION: HCDR2 of YN-002; HCDR2 of YN-003; HCDR2 of
      YN-035; HCDR2 of YN-036; HCDR2 of YN-037; HCDR2 of YN-038;
      HCDR2 of YN-039; HCDR2 of PD-L1 antibody

<400> SEQUENCE: 48

Arg Ile Ile Pro Ile Leu Gly Ile Ala Asn Tyr Ala Gln Lys Phe Gln
1               5                   10                  15

Gly

<210> SEQ ID NO 49
<211> LENGTH: 12
<212> TYPE: PRT
```

```
<213> ORGANISM: Artificial Sequence
<220> FEATURE:
<223> OTHER INFORMATION: HCDR3 of PD-L1 antibody
<220> FEATURE:
<221> NAME/KEY: X1
<222> LOCATION: (3)..(3)
<223> OTHER INFORMATION: X1is DE or G
<220> FEATURE:
<221> NAME/KEY: X2
<222> LOCATION: (4)..(4)
<223> OTHER INFORMATION: X2 is G or E
<220> FEATURE:
<221> NAME/KEY: X3
<222> LOCATION: (6)..(6)
<223> OTHER INFORMATION: X3 is S or G
<220> FEATURE:
<221> NAME/KEY: X4
<222> LOCATION: (7)..(7)
<223> OTHER INFORMATION: X4 is Y or F
<220> FEATURE:
<221> NAME/KEY: X5
<222> LOCATION: (10)..(10)
<223> OTHER INFORMATION: X5 is F or Y

<400> SEQUENCE: 49

Thr Met Xaa Xaa Tyr Xaa Xaa Gly Asn Xaa Asp Tyr
1               5                   10

<210> SEQ ID NO 50
<211> LENGTH: 12
<212> TYPE: PRT
<213> ORGANISM: Artificial Sequence
<220> FEATURE:
<223> OTHER INFORMATION: HCDR3 of YN-002; HCDR3 of YN-003

<400> SEQUENCE: 50

Thr Met Asp Gly Tyr Ser Tyr Gly Asn Phe Asp Tyr
1               5                   10

<210> SEQ ID NO 51
<211> LENGTH: 12
<212> TYPE: PRT
<213> ORGANISM: Artificial Sequence
<220> FEATURE:
<223> OTHER INFORMATION: HCDR3 of YN-035

<400> SEQUENCE: 51

Thr Met Glu Gly Tyr Gly Phe Gly Asn Phe Asp Tyr
1               5                   10

<210> SEQ ID NO 52
<211> LENGTH: 12
<212> TYPE: PRT
<213> ORGANISM: Artificial Sequence
<220> FEATURE:
<223> OTHER INFORMATION: HCDR3 of YN-036; HCDR3 of YN-037; HCDR3 of
     YN-038; HCDR3 of YN-039

<400> SEQUENCE: 52

Thr Met Gly Glu Tyr Ser Tyr Gly Asn Tyr Asp Tyr
1               5                   10

<210> SEQ ID NO 53
<211> LENGTH: 14
<212> TYPE: PRT
<213> ORGANISM: Artificial Sequence
<220> FEATURE:
<223> OTHER INFORMATION: LCDR1 of PD-L1 antibody
<220> FEATURE:
<221> NAME/KEY: X1
<222> LOCATION: (4)..(4)
```

```
<223> OTHER INFORMATION: X1 is SR or V
<220> FEATURE:
<221> NAME/KEY: X2
<222> LOCATION: (6)..(6)
<223> OTHER INFORMATION: X2 is DE or S
<220> FEATURE:
<221> NAME/KEY: X3
<222> LOCATION: (11)..(11)
<223> OTHER INFORMATION: X3 is N or R
<220> FEATURE:
<221> NAME/KEY: X4
<222> LOCATION: (12)..(12)
<223> OTHER INFORMATION: X4 is Y or E

<400> SEQUENCE: 53

Thr Gly Thr Xaa Ser Xaa Val Gly Gly Tyr Xaa Xaa Val Ser
1               5                   10

<210> SEQ ID NO 54
<211> LENGTH: 14
<212> TYPE: PRT
<213> ORGANISM: Artificial Sequence
<220> FEATURE:
<223> OTHER INFORMATION: LCDR1 of YN-002; LCDR1 of YN-003

<400> SEQUENCE: 54

Thr Gly Thr Ser Ser Asp Val Gly Gly Tyr Asn Tyr Val Ser
1               5                   10

<210> SEQ ID NO 55
<211> LENGTH: 14
<212> TYPE: PRT
<213> ORGANISM: Artificial Sequence
<220> FEATURE:
<223> OTHER INFORMATION: LCDR1 of YN-035; LCDR1 of YN-036

<400> SEQUENCE: 55

Thr Gly Thr Val Ser Glu Val Gly Gly Tyr Asn Glu Val Ser
1               5                   10

<210> SEQ ID NO 56
<211> LENGTH: 14
<212> TYPE: PRT
<213> ORGANISM: Artificial Sequence
<220> FEATURE:
<223> OTHER INFORMATION: LCDR1 of YN-037

<400> SEQUENCE: 56

Thr Gly Thr Ser Ser Ser Val Gly Gly Tyr Arg Glu Val Ser
1               5                   10

<210> SEQ ID NO 57
<211> LENGTH: 14
<212> TYPE: PRT
<213> ORGANISM: Artificial Sequence
<220> FEATURE:
<223> OTHER INFORMATION: LCDR1 of YN-038

<400> SEQUENCE: 57

Thr Gly Thr Arg Ser Asp Val Gly Gly Tyr Asn Glu Val Ser
1               5                   10

<210> SEQ ID NO 58
<211> LENGTH: 14
<212> TYPE: PRT
<213> ORGANISM: Artificial Sequence
<220> FEATURE:
<223> OTHER INFORMATION: LCDR1 of YN-039
```

<400> SEQUENCE: 58

Thr Gly Thr Val Ser Asp Val Gly Gly Tyr Asn Glu Val Ser
1               5                   10

<210> SEQ ID NO 59
<211> LENGTH: 7
<212> TYPE: PRT
<213> ORGANISM: Artificial Sequence
<220> FEATURE:
<223> OTHER INFORMATION: LCDR2 of PD-L1 antibody
<220> FEATURE:
<221> NAME/KEY: X1
<222> LOCATION: (1)..(1)
<223> OTHER INFORMATION: X1 is G or E
<220> FEATURE:
<221> NAME/KEY: X2
<222> LOCATION: (4)..(4)
<223> OTHER INFORMATION: X2 is N or I

<400> SEQUENCE: 59

Xaa Asn Ser Xaa Arg Pro Ser
1               5

<210> SEQ ID NO 60
<211> LENGTH: 7
<212> TYPE: PRT
<213> ORGANISM: Artificial Sequence
<220> FEATURE:
<223> OTHER INFORMATION: LCDR2 of YN-002; LCDR2 of YN-003; LCDR2 of
      YN-035; LCDR2 of YN-036

<400> SEQUENCE: 60

Gly Asn Ser Asn Arg Pro Ser
1               5

<210> SEQ ID NO 61
<211> LENGTH: 7
<212> TYPE: PRT
<213> ORGANISM: Artificial Sequence
<220> FEATURE:
<223> OTHER INFORMATION: LCDR2 of YN-037; LCDR2 of YN-038; LCDR2 of
      YN-039

<400> SEQUENCE: 61

Glu Asn Ser Ile Arg Pro Ser
1               5

<210> SEQ ID NO 62
<211> LENGTH: 11
<212> TYPE: PRT
<213> ORGANISM: Artificial Sequence
<220> FEATURE:
<223> OTHER INFORMATION: LCDR3 of PD-L1 antibody
<220> FEATURE:
<221> NAME/KEY: X1
<222> LOCATION: (10)..(10)
<223> OTHER INFORMATION: X1 is S or T

<400> SEQUENCE: 62

Gln Ser Tyr Asp Ser Ser Leu Ser Gly Xaa Val
1               5                   10

<210> SEQ ID NO 63
<211> LENGTH: 11
<212> TYPE: PRT
<213> ORGANISM: Artificial Sequence
<220> FEATURE:
<223> OTHER INFORMATION: LCDR3 of YN-002; LCDR3 of YN-003

```
<400> SEQUENCE: 63

Gln Ser Tyr Asp Ser Ser Leu Ser Gly Ser Val
1               5                   10

<210> SEQ ID NO 64
<211> LENGTH: 11
<212> TYPE: PRT
<213> ORGANISM: Artificial Sequence
<220> FEATURE:
<223> OTHER INFORMATION: LCDR3 of YN-035; LCDR3 of YN-036; LCDR3 of
      YN-037; LCDR3 of YN-038; LCDR3 of YN-039

<400> SEQUENCE: 64

Gln Ser Tyr Asp Ser Ser Leu Ser Gly Thr Val
1               5                   10

<210> SEQ ID NO 65
<211> LENGTH: 30
<212> TYPE: PRT
<213> ORGANISM: Artificial Sequence
<220> FEATURE:
<223> OTHER INFORMATION: H-FR1 of YN-002

<400> SEQUENCE: 65

Gln Val Gln Leu Val Gln Ser Gly Ala Glu Val Arg Lys Pro Gly Ser
1               5                   10                  15

Ser Val Lys Val Ser Cys Lys Ala Ser Gly Gly Thr Phe Ser
            20                  25                  30

<210> SEQ ID NO 66
<211> LENGTH: 30
<212> TYPE: PRT
<213> ORGANISM: Artificial Sequence
<220> FEATURE:
<223> OTHER INFORMATION: H-FR1 of YN-003

<400> SEQUENCE: 66

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser
            20                  25                  30

<210> SEQ ID NO 67
<211> LENGTH: 30
<212> TYPE: PRT
<213> ORGANISM: Artificial Sequence
<220> FEATURE:
<223> OTHER INFORMATION: H-FR1 of YN-035~YN-039

<400> SEQUENCE: 67

Gln Val Gln Leu Val Gln Ser Gly Ala Glu Val Lys Lys Pro Gly Ser
1               5                   10                  15

Ser Val Lys Val Ser Cys Lys Ala Ser Arg Gly Pro Phe Ser
            20                  25                  30

<210> SEQ ID NO 68
<211> LENGTH: 14
<212> TYPE: PRT
<213> ORGANISM: Artificial Sequence
<220> FEATURE:
<223> OTHER INFORMATION: H-FR2 of YN-002; H-FR2 of YN-003; H-FR2 of
      YN-035~YN-039

<400> SEQUENCE: 68

Trp Val Arg Gln Ala Pro Gly Gln Gly Leu Glu Trp Met Gly
```

```
<210> SEQ ID NO 69
<211> LENGTH: 32
<212> TYPE: PRT
<213> ORGANISM: Artificial Sequence
<220> FEATURE:
<223> OTHER INFORMATION: H-FR3 of YN-002; H-FR3 of YN-003; H-FR3 of
      YN-035~YN-039

<400> SEQUENCE: 69

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 70
<211> LENGTH: 11
<212> TYPE: PRT
<213> ORGANISM: Artificial Sequence
<220> FEATURE:
<223> OTHER INFORMATION: H-FR4 of YN-002; H-FR4 of YN-003; H-FR4 of
      YN-035~YN-039

<400> SEQUENCE: 70

Trp Gly Gln Gly Thr Leu Val Thr Val Ser Ser
1               5                   10

<210> SEQ ID NO 71
<211> LENGTH: 22
<212> TYPE: PRT
<213> ORGANISM: Artificial Sequence
<220> FEATURE:
<223> OTHER INFORMATION: L-FR1 of YN-002; L-FR1 of YN-003; L-FR1 of
      YN-035~YN-039

<400> SEQUENCE: 71

Gln Ser Ala Leu Thr Gln Pro Ala Ser Val Ser Gly Ser Pro Gly Gln
1               5                   10                  15

Ser Ile Thr Ile Ser Cys
            20

<210> SEQ ID NO 72
<211> LENGTH: 15
<212> TYPE: PRT
<213> ORGANISM: Artificial Sequence
<220> FEATURE:
<223> OTHER INFORMATION: L-FR2 of YN-002; L-FR2 of YN-003; L-FR2 of
      YN-035~YN-039

<400> SEQUENCE: 72

Trp Tyr Gln Gln His Pro Gly Lys Ala Pro Lys Leu Met Ile Tyr
1               5                   10                  15

<210> SEQ ID NO 73
<211> LENGTH: 32
<212> TYPE: PRT
<213> ORGANISM: Artificial Sequence
<220> FEATURE:
<223> OTHER INFORMATION: L-FR3 of YN-002

<400> SEQUENCE: 73

Gly Val Pro Asp Arg Phe Ser Gly Ser Lys Ser Gly Thr Ser Ala Ser
1               5                   10                  15

Leu Ala Ile Thr Gly Leu Gln Ala Glu Asp Glu Ala Asp Tyr Tyr Cys
            20                  25                  30
```

<210> SEQ ID NO 74
<211> LENGTH: 32
<212> TYPE: PRT
<213> ORGANISM: Artificial Sequence
<220> FEATURE:
<223> OTHER INFORMATION: L-FR3 of YN-003; L-FR3 of YN-035~YN-036

<400> SEQUENCE: 74

Gly Val Ser Asn Arg Phe Ser Gly Ser Lys Ser Gly Asn Thr Ala Ser
1               5                   10                  15

Leu Thr Ile Ser Gly Leu Gln Ala Glu Asp Glu Ala Asp Tyr Tyr Cys
            20                  25                  30

<210> SEQ ID NO 75
<211> LENGTH: 32
<212> TYPE: PRT
<213> ORGANISM: Artificial Sequence
<220> FEATURE:
<223> OTHER INFORMATION: L-FR3 of YN-037~YN-039

<400> SEQUENCE: 75

Gly Val Ser His Arg Phe Ser Gly Ser Lys Ser Gly Asn Thr Ala Ser
1               5                   10                  15

Leu Thr Ile Ser Gly Leu Gln Ala Glu Asp Glu Ala Asp Tyr Tyr Cys
            20                  25                  30

<210> SEQ ID NO 76
<211> LENGTH: 11
<212> TYPE: PRT
<213> ORGANISM: Artificial Sequence
<220> FEATURE:
<223> OTHER INFORMATION: L-FR4 of YN-002; L-FR4 of YN-003; L-FR4 of
      YN-035~YN-039

<400> SEQUENCE: 76

Phe Gly Gly Gly Thr Lys Leu Thr Val Leu Gly
1               5                   10

<210> SEQ ID NO 77
<211> LENGTH: 5
<212> TYPE: PRT
<213> ORGANISM: Artificial Sequence
<220> FEATURE:
<223> OTHER INFORMATION: 4-1BB antibody YN-005/006 H-CDR1

<400> SEQUENCE: 77

Ser Tyr Ala Met Ser
1               5

<210> SEQ ID NO 78
<211> LENGTH: 17
<212> TYPE: PRT
<213> ORGANISM: Artificial Sequence
<220> FEATURE:
<223> OTHER INFORMATION: 4-1BB antibody YN-005/006 H-CDR2

<400> SEQUENCE: 78

Ala Ile Ser Gly Ser Gly Gly Ser Thr Tyr Tyr Ala Asp Ser Val Lys
1               5                   10                  15

Gly

<210> SEQ ID NO 79
<211> LENGTH: 11
<212> TYPE: PRT

<213> ORGANISM: Artificial Sequence
<220> FEATURE:
<223> OTHER INFORMATION: 4-1BB antibody YN-005/006 H-CDR3

<400> SEQUENCE: 79

Thr Asn Trp Gly Pro Ser Asp Ala Phe Asp Ile
1               5                   10

<210> SEQ ID NO 80
<211> LENGTH: 13
<212> TYPE: PRT
<213> ORGANISM: Artificial Sequence
<220> FEATURE:
<223> OTHER INFORMATION: 4-1BB antibody YN-005/006 L-CDR1

<400> SEQUENCE: 80

Ser Gly Ser Thr Ser Asp Ile Gly Ser Tyr Ser Val Asn
1               5                   10

<210> SEQ ID NO 81
<211> LENGTH: 7
<212> TYPE: PRT
<213> ORGANISM: Artificial Sequence
<220> FEATURE:
<223> OTHER INFORMATION: 4-1BB antibody YN-005/006 L-CDR2

<400> SEQUENCE: 81

Ser Asn Asn Gln Arg Pro Ser
1               5

<210> SEQ ID NO 82
<211> LENGTH: 11
<212> TYPE: PRT
<213> ORGANISM: Artificial Sequence
<220> FEATURE:
<223> OTHER INFORMATION: 4-1BB antibody YN-005/006 L-CDR3

<400> SEQUENCE: 82

Ala Ala Trp Asp Asp Ser Leu Asn Gly Tyr Val
1               5                   10

<210> SEQ ID NO 83
<211> LENGTH: 249
<212> TYPE: PRT
<213> ORGANISM: Artificial Sequence
<220> FEATURE:
<223> OTHER INFORMATION: 4-1BB antibody scFv

<400> SEQUENCE: 83

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Asn Trp Gly Pro Ser Asp Ala Phe Asp Ile Trp Gly Gln
            100                 105                 110

```
Gly Thr Met Val Thr Val Ser Ser Ala Ser Thr Gly Gly Gly Ser
            115                 120                 125

Gly Gly Gly Gly Ser Gly Gly Gly Ser Gln Ser Val Leu Thr Gln
        130                 135                 140

Pro Pro Ser Ala Ser Gly Thr Pro Gly Gln Arg Val Thr Ile Ser Cys
145                 150                 155                 160

Ser Gly Ser Thr Ser Asp Ile Gly Ser Tyr Ser Val Asn Trp Tyr Gln
                165                 170                 175

Gln Leu Pro Gly Thr Ala Pro Lys Leu Leu Ile Tyr Ser Asn Asn Gln
            180                 185                 190

Arg Pro Ser Gly Val Pro Asp Arg Phe Ser Gly Ser Lys Ser Gly Thr
        195                 200                 205

Ser Ala Ser Leu Ala Ile Ser Gly Leu Gln Ser Glu Asp Glu Ala Asp
    210                 215                 220

Tyr Tyr Cys Ala Ala Trp Asp Asp Ser Leu Asn Gly Tyr Val Phe Gly
225                 230                 235                 240

Thr Gly Thr Lys Leu Thr Val Leu Gly
                245
```

```
<210> SEQ ID NO 84
<211> LENGTH: 30
<212> TYPE: PRT
<213> ORGANISM: Artificial Sequence
<220> FEATURE:
<223> OTHER INFORMATION: 4-1BB antibody YN-005 H-FR1

<400> SEQUENCE: 84

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 85
<211> LENGTH: 30
<212> TYPE: PRT
<213> ORGANISM: Artificial Sequence
<220> FEATURE:
<223> OTHER INFORMATION: 4-1BB antibody YN-006 H-FR1

<400> SEQUENCE: 85

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 86
<211> LENGTH: 14
<212> TYPE: PRT
<213> ORGANISM: Artificial Sequence
<220> FEATURE:
<223> OTHER INFORMATION: 4-1BB antibody YN-005/006 H-FR2

<400> SEQUENCE: 86

Trp Val Arg Gln Ala Pro Gly Lys Gly Leu Glu Trp Val Ser
1               5                   10

<210> SEQ ID NO 87
<211> LENGTH: 32
<212> TYPE: PRT
<213> ORGANISM: Artificial Sequence
<220> FEATURE:
<223> OTHER INFORMATION: 4-1BB antibody YN-005/006 H-FR3
```

<400> SEQUENCE: 87

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
                20                  25                  30

<210> SEQ ID NO 88
<211> LENGTH: 11
<212> TYPE: PRT
<213> ORGANISM: Artificial Sequence
<220> FEATURE:
<223> OTHER INFORMATION: 4-1BB antibody YN-005/006 H-FR4

<400> SEQUENCE: 88

Trp Gly Gln Gly Thr Met Val Thr Val Ser Ser
1               5                   10

<210> SEQ ID NO 89
<211> LENGTH: 22
<212> TYPE: PRT
<213> ORGANISM: Artificial Sequence
<220> FEATURE:
<223> OTHER INFORMATION: 4-1BB antibody YN-005/006 L-FR1

<400> SEQUENCE: 89

Gln Ser Val Leu Thr Gln Pro Pro Ser Ala Ser Gly Thr Pro Gly Gln
1               5                   10                  15

Arg Val Thr Ile Ser Cys
                20

<210> SEQ ID NO 90
<211> LENGTH: 15
<212> TYPE: PRT
<213> ORGANISM: Artificial Sequence
<220> FEATURE:
<223> OTHER INFORMATION: 4-1BB antibody YN-005/006 L-FR2

<400> SEQUENCE: 90

Trp Tyr Gln Gln Leu Pro Gly Thr Ala Pro Lys Leu Leu Ile Tyr
1               5                   10                  15

<210> SEQ ID NO 91
<211> LENGTH: 32
<212> TYPE: PRT
<213> ORGANISM: Artificial Sequence
<220> FEATURE:
<223> OTHER INFORMATION: 4-1BB antibody YN-005/006 L-FR3

<400> SEQUENCE: 91

Gly Val Pro Asp Arg Phe Ser Gly Ser Lys Ser Gly Thr Ser Ala Ser
1               5                   10                  15

Leu Ala Ile Ser Gly Leu Gln Ser Glu Asp Glu Ala Asp Tyr Tyr Cys
                20                  25                  30

<210> SEQ ID NO 92
<211> LENGTH: 11
<212> TYPE: PRT
<213> ORGANISM: Artificial Sequence -continued

```
<220> FEATURE:
<223> OTHER INFORMATION: 4-1BB antibody YN-005/006 L-FR4

<400> SEQUENCE: 92

Phe Gly Thr Gly Thr Lys Leu Thr Val Leu Gly
1               5                   10
```